United States Patent
Björsne et al.

(10) Patent No.: US 6,559,162 B2
(45) Date of Patent: May 6, 2003

(54) AZABICYCLOOCTANE DERIVATIVES USEFUL IN THE TREATMENT OF CARDIAC ARRHYTHMIAS

(75) Inventors: Magnus Björsne, Västra Frölunda (SE); Fritiof Pontén, Askim (SE); Gert Strandlund, Lindome (SE); Peder Svensson, Gothenburg (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/763,892

(22) PCT Filed: Dec. 19, 2000

(86) PCT No.: PCT/SE00/02604

§ 371 (c)(1),
(2), (4) Date: Feb. 28, 2001

(87) PCT Pub. No.: WO01/47893

PCT Pub. Date: Jul. 5, 2001

(65) Prior Publication Data

US 2002/0137766 A1 Sep. 26, 2002

(30) Foreign Application Priority Data

Dec. 23, 1999 (SE) ................................. 9904765

(51) Int. Cl.⁷ ................. A61K 31/439; C07D 221/22
(52) U.S. Cl. ................. 514/299; 546/112; 546/124; 514/304
(58) Field of Search ................. 514/299, 304; 546/112, 124

(56) References Cited

U.S. PATENT DOCUMENTS

| | | | |
|---|---|---|---|
| 3,962,449 A | 6/1976 | Binnig et al. | |
| 4,459,301 A | 7/1984 | Binnig et al. | |
| 4,550,112 A | 10/1985 | Shoen et al. | |
| 4,556,662 A | 12/1985 | Binnig et al. | |
| 4,719,217 A | * 1/1988 | King et al. | 514/299 |
| 5,070,094 A | * 12/1991 | Fowler | 514/304 |
| 5,084,572 A | 1/1992 | Berlin et al. | |
| 5,468,858 A | 11/1995 | Berlin et al. | |

FOREIGN PATENT DOCUMENTS

| | | |
|---|---|---|
| EP | 212 802 | 3/1987 |
| EP | 306 871 | 3/1989 |
| EP | 308 843 | 3/1989 |
| EP | 416 521 | 3/1991 |
| EP | 645 391 | 3/1995 |
| EP | 665 228 | 8/1995 |
| WO | 91/07405 | 5/1991 |
| WO | 95/03301 | 2/1995 |
| WO | 97/36871 | 10/1997 |
| WO | 98/18788 | 5/1998 |
| WO | 99/31100 | 6/1999 |
| WO | 00/61569 | 10/2000 |
| WO | 00/71529 A1 | 11/2000 |

OTHER PUBLICATIONS

Villa et al, "3,8–Diazabicyclo . . . ," Eur. J. Med. Chem., vol. 36, pp. 495–506 (2001).
Pharmacol. Res. 24, 149 (1991).
Anal. Sci. 9, 429 (1993).
Circulation, 90, 2032 (1994).
J. Heterocycl. Chem. 31(2), 313–318 (1994).
J. Med. Chem. 39, 2559 (1996).

* cited by examiner

Primary Examiner—Charanjit S. Aulakh
(74) Attorney, Agent, or Firm—Nixon & Vanderhye

(57) ABSTRACT

Compounds of formula I,

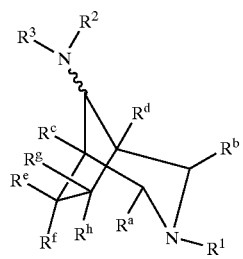

wherein $R^1$, $R^2$, $R^3$ and $R^a$–$R^h$ are as defined in the specification. The compounds are useful in the prophylaxis and in the treatment of arrhythmias, in particular atrial and ventricular arrhythmias.

47 Claims, No Drawings

AZABICYCLOOCTANE DERIVATIVES USEFUL IN THE TREATMENT OF CARDIAC ARRHYTHMIAS

This application is a 371 of PCT/SE00/02064 filed Dec. 19, 2000, now WO 01/47893 Jul. 5, 2000.

FIELD OF THE INVENTION

This invention relates to novel pharmaceutically useful compounds, in particular compounds which are useful in the treatment of cardiac arrhythmias.

BACKGROUND AND PRIOR ART

Cardiac arrhythmias may be defined as abnormalities in the rate, regularity, or site of origin of the cardiac impulse or as disturbances in conduction which causes an abnormal sequence of activation. Arrhythmias may be classified clinically by means of the presumed site of origin (i.e. as supraventricular, including atrial and atrioventricular, arrhythmias and ventricular arrhythmias) and/or by means of rate (i.e. bradyarrhythmias (slow) and tachyarrhythmias (fast)).

In the treatment of cardiac arrhythmias, the negative outcome in clinical trials (see, for example, the outcome of the Cardiac Arrhythmia Suppression Trial (CAST) reported in New England Journal of Medicine, 321, 406 (1989)) with "traditional" antiarrhythmic drugs, which act primarily by slowing the conduction velocity (class I antiarrhythmic drugs), has prompted drug development towards compounds which selectively delay cardiac repolarization, thus prolonging the QT interval. Class III antiarrhythmic drugs may be defined as drugs which prolong the trans-membrane action potential duration (which can be caused by a block of outward $K^+$ currents or from an increase of inward ion currents) and refractoriness, without affecting cardiac conduction.

One of the key disadvantages of hitherto known drugs which act by delaying repolarization (class III or otherwise) is that they all are known to exhibit a unique form of proarrhythmia known as torsades de pointes (turning of points), which may, on occasion be fatal. From the point of view of safety, the minimisation of this phenomenon (which has also been shown to be exhibited as a result of administration of noncardiac drugs such as phenotiazines, tricyclic antidepressants, antihistamines and antibiotics) is a key problem to be solved in the provision of effective antiarrhythmic drugs.

Antiarrhythmic drugs based on bispidines (3,7-diazabicyclo[3.3.1]nonanes), are known from inter alia international patent applications WO 91/07405 and WO 99/31100, European patent applications 306 871, 308 843 and 665 228 and U.S. Pat. Nos. 3,962,449, 4,556,662, 4,550,112, 4,459,301 and 5,468,858, as well as journal articles including inter alia J. Med. Chem. 39, 2559, (1996), Pharmacol. Res., 24, 149 (1991), Circulation, 90, 2032 (1994) and Anal. Sci. 9, 429, (1993). 3-Azabicyclo[3.2.1] octane compounds are neither disclosed nor suggested in any of these documents.

Compounds based on 3-azabicyclo[3.2.1]octanes are known for use in a variety of other medical applications including serotonin antagonism (as described in EP 212 802 and EP 645 391), neurokinin-I receptor antagonism (as described in WO 98/18788), nitric oxide synthase inhibition (as described in WO 97/36871) and analgesia (as described in Rico, B, et al., *J. Heterocycl. Chem.* 31(2), 313–318 (1994)). None of these documents either disclose or suggest the use of 3-azabicyclo[3.2.1]octane-based compounds as antiarrhythmic agents.

We have surprisingly found that a novel group of 3-azabicyclo[3.2.1]octane-based compounds exhibit electrophysiological activity, preferably class III electrophysiological activity, and are therefore expected to be useful in the treatment of cardiac arrhythmias.

DISCLOSURE OF THE INVENTION

According to the invention there is provided compounds of formula I,

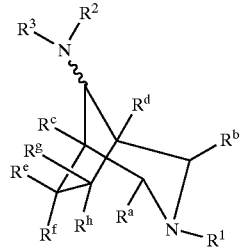

I wherein
the wavy bond represents optional endo- or exo-stereochemistry;
one of $R^1$ and $R^2$ represents $R^{1a}$ and the other represents a fragment of the formula Ia,

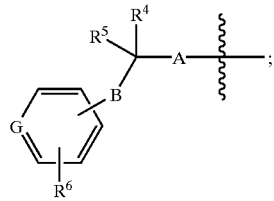

Ia $R^{1a}$ represents $C_{1-12}$ alkyl (optionally substituted and/or terminated by one or more groups selected from halo, cyano, nitro, aryl, $Het^1$, —$C(O)R^{7a}$, —$OR^{7b}$, —$N(R^8)$ $R^{7c}$, —$C(O)XR^9$, —$C(O)N(R^{10})R^{7d}$ and —$S(O)_2R^{11}$), $Het^2$, —$C(O)R^{7a}$, —$C(O)XR^9$, —$C(O)N(R^{10})R^{7d}$ or —$S(O)_2R^{11}$;

$R^{7a}$ to $R^{7d}$ independently represent, at each occurrence when used herein, H, $C_{1-6}$ alkyl (optionally substituted and/or terminated by one or more substituents selected from —OH, $C_{1-6}$alkoxy, halo, cyano, nitro, aryl, $Het^3$ and —$NHC(O)R^{12}$), aryl or $Het^4$, or $R^{7d}$, together with $R^{10}$, represents $C_{3-6}$ alkylene (which alkylene group is optionally interrupted by an O atom and/or is optionally substituted by one or more $C_{1-3}$ alkyl groups);

$R^{12}$ represents H, $C_{1-4}$ alkyl (optionally substituted and/or terminated by one or more substituents selected from halo, cyano, aryl and —$NHC(O)R^{13}$) or aryl;

$R^{13}$ represents H, $C_{1-4}$ alkyl or aryl;

$R^8$ represents H, $C_{1-6}$ alkyl (optionally substituted and/or terminated by one or more substituents selected from —OH, halo, cyano, nitro and aryl), aryl, —$C(O)R^{14a}$ or —$C(O)OR^{14b}$;

$R^{14a}$ and $R^{14b}$ represent $C_{1-6}$ alkyl (optionally substituted and/or terminated by one or more substituents selected from —OH, halo, cyano, nitro and aryl) or aryl, or $R^{14a}$ represents H;

X represents O or S;

$R^9$ represents, at each occurrence when used herein, $C_{1-12}$ alkyl (optionally substituted and/or terminated by one or more substituents selected from —OH, halo, cyano, nitro, aryl, $C_{1-4}$ alkoxy, —SO$_2$R$^{15}$ and Het$^5$);

$R^{15}$ represents $C_{1-6}$ alkyl or aryl;

$R^{10}$ represents, at each occurrence when used herein, H, $C_{1-12}$ alkyl, $C_{1-6}$ alkoxy (which latter two groups are optionally substituted and/or terminated by one or more substituents selected from —OH, halo, cyano, nitro, $C_{1-4}$ alkyl and $C_{1-4}$ alkoxy), —D-aryl, —D-aryloxy, —D—Het$^6$, —D—N(H)C(O)R$^{16a}$, —D—S(O)$_2$R$^{17a}$, —D—C(O)R$^{16b}$, —D—C(O)OR$^{17b}$, —D—C(O)N(R$^{16c}$)R$^{16d}$, or $R^{10}$, together with $R^{7d}$, represents $C_{3-4}$ alkylene (which alkylene group is optionally interrupted by an O atom and/or is optionally substituted by one or more $C_{1-3}$ alkyl groups);

$R^{16a}$ to $R^{16d}$ independently represent H, $C_{1-6}$ alkyl (optionally substituted and/or terminated by one or more substituents selected from —OH, halo, cyano, nitro and aryl), aryl,) or $R^{16c}$ and $R^{16d}$ together represent $C_{3-6}$ alkylene;

$R^{17a}$ and $R^{17b}$ independently represent $C_{1-4}$ alkyl (optionally substituted and/or terminated by one or more substituents selected from —OH, halo, cyano, nitro and aryl) or aryl;

D represents a direct bond or $C_{1-6}$ alkylene;

$R^{11}$ represents, at each occurrence when used herein, $C_{1-6}$ alkyl (optionally substituted and/or terminated by one or more substituents selected from —OH, halo, cyano, nitro and aryl), aryl or Het$^7$;

$R^4$ represents H, halo, $C_{1-6}$ alkyl, —OR$^{18}$, —E—N(R$^{19}$)R$^{20}$ OR together with $R^5$, represents =O;

$R^5$ represents H, $C_{1-6}$ alkyl or, together with $R^4$, represents =O;

$R^{18}$ represents H, $C_{1-6}$ alkyl, —E-aryl, —E—Het$^8$, —C(O)R$^{21a}$, —C(O)OR$^{21b}$ or —C(O)N(R$^{22a}$)R$^{22b}$;

$R^{19}$ represents H, $C_{1-6}$ alkyl, —E-aryl, —E—Het$^8$, —C(O)R$^{21a}$, —C(O)OR$^{21b}$, —S(O))$_2$R$^{21c}$, —[C(O)]$_p$N(R$^{22a}$)R$^{22b}$ or —C(NH)NH$_2$;

$R^{20}$ represents H, $C_{1-6}$ alkyl, —E-aryl or —C(O)R$^{21d}$;

$R^{21a}$ to $R^{21d}$ independently represent, at each occurrence when used herein, $C_{1-6}$ alkyl (optionally substituted and/or terminated by one or more substituents selected from halo, aryl and Het$^9$), aryl, Het$^{10}$, or $R^{21a}$ and $R^{21d}$ independently represent H;

$R^{22d}$ and $R^{22b}$ independently represent, at each occurrence when used herein, H or $C_{1-6}$ alkyl (optionally substituted and/or terminated by one or more substituents selected from halo, aryl and Het$^{11}$), aryl, Het$^{12}$, or together represent $C_{3-6}$ alkylene, optionally interrupted by an O atom;

E represents, at each occurrence when used herein, a direct bond or $C_{1-4}$ alkylene;

p represents 1 or 2;

Het$^1$ to Het$^{12}$ independently represent, at each occurrence when used herein, five- to twelve-membered heterocyclic groups containing one or more heteroatoms selected from oxygen, nitrogen and/or sulfur, which groups are optionally substituted by one or more substituents selected from —OH, oxo, halo, cyano, nitro, $C_{1-6}$ alkyl, $C_{1-6}$ alkoxy aryl, aryloxy, —N(R$^{23a}$)R$^{23b}$, —C(O)R$^{23c}$, —C(O)OR$^{23d}$, —C(O)N(R$^{23e}$)R$^{23f}$, —N(R$^{23g}$)C(O)R$^{23h}$ and —N(R$^{23i}$)S(O)$_2$R$^{23j}$;

$R^{23a}$ to $R^{23j}$ independently represent $C_{1-6}$ alkyl, aryl or $R^{23a}$ to $R^{23i}$ independently represent H;

A represents a direct bond, —J—, —J—N(R$^{24}$)— or —J—O— (in which latter two groups, N(R$^{24}$)— or O— is attached to the carbon atom bearing $R^4$ and $R^5$);

B represents —Z—, —Z—N(R$^{25}$)—, —N(R$^{25}$)—Z—, —Z—S(O)$_{11}$—, —Z—O— (in which latter two groups, Z is attached to the carbon atom bearing $R^4$ and $R^5$), —N(R$^{25}$)C(O)O—Z—, (in which latter group, —N(R$^{25}$) is attached to the carbon atom bearing $R^9$ and $R^{10}$) or —C(O)N(R$^{25}$)— (in which latter group, —C(O) is attached to the carbon atom bearing $R^4$ and $R^5$);

J represents $C_{1-6}$ alkylene optionally substituted by one or more substituents selected from —OH, halo and amino;

Z represents a direct bond or $C_{1-4}$ alkylene;

$R^{24}$ and $R^{25}$ independently represent H or $C_{1-6}$ alkyl;

G represents CH or N;

$R^6$ represents one or more optional substituents selected from —OH, cyano, halo, nitro, $C_{1-6}$ alkyl (optionally terminated by —N(H)C(O)OR$^{26a}$), $C_{1-6}$ alkoxy N—, —N(R$^{27a}$)R$^{27b}$, —C(O)R$^{27c}$, —C(O)OR$^{27d}$, —C(O)N(R)R$^{27e}$)R$^{27f}$, —N(R$^{27g}$)C(O)R$^{27h}$, —N(R$^{27i}$)C(O)N(R$^{27j}$)R$^{27k}$, —N(R$^{27m}$)S(O)$_2$R$^{26b}$, —S(O)$_n$R$^{26c}$, and/or —OS(O)$_2$R$^{26d}$;

$R^{26a}$ to $R^{26d}$ independently represent $C_{1-6}$ alkyl;

$R^{27a}$ to $R^{27m}$ independently represent H or $C_{1-6}$ alkyl;

n represents, at each occurrence, 0, 1 or 2; and $R^a$ to $R^h$ and $R^3$ independently represent H or $C_{1-4}$ alkyl;

wherein each aryl and aryloxy group, unless otherwise specified, is optionally substituted;

or a pharmaceutically acceptable derivative thereof;

provided that (a) when A represents —J—N(R$^{24}$)— or —J—O—, then:
  (i) J does not represent $C_1$ alkylene; and
  (ii) B does not represent —N(R$^{25}$)—, —N(R$^{25}$)—Z— (in which latter group N(R$^{25}$) is attached to the carbon atom bearing $R^4$ and $R^5$), —S(O)$_n$—, —O— or —N(R$^{25}$)C(O)O—Z— when $R^4$ and $R^5$ do not together represent =O;

(b) when $R^4$ represents —OR$^{18}$ or —N(R$^{19}$)(R$^{20}$), then:
  (i) A does not represent —J—N(R$^{24}$)— or —J—O—; and
  (ii) B does not represent —N(R$^{25}$)—, —N(R$^{25}$)—Z— (in which latter group N(R$^{25}$) is attached to the carbon atom bearing $R^4$ and $R^5$), —S(O)$_n$—, —O— or —N(R$^{25}$)C(O)O—Z—;

(c) when A represents a direct bond, then $R^4$ and $R^5$ do not together represent =O; and (d) the compound is not: (±) (8β)-4-amino-5-chloro-2-methoxy-N-(3-benzyl-3-azabicyclo-[3.2.1]oct-8-yl)benzamide; (S)-N-(3-benzyl-3-azabicyclo[3.2.1]oct-8-yl)-4-amino-5-chloro-2-(1-methyl-2-butynyl)oxybenzamide; or (S)-N-(3-benzyl-3-azabicyclo[3.2.1]oct-8-yl)-4-amino-5-chloro-2-(1-methyl-2-butynyl)oxybenzamide hydrochloride;

which compounds are referred to hereinafter as "the compounds of the invention".

Unless otherwise specified, alkyl groups and alkoxy groups as defined herein may be straight-chain or, when there is a sufficient number (i.e. a minimum of three) of carbon atoms, be branched-chain and/or cyclic. Further, when there is a sufficient number (i.e. a minimum of four)

of carbon atoms, such alkyl and alkoxy groups may also be part cyclic/acyclic. Such alkyl and alkoxy groups may also be saturated or, when there is a sufficient number (i.e. a minimum of two) of carbon atoms, be unsaturated and/or interrupted by one or more oxygen and/or sulfur atoms. Unless otherwise specified, alkyl and alkoxy groups may also be substituted by one or more halo, and especially fluoro, atoms.

Unless otherwise specified, alkylene groups as defined herein may be straight-chain or, when there is a sufficient number (i.e. a minimum of two) of carbon atoms, be branched-chain. Such alkylene chains may also be saturated or, when there is a sufficient number (i.e. a minimum of two) of carbon atoms, be unsaturated and/or interrupted by one or more oxygen and/or sulfur atoms. Unless otherwise specified, alkylene groups may also be substituted by one or more halo atoms.

The term "aryl", when used herein, includes $C_{6-10}$ aryl groups such as phenyl, naphthyl and the like. The term "aryloxy", when used herein includes $C_{6-10}$ aryloxy groups such as phenoxy, naphthoxy and the like. For the avoidance of doubt, aryloxy groups referred to herein are attached to the rest of the molecule via the O-atom of the oxy-group. Unless otherwise specified, aryl and aryloxy groups may be substituted by one or more substituents including —OH, halo, $Het^1$, cyano, nitro, $C_{1-6}$ alkyl, $C_{1-6}$ alkoxy, $N(R^{27a})R^{27b}$, —C(O)$R^{27c}$, —C(O)O$R^{27d}$, —C(O)N($R^{27e}$)$R^{27f}$, —N($R^{27g}$)C(O)$R^{27h}$, —N($R^{27m}$)S(O)$_2R^{26b}$, —S(O)$_nR^{26c}$, and/or —OS(O)$_2R^{26d}$ (wherein $Het^1$, $R^{26b}$ to $R^{26d}$, $R^{27a}$ to $R^{27m}$ and n are as hereinbefore defined). When substituted, aryl and aryloxy groups are preferably substituted by between one and three substituents. When aryl is substituted by one or more $Het^1$ group(s), any aryl group(s) that said $Het^1$ group(s) may be substituted with may not itself (themselves) be substituted by any $Het^1$ group(s).

The term "halo", when used herein, includes fluoro, chloro, bromo and iodo. Het ($Het^1$, $Het^2$, $Het^3$, $Het^4$, $Het^5$, $Het^6$, $Het^7$, $Het^8$, $Het^9$, $Het^{10}$, $Het^{11}$ and $Het^{12}$) groups that may be mentioned include those containing 1 to 4 heteroatoms (selected from the group oxygen, nitrogen and/or sulfur) and in which the total number of atoms in the ring system are between five and twelve. Het ($Het^1$, $Het^2$, $Het^3$, $Het^4$, $Het^5$, $Het^6$, $Het^7$, $Het^8$, $Het^9$, $Het^{10}$, $Het^{11}$ and $Het^{12}$) groups may be fully saturated, wholly aromatic, partly aromatic and/or bicyclic in character. Heterocyclic groups that may be mentioned include benzodioxanyl, benzodioxepanyl, benzodioxolyl, benzofuranyl, benzofurazanyl, benzimidazolyl, benzomorpholinyl, benzothiophenyl, chromanyl, cinnolinyl, dioxanyl, furanyl, hydantoinyl, imidazolyl, imidazo[1,2-a]pyridinyl, indolyl, isoquinolinyl, isoxazolyl, maleimido, morpholinyl, oxazolyl, phthalazinyl, piperazinyl, piperidinyl, purinyl, pyranyl, pyrazinyl, pyrazolyl, pyridinyl, pyrimindinyl, pyrrolidinonyl, pyrrolidinyl, pyrrolinyl, pyrrolyl, quinazolinyl, quinolinyl, 3-sulfolenyl, tetrahydropyranyl, tetrahydrofuranyl, thiazolyl, thienyl, thiochromanyl, triazolyl and the like. Values of $Het^1$ that may be mentioned include maleimido and piperazinyl. Values of $Het^2$ that may be mentioned include thiazolyl. Values of $Het^3$ that may be mentioned include hydantoinyl. Values of $Het^4$ that may be mentioned include benzodioxanyl, benzofurazanyl, pyrazolyl and pyrrolyl. Values of $Het^5$ that may be mentioned include morpholinyl, piperazinyl and pyridinyl. Values of $Het^6$ that may be mentioned include isoxazolyl and tetrahydropyranyl. Values of $Het^7$ that may be mentioned include imidazolyl, pyrazolyl, 3-sulfolenyl and thiazolyl. Substituents on Het ($Het^1$, $Het^2$, $Het^3$, $Het^4$, $Het^5$, $Het^6$, $Het^7$, $Het^8$, $Het^9$, $Het^{10}$, $Het^{11}$ and $Het^{12}$) groups may, where appropriate, be located on any atom in the ring system including a heteroatom. The point of attachment of Het ($Het^1$, $Het^2$, $Het^3$, $Het^4$, $Het^5$, $Het^6$, $Het^7$, $Het^8$, $Het^9$, $Het^{10}$, $Het^{11}$ and $Het^{12}$) groups may be via any atom in the ring system including (where appropriate) a heteroatom, or an atom on any fused carbocyclic ring that may be present as part of the ring system. Het ($Het^1$, $Het^2$, $Het^3$, $Het^4$, $Het^5$, $Het^6$, $Het^7$, $Het^8$, $Het^9$, $Het^{10}$, $Het^{11}$ and $Het^{12}$) groups may also be in the N— or S-oxidised form.

Pharmaceutically acceptable derivatives include salts and solvates. Salts which may be mentioned include acid addition salts. Pharmaceutically acceptable derivatives also include, at the 3-azabicyclo[3.2.1]octane or (when G represents N) pyridyl nitrogens, $C_{1-4}$alkyl quaternary ammonium salts and N-oxides, provided that when a N-oxide is present:

(a) no Het ($Het^1$, $Het^2$, $Het^3$, $Het^4$, $Het^5$, $Het^6$, $Het^7$, $Het^8$, $Het^9$, $Het^{10}$, $Het^{11}$ and $Het^{12}$) group contains an unoxidised S-atom; and/or (b) n does not represent 0 when B represents —Z—S(O)$_n$—.

The compounds of the invention may exhibit tautomerism. All tautomeric forms and mixtures thereof are included within the scope of the invention.

The compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

According to a further aspect of the invention, there is provided compounds of formula I as hereinbefore defined with the additional proviso that when $Het^1$ or $Het^4$ represents piperazin-1-yl, then the piperazinyl group does not bear a 3,4-dichlorophenyl substituent.

According to a further aspect of the invention, there is provided compounds of formula I, as hereinbefore defined, but without proviso (d) and with the additional provisos that:

(i) when $R^1$ represents a fragment of formula Ia in which A represents J, B represents Z, and $R^4$ and $R^5$ represent H or $C_{1-6}$ alkyl; then $R^2$ does not represent $C_{1-10}$ alkyl substituted by $Het^1$ or —C(O)$Het^4$ (wherein $Het^1$ or $Het^4$ represents homopiperazin-1-yl, piperazin-1-yl or 1-imidazolidinyl, which homopiperazinyl, piperazinyl or imidazolidinyl group is substituted in the 4-, 4- or 3-position (respectively) by —C(O)$R^{23c}$ (in which $R^{23c}$ represents aryl) and (at one of the ring C-atoms) by aryl, and which homopiperazinyl, piperazinyl or imidazolidinyl group is further optionally substituted by $C_{1-6}$ alkyl), and which $C_{1-10}$ alkyl group is further optionally substituted by one substituent selected from optionally substituted phenyl, cyano, —O$R^{7b}$, —N($R^8$)$R^{7c}$, —C(O)O$R^9$, —C(O)N($R^{10}$)$R^{7d}$ (wherein $R^{7b}$, $R^{7c}$, $R^{7d}$, $R^9$ and $R^{10}$ represent H, $C_{1-6}$ alkyl or optionally substituted phenyl), imidazolyl or optionally substituted indolyl;

(ii) when $R^a$ to $R^h$ and $R^3$ all represent H; and $R^1$ represents a fragment of formula Ia in which the group —A—C(R$^4$)(R$^5$)—B— represents C$_{1-3}$ alkylene, G represents CH and R$^6$ is absent; then R$^2$ does not represent —C(O)R$^{7a}$, wherein R$^{7a}$ represents phenyl substituted in the 2-position by C$_{3-6}$ alkynyloxy (optionally interrupted by oxygen), in the 4-position by —N(R$^{27a}$)R$^{27b}$ or —N(H)C(O)R$^{27h}$ (wherein R$^{27h}$ represents C$_{1-6}$ alkyl), and in the 5-position by halo; and (iii) when R$^3$ represents H; and R$^1$ represents a fragment of formula Ia in which the group —A—C(R$^4$)(R$^5$)—B— represents C$_{1-2}$ alkylene, G represents CH and R$^6$ represents one or two substituents selected from C$_{1-6}$ alkyl (optionally interrupted by oxygen), C$_{1-4}$ alkoxy, CF$_3$, halo, nitro, —C(O)OH or —C(O)O—C$_{1-6}$ alkyl); then R$^2$ does not represent —C(O)R$^{7a}$, wherein R$^{7a}$ represents phenyl substituted in the 2-position by C$_{1-6}$ alkoxy, in the 4-position by —NH$_2$ or —N(H)C(O)R$^{27h}$ (wherein R$^{27h}$ represents C$_{1-6}$ alkyl), and in the 5-position by halo or —SR$^{26c}$.

Abbreviations are listed at the end of this specification.

Preferred compounds of the invention include those in which:

R$^{1a}$ represents C$_{1-8}$ alkyl (optionally substituted and/or terminated by one or more groups selected from halo, optionally substituted aryl, Het$^1$, —C(O)R$^{7a}$, —OR$^{7b}$, —N(R$^8$)R$^{7c}$, —C(O)XR$^9$, —C(O)N(R$^{10}$)R$^{7d}$ and —S(O)$_2$R$^{11}$), Het$^2$, —C(O)R$^{7a}$, —C(O)XR$^9$, —C(O)N(R$^{10}$)R$^{7d}$ or —S(O)$_2$R$^{11}$;

R$^{7a}$ to R$^{7d}$ independently represent, at each occurrence, H, C$_{1-5}$ alkyl (optionally substituted and/or terminated by one or more substituents selected from —OH, C$_{1-4}$ alkoxy, halo, cyano, optionally substituted aryl, Het$^3$ and —NHC(O)R$^{12}$), optionally substituted aryl or Het$^4$, or R$^{7d}$, together with R$^{10}$, represents C$_{3-6}$ alkylene;

R$^{12}$ represents C$_{1-3}$ alkyl (optionally substituted and/or terminated by one or more substituents selected from halo, aryl and —NHC(O)R$^{13}$) or optionally substituted aryl;

R$^{13}$ represents C$_{1-3}$ alkyl or aryl;

R$^8$ represents H, C$_{1-4}$ alkyl (optionally substituted and/or terminated by optionally substituted aryl), optionally substituted aryl, —C(O)R$^{14a}$, or —C(O)OR$^{14b}$;

R$^{14a}$ and R$^{14b}$ represent C$_{1-4}$ alkyl (optionally substituted and/or terminated by aryl) or aryl;

R$^9$ represents, at each occurrence, C$_{1-8}$ alkyl (optionally substituted and/or terminated by one or more substituents selected from —OH, halo, cyano, optionally substituted aryl, C$_{1-4}$ alkoxy, —SO$_2$R$^{15}$ and Het$^5$);

R$^{15}$ represents C$_{1-4}$ alkyl or aryl;

R$^{10}$ represents, at each occurrence, H, C$_{1-8}$ alkyl, C$_{1-4}$ alkoxy (which latter two groups are optionally substituted and/or terminated by one or more substituents selected from —OH, halo and C$_{1-4}$ alkoxy), —D-(optionally substituted aryl), —D-aryloxy, —D-Het$^6$, —D—S(O)$_2$R$^{17a}$, or R$^{10}$, together with R$^{7d}$, represents C$_{3-6}$ alkylene;

R$^{17a}$ represents C$_{1-4}$ alkyl or optionally substituted aryl;

D represents a direct bond or C$_{1-3}$ alkylene;

R$^{11}$ represents, at each occurrence, C$_{1-5}$ alkyl (optionally substituted and/or terminated by one or more halo atoms), optionally substituted aryl or Het$^7$;

R$^4$ represents H, halo, C$_{1-2}$ alkyl, —OR$^{18}$ or —E—N(R$^{19}$)R$^{20}$;

R$^5$ represents H, or C$_{1-2}$ alkyl;

R$^{18}$ represents H, C$_{1-4}$ alkyl, —E-(optionally substituted aryl) or —E—Het$^8$;

R$^{19}$ represents H, C$_{1-4}$ alkyl, —E-aryl, —E—Het$^8$, —C(O)R$^{21a}$ or —C(O)OR$^{21b}$;

R$^{20}$ represents H, C$_{1-4}$ alkyl or —E-aryl;

R$^{21a}$ and R$^{21b}$ independently represent C$_{1-4}$ alkyl (optionally substituted and/or terminated by one or more substituents selected from halo and aryl) or aryl;

E represents, at each occurrence, a direct bond or C$_{1-2}$ alkylene;

Het$^1$ to Het$^8$ independently represent, at each occurrence, fully saturated, wholly aromatic, partly aromatic and/or bicyclic five- to twelve-membered heterocyclic groups containing between one and four heteroatoms selected from oxygen, nitrogen and/or sulfur, which groups are optionally substituted by one or more substituents selected from oxo, halo, cyano, C$_{1-5}$ alkyl, C$_{1-4}$ alkoxy, —N(R$^{23a}$)R$^{23b}$, —C(O)R$^{23c}$, —C(O)OR$^{23d}$, —C(O)N(R$^{23e}$)R$^{23f}$, and —N(R$^{23g}$)C(O)R$^{23h}$;

R$^{23a}$ to R$^{23h}$ independently represent H or C$_{1-3}$ alkyl;

A represents a direct bond or —J—;

B represents —Z—, —Z—N(R$^{25}$)—, —Z—S(O)$_n$— or —Z—O— (in which latter three groups, Z is attached to the carbon atom bearing R$^4$ and R$^5$);

J represents C$_{1-5}$ alkylene optionally substituted by one or more substituents selected from —OH, halo and amino;

Z represents a direct bond or C$_{1-3}$ alkylene;

n represents 0 or 2;

R$^{25}$ represents H or C$_{1-4}$ alkyl;

G represents CH;

R$^6$ represents one or more optional substituents selected from —OH, cyano, halo, nitro, C$_{1-3}$ alkyl (optionally terminated by —N(H)C(O)OR$^{26a}$) and C$_{1-4}$ alkoxy;

R$^{26a}$ represents C$_{1-4}$ alkyl;

R$^3$ represents H or C$_{1-2}$ alkyl;

R$^a$ to R$^h$ all represent H.

More preferred compounds of the invention include those in which:

R$^{1a}$ represents linear, branched or part cyclic/acyclic C$_{1-6}$ alkyl (which alkyl group is (i) optionally interrupted by one or more oxygen atoms; and/or (ii) optionally substituted and/or terminated by one or more groups selected from phenyl (optionally substituted by one or more substituents selected from halo and methoxy), Het$^1$ (optionally substituted by —C(O)R$^{23c}$), —C(O)R$^{7a}$, —OR$^{7b}$, —C(O)N(H)R$^{10}$ and —S(O)$_2$R$^{11}$), Het$^2$, —C(O)R$^{7a}$, —C(O)OR$^9$, —C(O)N(H)R$^{10}$ or —S(O)$_2$R$^{11}$;

R$^{7a}$ and R$^{7b}$ independently represent, at each occurrence, H, linear or branched C$_{1-5}$ alkyl (which alkyl group is (i) optionally unsaturated; and/or (ii) optionally substituted and/or terminated by one or more substituents selected from —OH, C$_{1-2}$ alkoxy, Het$^3$ and —NHC(O)R$^{12}$), phenyl (optionally substituted by halo or methoxy) or Het$^4$ (optionally substituted by C$_{1-4}$ alkyl);

R$^{12}$ represents C$_{1-2}$ alkyl (optionally substituted and/or terminated by —NHC(O)R$^{13}$);

R$^{13}$ represents C$_{1-2}$alkyl;

R$^9$ represents, at each occurrence, linear, branched or part cyclic/acyclic C$_{1-6}$ alkyl (which alkyl group is (i) optionally unsaturated; (ii) optionally interrupted by one or more oxygen atoms; and/or (iii) optionally substituted and/or terminated by one or more substituents selected from —OH, cyano, $C_{1-2}$ alkoxy, —$SO_2R^{15}$ and $Het^5$ (optionally substituted by —C(O)$R^{23c}$));

$R^{15}$ represents $C_{1-2}$ alkyl;

$R^{10}$ represents, at each occurrence, H, linear, branched or part cyclic/acyclic $C_{1-7}$ alkyl, (which alkyl group is (i) optionally interrupted by one or more oxygen atoms; and/or (ii) optionally substituted and/or terminated by $C_{1-2}$ alkoxy), phenyl (optionally substituted by one or more substituents selected from halo, methoxy, $Het^1$ and $SR^{26c}$), $Het^6$ (optionally substituted by one or more $C_{1-2}$ alkyl groups) or —$S(O)_2R^{17a}$;

$R^{26c}$ represents $C_{1-2}$ alkyl optionally substituted by one or more halo atoms;

$R^{17a}$ represents phenyl (optionally substituted by $C_{1-2}$ alkyl);

$R^{11}$ represents, at each occurrence, linear, branched or part cyclic/acyclic $C_{1-5}$ alkyl, phenyl (optionally substituted by one or more substituents selected from nitro, methoxy and $N(H)C(O)R^{27h}$) or $Het^7$ (optionally substituted by one or more substituents selected from halo, $C_{1-2}$ alkyl and $N(H)C(O)R^{23h}$);

$R^4$ represents H, —$OR^{18}$ or —$N(H)R^{19}$;

$R^5$ represents H;

$R^{18}$ represents H or phenyl (optionally substituted by one or more substituents selected from OH and methoxy);

$R^{19}$ represents H or —$C(O)OR^{21b}$;

$R^{21b}$ represents $C_{1-2}$ alkyl;

$Het^1$ to $Het^8$ independently represent, at each occurrence, fully saturated, wholly aromatic, partly aromatic and/or bicyclic five- to twelve-membered heterocyclic groups containing between one and four heteroatoms selected from oxygen, nitrogen and/or sulfur;

$R^{23c}$, $R^{23h}$ and $R^{27h}$ independently represent, at each occurrence, $C_{1-2}$ alkyl;

A represents a direct bond or —J—;

B represents —Z—, —Z—N(H)—, —Z—$SO_2$— or —Z—O— (in which latter three groups, Z is attached to the carbon atom bearing $R^4$ and $R^5$);

J represents $C_{1-3}$ alkylene optionally substituted by —OH or amino;

Z represents a direct bond or $C_{1-2}$ alkylene;

$R^6$ represents one or two cyano groups;

$R^3$ represents H or methyl.

Particularly preferred compounds of the invention include those in which:

$R^{1a}$ represents —$C(O)R^{7a}$, —$C(O)N(H)R^{10}$ or —$S(O)_2R^{11}$;

$R^{10}$ represents linear, branched or part cyclic/acyclic $C_{1-5}$ alkyl, (which alkyl group is optionally interrupted by one or more oxygen atoms);

$R^4$ represents H, —OH or —$NH_2$;

A represents a direct bond or —J—;

B represents —Z—N(H)— or —Z—O— (in which latter two groups, Z is attached to the carbon atom bearing $R^4$ and $R^5$);

J represents $C_{1-3}$ alkylene;

$R^6$ represents a cyano group in the position para to where B is attached;

$R^3$ represents methyl.

Preferred compounds of the invention include the compounds of the Examples disclosed hereinafter.

Preparation

According to the invention there is also provided a process for the preparation of compounds of formula I which comprises:

(a) reaction of a compound of formula IIA or IIB,

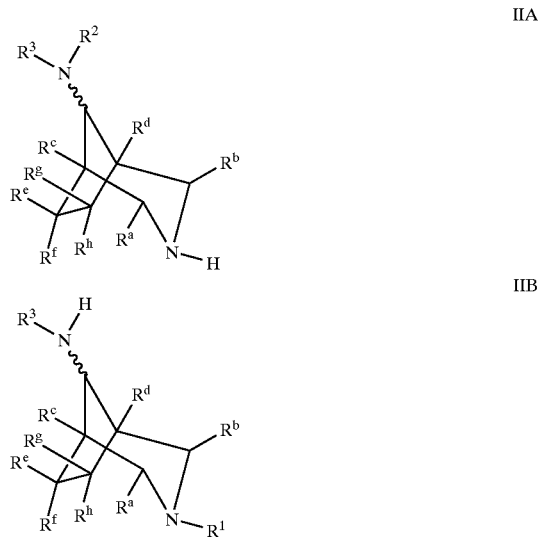

wherein $R^1$, $R^2$, $R^3$ and $R^a$ to $R^h$ are as hereinbefore defined, with a compound of formula III,

wherein $R^{28}$ represents either $R^1$ or $R^2$ (as appropriate), $L^1$ represents a leaving group such as halo, alkanesulfonate, perfluoroalkanesulfonate, arenesulfonate, —OC(O)$XR^9$, imidazole or $R^{29}$O— (wherein $R^{29}$ represents, for example, $C_{1-10}$ alkyl or azyl, which groups are optionally substituted by one or more halo or nitro groups) and $R^1$, $R^2$ and $R^9$ are as hereinbefore defined, for example at between room and reflux temperature in the presence of a suitable base (e.g. triethylamine or potassium carbonate) and an appropriate organic solvent (e.g. dichloromethane, chloroform, acetonitrile, N,N-dimethylformamide, dimethylsulfoxide, THF, toluene or mixtures thereof);

(b) for compounds of formula I in which $R^1$ or $R^2$ (as appropriate) represents —$C(O)XR^9$ or —$C(O)N(R^{10})R^{7d}$, reaction of a compound of formula IVA or IVB,

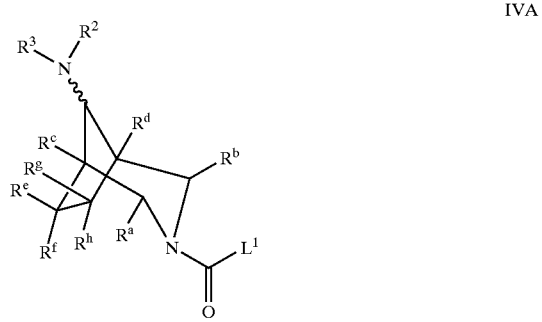

-continued

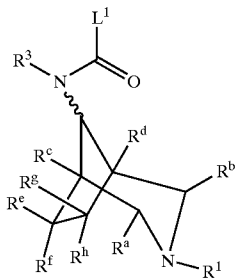
IVB wherein $R^3$, $R^a$ to $R^h$ and $L^1$ are as hereinbefore defined and $R^1$ and $R^2$ represent a fragment of formula Ia, as hereinbefore defined, with a compound of formula V,

V wherein $R^{30}$ represents $-XR^9$ or $-N(R^{10})R^{7d}$ and $R^{7d}$, $R^9$, $R^{10}$ and X are as hereinbefore defined, for example under conditions described hereinbefore (process step (a));

(c) for compounds of formula I in which $R^1$ or $R^2$ (as appropriate) represents $-C(O)N(H)R^{10}$, reaction of a compound of formula IIA or IIB (as appropriate), as hereinbefore defined (except that $R^1$ or $R^2$ (as appropriate) does not represent $R^{1a}$), with a compound of formula VI,

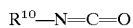
VI wherein $R^{10}$ is as hereinbefore defined, for example at between 0° C. and reflux temperature in the presence of an appropriate organic solvent (e.g. dichloromethane), or via solid phase synthesis under conditions known to those skilled in the art;

(d) for compounds of formula I in which $R^1$ or $R^2$ (as appropriate) represents a fragment of formula Ia in which A represents $CH_2$ and $R^4$ represents —OH or $-N(H)R^{19}$, reaction of a compound of formula IIA or IIB, as hereinbefore defined (except that $R^1$ or $R^2$ (as appropriate) does not represent a fragment of formula Ia), with a compound of formula VII,

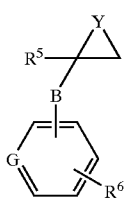
VII wherein Y represents O or $N(R^{19})$ and $R^5$, $R^6$, $R^{19}$, B and G are as hereinbefore defined, for example at elevated temperature (e.g. 60° C. to reflux) in the presence of a suitable solvent (e.g. a lower alkyl alcohol (e.g. IPA), acetonitrile, or a mixture of a lower alkyl alcohol and water);

(e) for compounds of formula I in which, in the fragment of formula Ia, B represents —Z—O—, reaction of a compound of formula VIIIA or VIIIB,

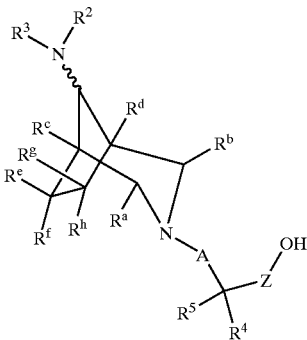
VIIIA

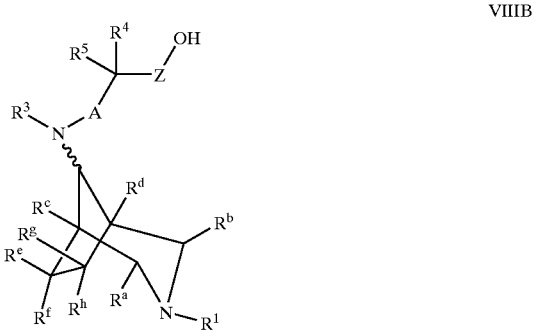
VIIIB wherein $R^3$, $R^4$, R $R^a$ to $R^h$, A and Z are as hereinbefore defined, and $R^1$ and $R^2$ (as appropriate) are as hereinbefore defined (except that, in each case, they do not represent a fragment of formula Ia), with a compound of formula IX,

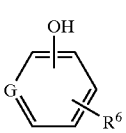
IX wherein $R^6$ and G are as hereinbefore defined, for example under Mitsunobu-type conditions e.g. at between ambient (e.g. 25° C.) and reflux temperature in the presence of a tertiary phosphine (e.g. tributylphosphine or triphenylphosphine), an azodicarboxylate derivative (e.g. diethylazodicarboxylate or 1,1'-(azodicarbonyl)dipiperidine) and an appropriate organic solvent (e.g. dichloromethane or toluene);

(f) for compounds of formula I in which G represents N and B represents —Z—O—, reaction of a compound of formula VIIIA or VIIIB, as hereinbefore defined, with a compound of formula X,

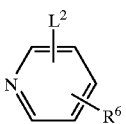
X wherein $L^2$ represents a leaving group such as halo, alkanesulfonate, perfluoroalkanesulfonate or arenesulfonate, and $R^6$ is as hereinbefore defined, for example at between 10° C. and reflux temperature in the presence of a suitable base (e.g. sodium hydride) and an appropriate solvent (e.g. N,N-dimethylformamide);

(g) for compounds of formula I in which $R^4$ represents —$OR^{18}$, in which $R^{18}$ represents $C_{1-6}$ alkyl, —E-aryl or —E—$Het^8$, reaction of a corresponding compound of formula I in which $R^4$ represents OH with a compound of formula X), $$R^{18a}OH \qquad XI$$

wherein $R^{18a}$ represents $C_{1-6}$ alkyl, —E-aryl or —E—$Het^8$, and E and $Het^8$ are as hereinbefore defined, for example under Mitsunobu-type conditions (e.g. as described hereinbefore in process step (e));

(h) for compounds of formula I in which $R^4$ represents —$OR^{18}$, in which $R^{18}$ represents $C_{1-6}$ alkyl, —E-aryl or —E—$Het^8$, reaction of a compound of formula XIIA or XIIB,

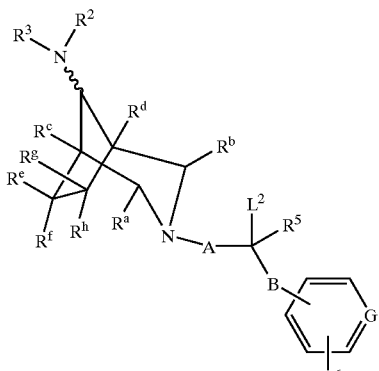

XIIA

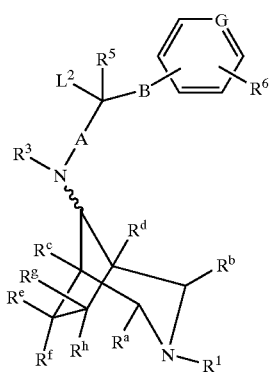

XIIB wherein $R^1$ or $R^2$ (as appropriate) represents $R^{7a}$, and $R^{1a}$, $R^3$, $R^5$, $R^6$, $R^a$ to $R^h$, A, B, G and $L^2$ are as hereinbefore defined, with a compound of formula XI, as hereinbefore defined, for example at between ambient (e.g. 25° C.) and reflux temperature, under Williamson-type conditions (i.e. in the presence of an appropriate base (e.g. KOH or NaH) and a suitable organic solvent (e.g. dimethylsulfoxide or N,Nimethylformamide)) (the skilled person will appreciate that certain compounds of formula XIIA and XIIB (e.g. those in which $L^2$ represents halo) may also be regarded as compounds of formula I as hereinbefore defined);

(i) for compounds of formula I in which $R^4$ represents —E—$NH_2$, reduction of a compound of formula XIIIA or XIIIB,

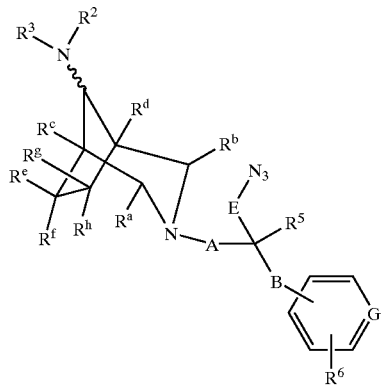

XIIIA

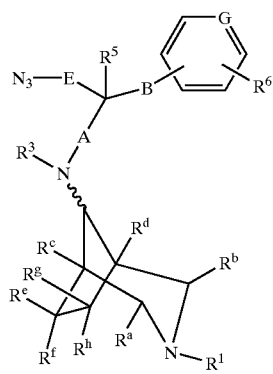

XIIIB wherein $R^1$ or $R^2$ (as appropriate) represents $R^{1a}$, and $R^{1a}$, $R^3$, $R^5$, $R^6$, $R^a$ to $R^h$, A, B, E and G are as hereinbefore defined, for example by hydrogenation at a suitable pressure in the presence of a suitable catalyst (e.g. palladium on carbon) and an appropriate solvent (e.g. a water-ethanol mixture);

(j) for compounds of formula I in which $R^4$ represents —E—$N(R^{19})R^{20}$, wherein $R^{19}$ represents $C_{1-6}$ alkyl, —E-aryl —E—$Het^8$, —$C(O)R^{21a}$, $C(O)OR^{21b}$, —$S(O)_2R^{21c}$ or —$C(O)N(R^{22a})R^{22b}$, reaction of a corresponding compound of formula I in which $R^4$ represents —E—$N(H)R^{20}$ with a compound of formula XIV, $$R^{19a}—L^1 \qquad XIV$$

wherein $R^{19a}$ represents $C_{1-6}$ alkyl, —E-aryl —E—$Het^8$, —$C(O)R^{21a}$, —$C(O)OR^{21b}$, —$S(O)_2R^{21c}$ or —$C(O)N(R^{22a})R^{22b}$, and $R^{21a}$, $R^{21b}$, $R^{21c}$, $R^{22a}$, $R^{22b}$, $Het^8$, E and $L^1$ are as hereinbefore defined, for example under conditions described hereinbefore (process step (a));

(k) for compounds of formula I in which $R^4$ represents —E—$N(R^{20})C(O)N(H)R^{22a}$, reaction of a corresponding compound of formula I in which $R^4$ represents —E—$N(H)R^{20}$ with a compound of formula XV, $$R^{22a}—N=C=O \qquad XV$$

wherein $R^{22a}$ is as hereinbefore defined, for example under conditions described hereinbefore (process step (c));

(l) for compounds of formula I in which $R^4$ represents —E—$N(H)[C(O)]_2NH_2$, reaction of a corresponding compound of formula I in which $R^4$ represents —E—$NH_2$ with oxalic acid diamide, for example at between −10 and 25° C. in the presence of a suitable coupling agent (e.g. 1-(3-dimethylaminopropyl)-3-ethylcarbodiimide), an appropriate activating agent (e.g. 1-hydroxybenzotriazole), a suitable base (e.g. triethylamine) and a reaction-inert solvent (e.g. N,N-dimethylformamide);

(m) for compounds of formula I in which $R^4$ represents —E—N(H)C(NH)NH$_2$, reaction of a corresponding compound of formula I in which $R^4$ represents —E—NH$_2$ with a compound of formula XVI, $$R^{29}O—C(=NH)NH_2 \qquad XVI$$

or an N-protected derivative thereof, wherein $R^{29}$ is as hereinbefore defined, for example at between room and reflux temperature, optionally in the presence of a suitable solvent (e.g. toluene) and/or an appropriate acidic catalyst (e.g. acetic acid at, for example, 10 mol %);

(n) for compounds of formula I in which $R^4$ represents —OR$^{18}$, in which $R^{18}$ represents —C(O)R$^{21a}$, —C(O)OR$^{21b}$ or —C(O)N(R$^{22a}$)R$^{22b}$, reaction of a corresponding compound of formula I in which $R^4$ represents —OH with a compound of formula XVII, $$R^{18b}—L^3 \qquad XVII$$

wherein $R^{18b}$ represents —C(O)R$^{21a}$, —C(O)OR$^{21b}$ or —C(O)N(R$^{22a}$)R$^{22b}$, $L^3$ represents a leaving group such as halo, p-nitrophenoxy, —OC(O)R$^{21a}$, —OC(O)OR$^{21b}$, —OH or imidazole and $R^{21a}$, $R^{21b}$, $R^{22a}$ and $R^{22b}$ are as hereinbefore defined, for example at between −10° C. and reflux temperature in the presence of a suitable base (e.g. triethylamine, pyridine or potassium carbonate), an appropriate organic solvent (e.g. THF, dichloromethane or acetonitrile) and (where appropriate) a suitable coupling agent (e.g. 1-(3-dimethylaminopropyl)-3-ethylcarbodiimide);

(o) for compounds of formula I in which $R^4$ represents H or —OH and $R^5$ represents H, reduction of a corresponding compound of formula I in which $R^4$ and $R^5$ together represent =O, in the presence of a suitable reducing agent and under appropriate reaction conditions; for example, for formation of compounds of formula I in which $R^4$ represents OH, reduction may be performed under mild reaction conditions in the presence of e.g. sodium borohydride and an appropriate organic solvent (e.g. THF); and for formation of compounds of formula I in which $R^4$ represents H, reduction may be performed either under Wolff-Kischner conditions known to those skilled in the art or by activating the relevant C=O group using an appropriate agent (such as tosylhydrazine) in the presence of a suitable reducing agent (e.g. sodium borohydride or sodium cyanoborohydride) and an appropriate organic solvent (e.g. a lower (e.g. $C_{1-6}$) alkyl alcohol);

(p) for compounds of formula I in which $R^4$ represents halo, substitution of a corresponding compound of formula I in which $R^4$ represents —OH, using an appropriate halogenating agent (e.g. for compounds in which $R^4$ represents fluoro, reaction with (diethylamino)sulfur trifluoride);

(q) for compounds of formula I in which $R^4$ and $R^5$ represent H, A represents —J—and B represents —N(R$^{25}$)Z— (wherein —N(R$^{25}$) is attached to the carbon atom bearing $R^4$ and $R^5$), reaction of a compound of formula XVIIIA or XVIIIB,

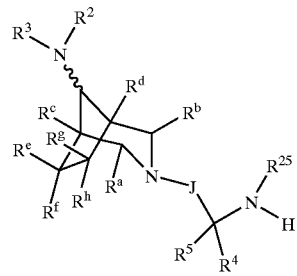

XVIIIA

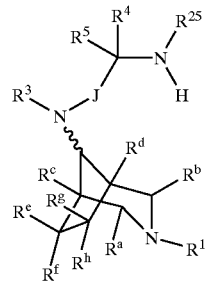

XVIIIB wherein $R^1$ or $R^2$ (as appropriate) represents $R^{1a}$, and $R^{1a}$, $R^3$, $R^4$, $R^5$, $R^{25}$ $R^a$ to $R^h$ and J are as hereinbefore defined, with a compound of formula XIX,

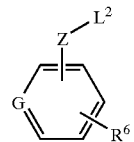

XIX wherein $R^6$, G. Z and $L^2$ are as hereinbefore defined, for example at elevated temperature (e.g. 40° C. to reflux) in the presence of a suitable organic solvent (e.g. acetonitrile);

(r) for compounds of formula I in which A represents $C_2$ alkylene and $R^4$ and $R^5$ together represent =O, reaction of a compound of formula IIA or IIB, as hereinbefore defined (except that $R^1$ or $R^2$ (as appropriate) does not represent a fragment of formula Ia), with a compound of formula XX,

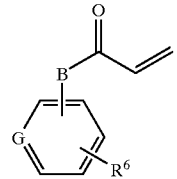

XX wherein B, G and $R^6$ are as hereinbefore defined, for example at between room and reflux temperature in the presence of a suitable base (e.g. triethylamine, potassium carbonate or tetrabutylammonium hydroxide) and an appropriate organic solvent (e.g. a lower alkyl (e.g. $C_{1-6}$) alcohol);

(s) for compounds of formula I in which $R^3$ represents H and $R^2$ represents unsubstituted $C_{1-4}$ alkyl, reaction of a compound of formula XXI,

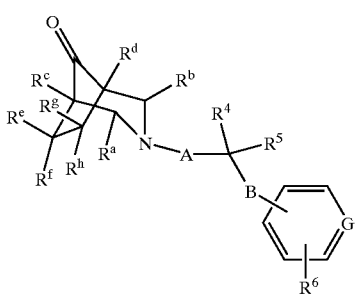

wherein $R^4$, $R^5$, $R^6$, $R^a$ to $R^h$, A, B and G are as hereinbefore defined, with a compound of formula XXII,

          XXII wherein $R^{31}$ represents unsubstituted $C_{1-4}$ alkyl, in the presence of a suitable reducing agent (e.g. sodium cyanoborohydride), for example at between room and reflux temperature, optionally in the presence of an appropriate solvent (e.g. a lower alkyl alcohol such as methanol) and/or a suitable catalyst (e.g. zinc chloride).

(t) for compounds of formula I in which $R^1$ represents —C(O)OR$^9$ and $R^a$ and/or $R^b$ represent $C_{1-4}$ alkyl, reaction of a corresponding compound of formula I in which $R^1$ represents —C(O)OR$^9$ and $R^a$ and $R^b$ represent H with one or more equivalents of a compound of formula XXIII,

          XXIII wherein $R^{32}$ represents $C_{1-4}$ alkyl and $L^4$ is a leaving group such as halo, alkylsulfate, alkanesulfonate or arenesulfonate, in the presence of an appropriate strong base (e.g. butyllithium), for example at between −80° C. and room temperature in the presence of a suitable solvent (e.g. N,N,N',N'-tetramethylethylene-diamine, THF or mixtures thereof).

(u) for compounds of formula I which are 3-azabicyclo[3.2.1]octane-nitrogen N-oxide derivatives, oxidation of the corresponding 3-azabicyclo[3.2.1]octane nitrogen of a corresponding compound of formula I, in the presence of a suitable oxidising agent (e.g. mCPBA), for example at 0° C. in the presence of a suitable organic solvent (e.g. dichloromethane);

(v) for compounds of formula I which are $C_{1-4}$ alkyl quaternary ammonium salt derivatives, in which the alkyl group is attached to a 3-azabicyclo[3.2.1]octane nitrogen, reaction, at the 3-azabicyclo[3.2.1]octane nitrogen, of a corresponding compound of formula I with a compound of formula XXIII, as hereinbefore defined, for example at room temperature in the presence of an appropriate organic solvent (e.g. N,N-dimethyl-formamide), followed by purification (using e.g. HPLC) in the presence of a suitable counter-ion provider (e.g. NH$_4$OAc); or (w) conversion of one $R^6$ substituent to another using techniques well known to those skilled in the art.

Compounds of formula IIA and IIB may be prepared by reaction of a compound of formula XXIV,

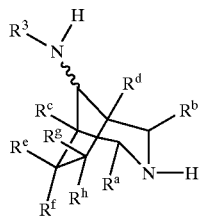

or an N-protected derivative thereof, wherein $R^3$, $R^a$ to $R^h$ are as hereinbefore defined, with a compound of formula m as hereinbefore defined, for example as described hereinbefore for the synthesis of compounds of formula I (process step (a)), or, in the case of compounds of formula IIA or IIB wherein $R^1$ or $R^2$ (as appropriate) represents a fragment of formula Ia in which A represents $CH_2$ and $R^4$ represents —OH or N(H)R$^{19}$, wherein $R^{19}$ is as hereinbefore defined, with a compound of formula VII as hereinbefore defined, for example as described hereinbefore for the synthesis of compounds of formula I (process step (d)).

Compounds of formula III may be prepared by standard techniques. For example, compounds of formula III in which $R^{28}$ represents a fragment of formula Ia, wherein:

(1) B represents —Z—O— may be prepared by coupling a compound of formula IX, as hereinbefore defined, to a compound of formula XXV,

          XXV wherein $R^4$, $R^5$, A, Z and $L^2$ are as hereinbefore defined, and the two $L^2$ groups may be the same or different; or (2) B represents —C(O)N(R$^{25}$)— may be prepared by coupling a compound of formula XXVI,

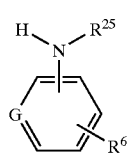          XXVI wherein G, $R^6$ and $R^{25}$ are as hereinbefore defined, to a compound of formula XXVII,

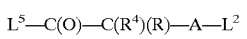          XXVI wherein $L^5$ represents a suitable leaving group (e.g. —OH or halo) and $R^4$, $R^5$, A and $L^2$ are as hereinbefore defined;

in both cases, under conditions which are well known to those skilled in the art.

Compounds of formula m in which $R^1$ represents a fragment of formula Ia, wherein A represents $C_2$ alkylene and $R^4$ represents —OR$^{18}$, in which $R^{18}$ represents $C_{1-6}$ alkyl, —E-aryl or —E—Het$^8$ may alternatively be prepared by reaction of a compound of formula XI, as hereinbefore defined, with a compound of formula XXVIII,

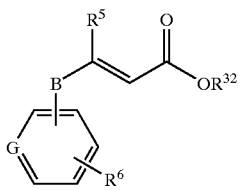

XXVIII wherein $R^5$, $R^6$, $R^{32}$, B and G are as hereinbefore defined, for example at between ambient temperature (e.g. 25° C.) and reflux temperature in the presence of a suitable base (e.g. potassium carbonate) and an appropriate organic solvent (e.g. acetonitrile), followed by conversion of the ester functionality to an $L^2$ group (in which $L^2$ is as hereinbefore defined), under conditions that are well known to those skilled in the art.

Compounds of formula IVA and IVB may be prepared by reaction of a compound of formula IIA or IIB, respectively, as hereinbefore defined, with a compound of formula XXIX,

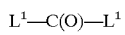

XXIX wherein $L^1$ is as hereinbefore defined, and in which the two $L^1$ groups may be the same or different, for example at between 0° C. and reflux temperature in the presence of a suitable base (e.g. triethylamine or potassium carbonate) and an appropriate organic solvent (e.g. toluene or dichloromethane).

Compounds of formula VII may be prepared in accordance with techniques that are known to those skilled in the art. For example, compounds of formula VII in which:

(1) B represents —$CH_2$O— and Y represents O may be prepared by reaction of a compound of formula IX, as hereinbefore defined, with a compound of formula XXX

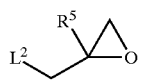

XXX wherein $R^5$ and $L^2$ are as hereinbefore defined, for example at elevated temperature (e.g. between 60° C. and reflux temperature) in the presence of a suitable base (e.g. potassium carbonate or NaOH) and an appropriate organic solvent (e.g. acetonitrile or toluene/water), or as otherwise described in the prior art;

(2) $R^5$ represents H, B represents a direct bond, $C_{1-4}$ alkylene, —Z—N($R^{25}$)—, —Z—S(O)$_n$— or —Z—O— (in which, in each case, the group Z represents $C_{1-4}$ alkylene attached to the carbon atom bearing $R^5$) and Y represents O may be prepared by reduction of a compound of formula XXXIA or XXXIB,

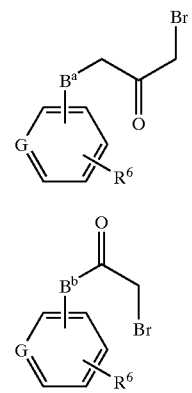

XXXIA

XXXIB wherein $B^a$ represents —$Z^a$—N($R^{25}$), —$Z^a$—S(O)$_n$— or —$Z^a$—O— (in which, in each case, the group $Z^a$ represents a direct bond or $C_{1-3}$ alkylene attached to the carbon atom bearing $R^5$), $B^b$ represents a direct bond or $C_{1-4}$ alkylene, and $R^6$, $R^{25}$, G and n are as hereinbefore defined, for example at between −15° C. and room temperature in the presence of a suitable reducing agent (e.g. NaBH$_4$) and an appropriate organic solvent (e.g. THF), followed by an internal displacement reaction in the resultant intermediate, for example at room temperature in the presence of a suitable base (e.g. potassium carbonate) and an appropriate organic solvent (e.g. acetonitrile);

(3) B represents a direct bond, $C_{1-4}$ alkylene, —Z—N($R^{25}$)—, —Z—S(O)$_2$— or —Z—O— (in which, in each case, the group Z represents $C_{1-4}$ alkylene attached to the carbon atom bearing $R^5$) and Y represents O may be prepared by oxidation of a compound of formula XXXIIA or XXXIIB,

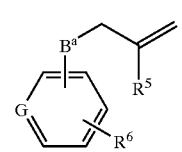

XXXIIA

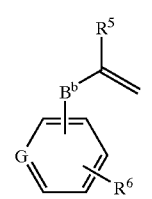

XXXIIB wherein $R^5$, $R^6$, $B^a$, $B^b$ and G are as hereinbefore defined, in the presence of a suitable oxidising agent (e.g. mCPBA), for example by refluxing in the presence of a suitable organic solvent (e.g. dichloromethane); or (4) B represents —Z—O—, in which group Z represents $C_{1-4}$ alkylene attached to the carbon atom bearing $R^5$, and Y represents —N($R^{19}$), wherein $R^{19}$ represents C(O)O$R^{21b}$ or —S(O)$_2R^{21c}$, may be prepared by cyclisation of a compound of formula XXXIII,

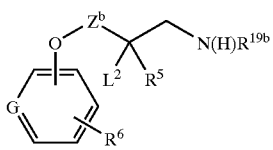

XXXIII wherein $R^{19b}$ represents —C(O)OR$^{21b}$ or —S(O)$_2$R$^{21c}$, $Z^b$ represents $C_{1-4}$ alkylene and $R^5$, $R^6$, $R^{21b}$, $R^{21c}$, G and $L^2$ are as hereinbefore defined, for example at between 0° C. and reflux temperature in the presence of a suitable base (e.g. sodium hydroxide), an appropriate solvent (e.g. dichloromethane, water, or a mixture thereof) and, if necessary, a phase transfer catalyst (such as tetrabutylammonium hydrogensulfate).

Compounds of formula VIIIA and VIIIB may be prepared in a similar fashion to compounds of formula I (see, for example process steps (a) to (d)).

Compounds of formula XIIA and XIIB may be prepared by replacement of the —OH group of a corresponding compound of formula I in which $R^4$ represents —OH with an $L^2$ group under conditions that are known to those skilled in the art.

Compounds of formula XIIIA and XIIIB in which E represents a direct bond may be prepared by reaction of corresponding compounds of formula I in which $R^4$ represents —OH with a compound of formula XXXIV,

 XXXIV wherein $R^{33}$ represents $C_{1-4}$ alkyl or aryl (which two groups are optionally substituted by one or more substituents selected from $C_{1-4}$ alkyl, halo and nitro), for example at between −10 and 25° C. in the presence of a suitable solvent (e.g. dichloromethane), followed by reaction with a suitable source of the azide ion (e.g. sodium azide), for example at between ambient and reflux temperature in the presence of an appropriate solvent (e.g. N,N-dimethylformamide) and a suitable base (e.g. sodium hydrogencarbonate).

Compounds of formula XIIIA and XIIIB may alternatively be prepared by reaction of a compound of formula IIA or IIB, as hereinbefore defined (except that $R^1$ or $R^2$ (as appropriate) does not represent a fragment of formula Ia), with a compound of formula XXXV,

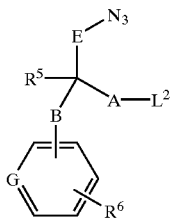

XXXV wherein $R^5$, $R^6$, A, B, E, G and $L^2$ are as hereinbefore defined, for example under analogous conditions to those described hereinbefore for the synthesis of compounds of formula I (process step (a)).

Compounds of formula XVIIIA and XVIIIB may be prepared by removing an optionally substituted benzyloxycarbonyl unit from (i.e. deprotecting) corresponding compounds of formula I in which B represents —N(R$^{25}$)C(O)OCH$_2$— and A represents J, wherein $R^{25}$ and J are as hereinbefore defined, for example under conditions which are known to those skilled in the art.

Compounds of formula XXI may be prepared by reaction of a compound of formula III in which $R^{28}$ represents a fragment of formula Ia with a compound of formula XXXVI,

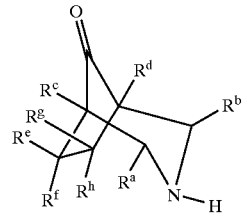

XXXVI wherein $R^a$ to $R^h$ are as hereinbefore defined, for example under conditions described hereinbefore (process step (a)).

Compounds of formula XXI in which both $R^a$ and $R^b$ represent H may alternatively be prepared by reaction of a compound of formula XXXVII,

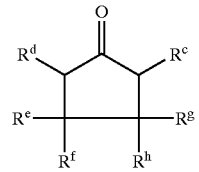

XXXVII wherein $R^c$ to $R^h$ are as hereinbefore defined, with a compound of formula XXXVIII,

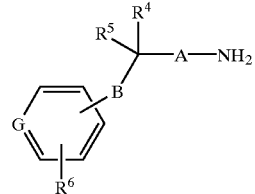

XXXVIII wherein $R^4$, $R^5$, $R^6$, A, B and G are as hereinbefore defined, in the presence of a formaldehyde (i.e. an appropriate source of formaldehyde, such as paraformaldehyde or formalin solution), for example at between room and reflux temperature in the presence of a suitable solvent (e.g. a lower alkyl alcohol such as methanol) and optionally in the presence of an appropriate acid (e.g. acetic acid).

Compounds of formula XXV may be prepared by reaction of a compound of formula XXXVI, as hereinbefore defined, or a N-protected derivative thereof, with a compound of formula XXXIX,

 XXXIX or (in the case where $R^3$ represents H) a protected derivative (e.g. N-benzyl) thereof, for example under conditions described hereinbefore for the synthesis of compounds of formula I (process step (s)).

Compounds of formula XXXV may be prepared in analogous fashion to compounds of formula XIIIA and XIIIB (i.e. from the corresponding alcohol).

Compounds of formula XXXVI in which both $R^a$ and $R^b$ represent H may be prepared by reaction of a compound of formula XXXVII with ammonia, or an N-protected derivative thereof (e.g. benzylamine), in the presence of a formaldehyde, for example under conditions described hereinbefore for the synthesis of compounds of formula XX.

Compounds of formulae V, VI, IX, X, XI, XIV, XV, XVI, XVII, XIX, XX, XXII, XXIII, XXV, XXVI, XXVII, XXVIII, XXIX, XXX, XXXIA, XXXIB, XXXIIA, XXXIIB, XXXIII, XXXIV, XXXVII, XXXVIII and XXXIX, and derivatives thereof, are either commercially available, are known in the literature, or may be obtained either by analogy with the processes described herein, or by conventional synthetic procedures, in accordance with standard techniques, from readily available starting materials using appropriate reagents and reaction conditions.

Substituents on the aryl (e.g. phenyl), and (if appropriate) heterocyclic, group(s) in compounds defined herein may be converted to other claimed substituents using techniques well known to those skilled in the art. For example, hydroxy may be converted to alkoxy, phenyl may be halogenated to give halophenyl, nitro may be reduced to give amino, amino may be acetylated to give acetylamino, etc.

The skilled person will also appreciate that various standard substituent or functional group interconversions and transformations within certain compounds of formula I will provide other compounds of formulae I. For example, carbonyl may be reduced to hydroxy or alkylene, and hydroxy may be converted to halo.

The compounds of the invention may be isolated from their reaction mixtures using conventional techniques.

It will be appreciated by those skilled in the art that, in the process described above, the functional groups of intermediate compounds may be, or may need to be, protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl and alkylcarbonyl groups (e.g. methyl- and ethylcarbonyl groups). Suitable protecting groups for amino include benzyl, tert-butyloxycarbonyl, 9-fluorenyl-methoxycarbonyl or benzyloxycarbonyl. Suitable protecting groups for amidino and guanidino include benzyloxycarbonyl. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are well known to those skilled in the art and as described hereinafter.

The use of protecting groups is fully described in "Protective Groups in Organic Chemistry", edited by J. W. F. McOmie, Plenum Press (1973), and "Protective Groups in Organic Synthesis", 3$^{rd}$ edition, T. W. Greene & P. G. M. Wutz, Wiley-Interscience (1999).

Persons skilled in the art will appreciate that, in order to obtain compounds of the invention in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

It will also be appreciated by those skilled in the art that, although certain protected derivatives of compounds of formula I, which may be made prior to a final deprotection stage, may not possess pharmacological activity as such, they may be administered parenterally or orally and thereafter metabolised in the body to form compounds of the invention which are pharmacologically active. Such derivatives may therefore be described as "prodrugs". Moreover, certain compounds of formula I may act as prodrugs of other compounds of formula I.

All prodrugs of compounds of formula I are included within the scope of the invention.

Some of the intermediates referred to hereinbefore are novel. According to a further aspect of the invention there is thus provided: (a) a compound of formula IIA or IIB, as hereinbefore defined, or a protected derivative thereof; (b) a compound of formula IVA or IVB, as hereinbefore defined, or a protected derivative thereof; (c) a compound of formula VIIIA or VIIIB, as hereinbefore defined, or a protected derivative thereof; (d) a compound of formula XIIA or XIIB, as hereinbefore defined, or a protected derivative thereof; (e) a compound of formula XIIIA or XIIIB, as hereinbefore defined, or a protected derivative thereof; (t) a compound of formula XVIIIA or XVIIIB, as hereinbefore defined, or a protected derivative thereof; (g) a compound of formula XX, as hereinbefore defined (provided that when $R^a$ to $R^h$ all represent H, G represents CH and $R^6$ is absent, then the group —A—C($R^4$)($R^5$)—B— does not represent unsubstituted ethyl), or a protected derivative thereof; and (h) a compound of formula XXIV, as hereinbefore defined (provided that $R^a$ to $R^h$ do not all represent H), or a protected derivative thereof.

Compounds of formula IIA that may be mentioned include those in which when $R^3$ represents H and $R^2$ represents —C(O)$R^{7a}$, then $R^{7a}$ does not represent phenyl substituted in the 2-position by $C_{1-6}$ alkoxy, in the 4-position by —NH$_2$ or —N(H)C(O)$R^{27h}$ (wherein $R^{27h}$ represents $C_{1-6}$ alkyl), and in the 5-position by halo or —SR$^{26c}$.

Compounds of formula IIB that may be mentioned include those in which:

(i) when $R^a$ to $R^h$ and $R^3$ all represent H then $R^1$ does not represent $C_{1-3}$ alkyl optionally substituted by phenyl;

(ii) when $R^3$ represents H then $R^1$ does not represent $C_{1-10}$ alkyl, or $C_{1-2}$ alkyl terminated by phenyl or thienyl (which phenyl or thienyl group is optionally substituted by one or two substituents selected from $C_{1-6}$ alkyl (optionally interrupted by oxygen), $C_{1-4}$ alkoxy, CF$_3$, halo, nitro, —C(O)OH or —C(O)O—$C_{1-6}$ alkyl;

(iii) $R^1$ does not represent $C_{1-2}$ alkyl substituted by phenyl (which phenyl group bears a para-[2-amino4-($C_{1-6}$ alkyl)-pyridin-6-yl] substituent and optionally one or two further substituents independently selected from methyl, methoxy and hydroxy) and optionally by one or two further aryl groups;

(iv) $R^1$ does not represent $C_2$ alkyl terminated by phenyl (which phenyl group bears a para-{2-[1-(2,5-dimethyl-1H-pyrrolyl)-4($C_{1-6}$ alkyl)-pyridin-6-yl} substituent and optionally one or two further substituents independently selected from methyl, methoxy and hydroxy); or (v) $R^1$ does not represent $C_1$ alkyl substituted by phenyl (which phenyl group bears a para-{2-[N-phthaloyl]4-($C_{1-6}$ alkyl)-pyridin-6-yl} substituent and a meta-methyl, methoxy or hydroxy group).

Medical and Pharmaceutical Use

The compounds of the invention are useful because they possess pharmacological activity. They are therefore indicated as pharmaceuticals.

Thus, according to a further aspect of the invention there is provided the compounds of the invention for use as pharmaceuticals.

In particular, the compounds of the invention exhibit myocardial electrophysiological activity, for example as demonstrated in the test described below.

The compounds of the invention are thus expected to be useful in both the prophylaxis and the treatment of arrhythmias, and in particular atrial and ventricular arrhythmias.

The compounds of the invention are thus indicated in the treatment or prophylaxis of cardiac diseases, or in indications related to cardiac diseases, in which arrhythmias are believed to play a major role, including ischaemic heart disease, sudden heart attack, myocardial infarction, heart failure, cardiac surgery and thromboembolic events.

In the treatment of arrhythmias, compounds of the invention have been found to selectively delay cardiac repolarization, thus prolonging the QT interval, and, in particular, to exhibit class III activity. Although compounds of the invention have been found to exhibit class III activity in particular, in the treatment of arrhythmias, their mode(s) of activity is/are not necessarily restricted to this class.

According to a further aspect of the invention, there is provided a method of treatment of an arrhythmia which method comprises administration of a therapeutically effective amount of a compound of the invention to a person suffering from, or susceptible to, such a condition.

Pharmaceutical Preparations

The compounds of the invention will normally be administered orally, subcutaneously, intravenously, intraarterially, transdermally, intranasally, by inhalation, or by any other parenteral route, in the form of pharmaceutical preparations comprising the active ingredient either as a free base, a pharmaceutically acceptable ion exchanger or a non-toxic organic or inorganic acid addition salt, in a pharmaceutically acceptable dosage form. Depending upon the disorder and patient to be treated, as well as the route of administration, the compositions may be administered at varying doses.

The compounds of the invention may also be combined with any other drugs useful in the treatment of arrhythmias and/or other cardiovascular disorders.

According to a further aspect of the invention there is thus provided a pharmaceutical formulation including a compound of the invention in admixture with a pharmaceutically acceptable adjuvant, diluent or carrier.

Suitable daily doses of the compounds of the invention in therapeutic treatment of humans are about 0.005 to 10.0 mg/kg body weight at oral administration and about 0.005 to 5.0 mg/kg body weight at parenteral administration.

The compounds of the invention have the advantage that they are effective against cardiac arrhythmias.

Compounds of the invention may also have the advantage that they may be more efficacious than, be less toxic than, have a broader range of activity (including exhibiting any combination of class I, class II, class III and/or class IV activity (especially class I and/or class IV activity in addition to class III activity)) than, be more potent than, be longer acting than, produce fewer side effects (including a lower incidence of proarrhythmias such as torsades de pointes) than, be more easily absorbed than, or that they may have other useful pharmacological properties over, compounds known in the prior art.

Biological Tests

Test A

Glucocorticoid-treated Mouse Fibroblasts as a Model to Detect Blockers of the Delayed Rectifier K Current IC50 for K channel blockade was determined using a microtitre plate based screen method, based on membrane potential changes of glucocorticoid-treated mouse fibroblasts. The membrane potential of glucocorticoid-treated mouse fibroblasts was measured using fluorescence of the bisoxonol dye $DiBac_{4(3)}$, which could be reliably detected using a fluorescence laser imaging plate reader (FLIPR). Expression of a delayed rectifier potassium channel was induced in mouse fibroblasts by 24 hours exposure to the glucocorticoide dexamehasone (5 $\mu$M). Blockade of these potassium channels depolarised the fibroblasts, resulting in increased fluorescence of $DiBac_{4(3)}$.

Mouse ltk fibroblasts (L-cells) were purchased from American Type Culture Collection (ATCC, Manassa, Va.), and were cultured in Dulbeccos modified eagle medium supplemented with fetal calf serum (5% vol/vol), penicillin (500 units/mL), streptomycin (500 $\mu$g/mL) and L-alanine-L-glutamine (0.862 mg/mL). The cells were passaged every 3–4 days using trypsin (0.5 mg/mL in calcium-free phosphate buffered saline, Gibco BRL). Three days prior to experiments, cell-suspension was pipetted out into clear-bottom, black plastic, 96-well plates (Costar) at 25 000 cells/well.

The fluorescence probe $DiBac_{4(3)}$ (DiBac Molecular probes) was used to measure membrane potential. $DiBac_{4(3)}$ maximally absorbs at 488 nM and emits at 513 nM. $DiBac_{4(3)}$ is a bisoxonol, and thus is negatively charged at pH 7. Due to its negative charge, the distribution of $DiBac_{4(3)}$ across the membrane is dependent upon the transmembrane potential: if the cell depolarizes (i.e. the cell interior becomes less negative relative to cell exterior), the $DiBac_{4(3)}$ concentration inside the cell increases, due to electrostatic forces. Once inside the cell, $DiBac_{4(3)}$ molecules can bind to lipids and proteins, which causes an increase in fluorescence emission. Thus, a depolarization will be reflected by an increase in $DiBac_{4(3)}$ fluorescence. The change in $DiBac_{4(3)}$ fluorescence was detected by a FLIPR.

Prior to each experiment, the cells were washed 4 times in phosphate-buffered saline (PBS) to remove all culture media. The cells were then treated with 5 $\mu$M $DiBac_{4(3)}$ (in 180 $\mu$L of PBS) at 35° C. Once a stable fluorescence was reached (usually after 10 min), 20 $\mu$L of the test substance was added, using FLIPR's internal 96 well pipetting system. Fluorescence measurements were then taken every 20 sec for a further 10 min. All experiments were carried out at 35° C., due to the high temperature sensitivity of both delayed rectifier potassium channel conductance and $DiBac_{4(3)}$ fluorescence. Test substances were prepared in a second 96 well plate, in. PBS containing 5 $\mu$M $DiBac_{4(3)}$. The concentration of substance prepared was 10 times that of the desired concentration in the experiment as an additional 1:10 dilution occurred during addition of substance during the experiment. Dofetilide (10 $\mu$M) was used as a positive control, i.e. to determine the maximum increase in fluorescence.

Curve-fitting, used to determine the IC50 values, was performed with the Graphpad Prism program (Graphpad Software Inc., San Diego, Calif.).

Test B

Metabolic Stability of Test Compounds

An in vitro screen was set up to determine the metabolic stability of the compounds of the invention.

The hepatic S-9 fraction from dog, man, rabbit and rat with NADPH as co-factor was used. The assay conditions were as follows: S-9 (3 mg/mL), NADPH (0.83 mM), Tris-HCl buffer (50 mM) at pH 7.4 and 10 $\mu$M of test compound.

The reaction was started by addition of test compound and terminated after 0, 1, 5, 15 and 30 minutes by raising the pH in the sample to above 10 (NaOH; 1 mM). After solvent extraction, the concentration of test compound was measured against an internal standard by LC (fluorescence/UV detection).

The percentage of test compound remaining after 30 minutes (and thus $t_{1/2}$) was calculated and used as a measure for metabolic stability.

The invention is illustrated by way of the following examples.

EXAMPLES

General Experimental Procedures

Mass spectra were recorded on one of the following instruments: a Perkin-Elmer SciX API 150ex spectrometer; a VG Quattro II triple quadrupole; a VG Platform II single quadrupole; or a Micromass Platform LCZ single quadrupole mass spectrometer (the latter three instruments were equipped with a pneumatically assisted electrospray interface (LC-MS)). $^1$H NMR and $^{13}$C NMR measurements were performed on a BRUKER ACP 300 and Varian 300, 400 and 500 spectrometers, operating at $^1$H frequencies of 300, 400 and 500 MHz respectively, and at $^{13}$C frequencies of 75.5, 100.6 and 125.7 MHz respectively. Alternatively, $^{13}$C NMR measurements were performed on a BRUKER ACE 200 spectrometer at a frequency of 50.3 MHz.

Rotamers may or may not be denoted in spectra depending upon ease of interpretation of spectra. Unless otherwise stated, chemical shifts are given in ppm with the solvent as internal standard.

Synthesis of Intermediates

The following intermediates were not commercially available, and were therefore prepared by the methods described below.

Preparation A

3-Benzyl-3-azabicyclo[3.2.1]octan-8-one

A solution of benzylamine (127.4 g, 1.19 mol) in methanol (125 mL) was added dropwise over 3 h to a refluxing solution of cyclopentanone (100 g, 1.19 mol), paraformaldehyde (107 g, 3.57 mol), and glacial acetic acid (71.4 g, 1.19 mol) in methanol (600 mL) under nitrogen. After 1 h at reflux, the brown mixture was stirred overnight at 25° C. and concentrated in vacuo. The resulting oil was diluted with water (200 mL) and basified with 6 N NaOH (200 mL). The aqueous solution was extracted with dichloromethane (3×400 mL). The combined organic extracts were dried (Na$_2$SO$_4$), and concentrated in vacuo. The residue was chromatographed, eluting with ethyl acetate: dichloromethane (1:35), to afford 47.6 g (19%) of the sub-title compound as a yellow oil.

$^1$H NMR (300 MHz, CCDl$_3$): δ 7.40–7.10 (m, 5H), 3.60 (s, 2H), 3.01–2.92 (m, 2 H), 2.57–2.50 (m, 2H), 2.18–2.0 (m, 4H), 1.90–1.81 (m, 2H).

Preparation B

3-Benzyl-N-methyl-3-azabicyclo[3.2.1]octan-8-amine

A mixture of sodium cyanoborohydride (35.0 g, 0.557 mol) and zinc chloride (37.9 g, 0.278 mol) in methanol (500 mL) was added dropwise to a mechanically stirred mixture of 3-benzyl-3-azabicyclo[3.2.1]octan-8-one (Preparation A; 120 g, 0.557 mol) and methylamine hydrochloride (151 g, 2.23 mol) in methanol (1.0 L) at 25° C. under nitrogen. After 2.5 h of stirring, 6 N NaOH (90 mL) was added dropwise. The mixture was filtered through a pad of Celite®, washing with methanol (500 mL). The filtrate was concentrated in vacuo. Water (500 mL) was added, and the aqueous mixture was extracted with ethyl acetate (3×500 mL). The combined organic extracts were dried (Na$_2$SO$_4$), and concentrated in vacuo. The residue was chromatographed, eluting with methanol dichloromethane (1:10), to afford 63.0 g (49%) of the sub-title compound as a solid.

$^1$H NMR (300 MHz, CCDl$_3$): δ 7.40–7.10 (m, 5H), 3.88 (s, 2H), 3.60 (s, 2H), 3.45 (s, 1H), 2.85–2.80 (m, 1H), 2.60–2.45 (m, 2H), 2.50 (s, 3H), 2.15 (s, 2H), 2.40–2.30 (m, 2H), 1.70–1.62 (m, 2H).

Preparation C tert-Butyl 3-Benzyl-3-azabicyclo[3.2.1]oct-8-yl (methyl)carbamate A mixture of 3-benzyl-N-methyl-3-azabicyclo[3.2.1] octan-8-amine (Preparation B; 168.1 g, 0.730 mol) and di-tert-butyldicarbonate (159 g, 0.730 mol) in dichloromethane (2.5 L) was stirred overnight at 25° C. under nitrogen. The mixture was concentrated in vacuo to yield 240 g (100%) of the sub-title compound as a white solid, which was used without purification.

$^1$H NMR (300 MHz, CCDl$_3$): δ 7.40–7.30 (m, 5H), 4.0 (s, 2H), 3.60 (s, 2H), 3.45 (s, 1H), 3.02–2.50 (m, 5H), 2.80 (s, 3H), 2.0–1.70 (m, 4H), 1.50 (s, 9H).

Preparation D tert-Butyl 3-Azabicyclo[3.2.1]oct-8-yl(methyl) carbamate

A solution of 1 M HCl in diethyl ether (730 mL, 730 mmol) was added dropwise to a solution tert-butyl 3-benzyl-3-azabicyclo[3.2.1]oct-8-yl(methyl)carbamate (Preparation C; 241 g, 0.730 mol) in diethyl ether (1.5 L). The resulting precipitate was collected via filtration through a sintered glass funnel and then dried in vacuo. The solid was dissolved in methanol (4.0 L), and 10% palladium on carbon (24 g) was added. The mixture was stirred under one atmosphere of hydrogen at 40° C. overnight. The catalyst was filtered through a pad of Celite®, washing with methanol (1.0 L). The filtrate was concentrated in vacuo, and chromatographed, eluting with dichloromethane:methanol-:concentrated ammonium hydroxide (88:10:2) to afford 70 g (40%) of an oil. A solution of this oil (70 g, 296 mmol) in diethyl ether (1.0 L) was treated with 1 M HCl in diethyl ether (300 mL), added dropwise. The resulting precipitate was removed via filtration through sintered glass funnel. The salt was slurried in acetonitrile and the solid collected to give 80 g of the HCl salt of the title compound:

Mp: 170–177° C.; $^1$H NMR (300 MHz, CD$_3$OD): δ 3.35–3.10 (m, 6H), 2.90 (s, 3H), 3.02–2.80 (m, 2H), 2.02–1.70 (m, 4H), 1.45 (s, 9H). $^{13}$C NMR (75 MHz, CD$_3$OD): δ 159.2, 81.8, 61.6, 45.6, 36.6, 36.0, 28.5, 24.8. CI-MS: (M+1)=241 m/z.

The free base was obtained by treating the HCl salt with K$_2$CO$_3$ in MeCN

Preparation E

4-{3-[3-Azabicyclo[3.2.1]oct-8-yl(methyl)amino]-2-hydroxypropoxy}-benzonitrile (i) 4-(2-Oxiranylmethoxy)benzonitrile Epichlorohydrin (800 mL) and K$_2$CO$_3$ (414 g) were added to a stirred solution of p-cyanophenol (238 g) in 2.0 L MeCN and the reaction mixture was refluxed under inert atmosphere for 2 h. The hot solution was filtered and the filtrate concentrated to give a clear oil. This was crystallized from di-iso-propyl ether to give the sub-title compound in 75% yield.

(ii) 4-{3-[(3-Benzyl-3-azabicyclo[3.2.1]oct-8-yl)(methyl) amino]-2-hydroxypropoxy}benzonitrile To a solution of 3-benzyl-N-methyl-3-azabicyclo[3.2.1] octan-8-amine (Preparation B; 3.72 g, 16.1 mmol) in dichloromethane (80 mL) at 25° C. under nitrogen was added trimethylaluminum (8.05 mL of 2.0 M in hexane, 16.1 mmol). After stirring at 25° C. for 30 min, 4-(2-oxiranylmethoxy)benzonitrile (see step (i) above; 2.83 g, 16.1 mmol) was added in one portion, and the mixture was stirred overnight. The mixture was quenched with 6 N NaOH (13.5 mL) and stirred 1 h. Water (100 mL) was added, and the aqueous layer was extracted with dichloromethane (3×100 mL). The combined organic extracts were dried (Na$_2$SO$_4$), filtered and concentrated in vacuo to afford an oil. The residue was chromatographed on silica gel, eluting with dichloromethane:methanol (98:2), to afford 4.30 g (66%) of the sub-title compound as a colorless oil.

$^1$H NMR (300 MHz, CDCl$_3$): δ 7.58 (d, J=8.2 Hz, 2H), 7.32–7.20 (m, 5H), 6.97 (d, J=8.2 Hz, 2H), 4.22–4.14 (m, 1H), 4.08–4.0 (m, 2H), 3.50 (s, 2H), 2.82–2.70 (m, 1H), 2.64–2.52 (m, 2H), 2.48–2.30 (m, 5H), 2.30 (s, 3H), 1.94–1.82 (m, 2H), 1.72–1.50 (m, 4H). $^{13}$C NMR (75 MHz, CDCl$_3$): δ 162.4, 139.4, 134.0, 128.2, 128.0, 126.8, 119.5, 115.6, 104.4, 70.6, 68.0, 66.0, 62.4, 57.7, 52.4, 52.0, 40.4, 36.8, 36.2, 27.8. CI-MS: (M+1)=406 m/z.

(iii) 4-{3-[3-Azabicyclo[3.2.1]oct-8-yl(methyl)amino]-2-hydroxypropoxy}-benzonitrile A solution of HCl in ether (4.3 mL of 1.0 M, 4.3 mmol) was added dropwise to a solution of 4-{3-[(3-benzyl-3-azabicyclo[3.2.1]oct-8-yl)(methyl)amino]-2-hydroxypropoxy}benzonitrile (see step (ii) above; 1.75 g, 4.32 mmol) in diethyl ether (50 mL) at 0° C. Concentration in vacuo gave the HCl salt. The HCl salt and 10% palladium on carbon (175 mg) were suspended in methanol (25 mL), then stirred under an atmosphere of hydrogen for 5 h at 40° C. The catalyst was removed by filtration through a short pad of Celite®, washing with methanol (50 mL). The filtrate was concentrated in vacuo and chromatographed on silica gel, eluting with dichloromethane:methanol:concentrated ammonium hydroxide (88:10:2), to afford 980 mg (72%) of the tide compound as a white foam.

$^1$H NMR (300 MHz, CDCl$_3$): δ 7.58 (d, J=8.2 Hz, 2H), 6.97 (d, J=8.2 Hz, 2H), 4.30–4.16 (m, 1H), 4.12–4.0 (m, 2H), 3.33–3.10 (m, 4H), 2.82–2.70 (m, 1H), 2.52–2.30 (m, 4H), 2.30 (s, 3H), 2.20–2.05 (m, 2H), 1.91–1.70 (m, 4H). $^{13}$C NMR (75 MHz, CDCl$_3$): δ 162.4, 134.0, 119.5, 115.6, 104.4, 70.6, 68.0, 66.0, 57.7, 52.0, 40.4, 36.8, 36.2, 27.8. CI-MS: (M+1)=316 m/z.

Preparation F

4-{2-Hydroxy-3-[8-(methylamino)-3-azabicyclo[3.2.1]oct-3-yl]propoxy}-benzonitrile (i) tert-Butyl 3-[3-(4-Cyanophenoxy)-2-hydroxypropyl]-3-azabicyclo-[3.2.1]oct-8-yl(methyl)carbamate To a solution of tert-butyl 3-azabicyclo[3.2.1]oct-8-yl (methyl)carbamate (Preparation D; 1.68 g, 7.0 mmol) in dichloromethane (35 mL) at 25° C. under nitrogen was added trimethylaluminum (3.75 mL of 2.0 M in hexanes, 7.0 mmol). After stirring at 25° C. for 30 min, 4-(2-oxiranylmethoxy)benzonitrile (Preparation E(i); 1.22 g, 7.0 mmol) was added in one portion, and the mixture was stirred overnight. The mixture was quenched with 3 N NaOH (11.5 mL) and stirred for 1 h. Water (30 mL) was added, and the aqueous layer was extracted with dichloromethane (3×30 mL). The combined organic extracts were dried (Na$_2$SO$_4$), filtered and concentrated in vacuo to afford an oil. The residue was chromatographed on silica gel, eluting with dichloromethane:methanol (98:2), to afford 2.35 g (81%) of the subtitle compound as a white solid.

Mp: 109–112° C.; $^1$H NMR (300 MHz, CDCl$_3$): δ 7.58 (d, J=8.2 Hz, 2H), 6.97 (d, J=8.2 Hz, 2H), 4.10–3.70 (m, 3H), 3.22–3.16 (m, 1H), 2.90 (s, 3H), 2.70–2.25 (m, 8H), 1.50–1.82 (m, 5H), 1.45 (s, 9H). $^{13}$C NMR (75 MHz, CDCl$_3$): δ 162.2, 157.6, 134.0, 132.7, 119.2, 115.6, 104.1, 79.8, 70.6, 65.2, 60.8, 59.8, 58.0, 55.2, 52.0, 37.8, 37.2, 35.4, 28.4, 26.1, 26.0. CI-MS: (M+1)=416 m/z.

(ii) 4-{2-Hydroxy-3-[8-(methylamino)-3-azabicyclo[3.2.1] oct-3-yl]-propoxy}benzonitrile A suspension of tert-butyl 3-[3-(4-cyanophenoxy)-2-hydroxypropyl]-3-azabicyclo[3.2.1]oct-8-yl(methyl) carbamate (see step (i) above; 3.15 g, 7.58 mmol) in ethyl acetate saturated with HCl (40 mL) was stirred for 5 h at 25° C. under nitrogen. The mixture was partitioned with water (100 mL) and ethyl acetate (50 mL). The aqueous layer was separated and washed with ethyl acetate. The aqueous layer was separated, basified with saturated sodium bicarbonate (30 mL) and then extracted with dichloromethane (3×50 mL). The organic extracts were dried (Na$_2$SO$_4$), filtered, concentrated in vacuo and then chromatographed on silica gel, eluting with dichloromethane:methanol:concentrated ammonium hydroxide (88:10:2), to afford 2.30 g (96%) of the title compound as a colorless oil.

$^1$H NMR (300 MHz, CDCl$_3$): δ 7.58 (d, J=8.2 Hz, 2H), 6.97 (d, J=8.2 Hz, 2H), 4.10–3.90 (m, 4H), 3.90 (d, J=8.2 Hz, 1H), 2.70–2.67 (m, 1H), 2.60–2.30 (m, 5H), 2.40 (s, 3H), 2.08–2.0 (m, 2H), 1.82–1.64 (m, 5H). $^{13}$C NMR (75 MHz, CDCl$_3$): δ 162.2, 134.0, 132.7, 119.2, 115.6, 104.1, 70.6, 65.2, 60.8, 59.8, 54.2, 50.4, 37.8, 37.2, 35.4, 27.4, 27.2. CI-MS: (M+1)=316 m/z.

Preparation G 4-({3-[8-(Methylamino)-3-azabicyclo[3.2.1]oct-3-yl]propyl}amino)-benzonitrile (i) 4-[(3-Hydroxypropyl)amino]benzonitrile A mixture of 4-fluorobenzonitrile (12.0 g, 99.1 mmol) and 3-amino-1-propanol (59.6 g, 793 mmol) was stirred at 80° C. under an inert atmosphere for 3 hours before water (150 mL) was added. The mixture was allowed to cool to rt, and was then extracted with diethyl ether. The organic layer was separated, dried (Na$_2$SO$_4$), filtered and concentrated in vacuo to yield 17 g (97%) of the title compound as an oil that crystallised upon standing.

(ii) 3-(4-Cyanoanilino)propyl 4-Methylbenzenesulfonate

A cooled (0° C.) solution of 4-[(3-hydroxypropyl)amino] benzonitrile (see step (i) above; 17 g, 96.5 mmol) in dry MeCN (195 mL) was treated with triethylamine (9.8 g, 96.5 mmol) and then p-toluenesulfonyl chloride (20.2 g, 106 mmol). The mixture was stirred at 0° C. for 90 minutes before being concentrated in vacuo. Water (200 mL) was added to the residue, and the aqueous solution was extracted with DCM. The organic phase was dried ($Na_2SO_4$), filtered and concentrated in vacuo. The resulting residue was purified by crystallisation from iso-propanol to yield 24.6 g (77%) of the sub-title compound.

(iii) tert-Butyl 3-[3-(4-Cyanoanilino)propyl]-3-azabicyclo [3.2.1]oct-8-yl-(methyl)carbamate A mixture of tert-butyl 3-azabicyclo[3.2.1]oct-8-yl (methyl)carbamate (Preparation D; 2.90 g, 12.1 mmol), 3-(4-cyanoanilino)propyl 4-methyl-benzenesulfonate (see step (ii) above; 3.98 g, 12.1 mmol), and potassium carbonate (1.67 g, 12.1 mmol) in DMF (50 mL) was heated at 90° C. under nitrogen for 4 h. The mixture was partitioned with water (50 mL) and diethyl ether (50 mL). The aqueous layer was separated and then extracted with diethyl ether (2×50 mL). The combined organic extracts were washed with saturated brine (2×30 mL), dried ($Na_2SO_4$), filtered and then concentrated in vacuo. The residue was chromatographed on silica gel, eluting with dichloromethane:methanol (98:2), to afford 2.85 g (59%) of the sub-title compound.

$^1$H NMR (300 MHz, $CDCl_3$): δ 7.40 (d, J=8.2 Hz, 2H), 6.52 (d, J=8.2 Hz, 2H), 3.25–3.18 (m, 4H), 2.80 (s, 3H), 2.72–2.60 (m, 4H), 2.50–2.42 (m, 2H), 2.28–2.20 (m, 2H), 1.85–1.70 (m, 6H), 1.45 (s, 9H). $^{13}$C NMR (75 MHz, $CDCl_3$): δ 157.4, 152.0, 133.8, 133.2, 120.4, 111.8, 97.7, 79.8, 61.4, 57.8, 53.9, 44.2, 37.8, 35.0, 28.0, 26.0, 24.2. CI-MS: (M+1)=399 m/z.

(iv) 4-({3-[8-(Methylamino)-3-azabicyclo[3.2.1]oct-3-yl] propyl}amino)-benzonitrile A suspension of tert-butyl 3-[3-(4-cyanoanilino)propyl]-3-azabicyclo-[3.2.1]oct-8-yl(methyl)carbamate (see step (iii) above; 2.66 g, 6.67 mmol) in ethyl acetate saturated with HCl (40 mL) was stirred overnight at 25° C. under nitrogen. The mixture was partitioned with water (100 mL) and ethyl acetate (50 mL). The aqueous layer was basified with saturated sodium bicarbonate (50 mL) and then extracted with dichloromethane (3×50 mL). The organic extracts were dried ($Na_2SO_4$), filtered, concentrated in vacuo and then chromatographed on silica gel, eluting with dichloromethane:methanol:concentrated ammonium hydroxide (92:7:1), to afford 1.07 g (54%) of the title compound as a white solid.

$^1$H NMR (300 MHz, $CD_3OD$): δ 7.40 (d, J=8.2 Hz, 2H), 6.52 (d, J=8.2 Hz, 2H), 3.40–3.10 (m, 6H), 2.72–2.40 (m, 6H), 2.40 (s, 3H), 2.22–2.0 (m, 2H), 1.80–1.62 (m, 5H). $^{13}$C NMR (75 MHz, $CD_3OD$): δ 154.0, 134.2, 113.4, 97.7, 64.4, 57.8, 53.9, 42.5, 37.8, 34.0, 28.0, 26.0. CI-MS: (M+1)=299 m/z.

Preparation H 4-({3-[3-Azabicyclo[3.2.1]oct-8-yl(methyl)amino] propyl}amino)-benzonitrile (i) 4-(13-[(3-Benzyl-3-azabicyclo[3.2.1]oct-8-yl)(methyl) amino]propyl]-amino)benzonitrile A mixture of 3-benzyl-N-methyl-3-azabicyclo[3.2.1] octan-8-amine (Preparation B; 4.0 g, 17.4 mmol), 3-(4-cyanoanilino)propyl 4-methyl-benzenesulfonate (Preparation G(ii); 5.74 g, 17.4 mmol), and potassium carbonate (2.40 g, 17.4 mmol) in DMF (85 mL) was heated at 90° C. under nitrogen overnight. The mixture was partitioned with water (200 mL) and diethyl ether (150 mL). The aqueous layer was extracted with ethyl acetate (2×50 mL). The combined organic extracts were washed with brine (2×30 mL), dried ($Na_2SO_4$), filtered and then concentrated in vacuo. The residue was chromatographed on silica gel, eluting with dichloromethane:methanol (98:2), to afford 3.40 g (50%) of the sub-title compound as a white solid.

Mp: 91–93° C.; $^1$H NMR (300 MHz, $CDCl_3$): δ 7.48 (d, J=8.2 Hz, 2H), 7.32–7.20 (m, 5H), 6.60 (d, J=8.2 Hz, 2H), 5.78–5.70 (m, 1H), 3.50 (s, 2H), 3.30–3.20 (m, 2H), 2.62–2.52 (m, 4H), 2.40–2.32 (m, 2H), 2.25 (s, 3H), 2.25–2.10 (m, 3H), 1.92–1.80 (m, 4H), 1.72–1.60 (m, 2H). $^{13}$C NMR (75 MHz, $CDCl_3$): δ 152.2, 140.0, 133.8, 128.4, 128.2, 136.4, 121.2, 112.2, 98.4, 68.8, 62.4, 54.5, 52.8, 43.0, 39.9, 36.4, 28.8, 25.8. CI-MS: (M+1)=389 m/z.

(ii) 4-({3-[3-Azabicyclo[3.2.1]oct-8-yl(methyl)amino] propyl}amino)-benzonitrile A solution of HCl in diethyl ether (3.4 mL of 1.0 M, 3.4 mmol) was added dropwise to a solution of 4-({3-[(3-benzyl-3-azabicyclo[3.2.1]oct-8-yl)(methyl)amino] propyl}amino)benzonitrile (see step (i) above; 1.32 g, 3.39 mmol) in diethyl ether (50 mL) at 0° C. Concentration in vacuo gave the HCl salt. The HCl salt and 10% palladium on carbon (132 mg) were suspended in methanol (20 mL) and stirred under an atmosphere of hydrogen for 2 h at 40° C. The catalyst was removed by filtration through a short pad of Celite®, washing with methanol (50 mL). The filtrate was concentrated in vacuo and chromatographed on silica gel, eluting with dichloromethane:methanol:concentrated ammonium hydroxide (88:10:2), to afford 590 mg (59%) of the title compound as a white foam.

Mp: 59–63° C.; $^1$H NMR (300 MHz, $CD_3OD$): δ 7.48 (d, J=8.2 Hz, 2H), 6.66 (d, J=8.2 Hz, 2H), 4.80 (s, 1H), 3.35–3.10 (m, 4H), 2.62–2.40 (m, 4H), 2.30–2.10 (m, 4H), 2.25 (s, 3H), 1.91–1.70 (m, 6H). $^{13}$C NMR (75 MHz, $CD_3OD$): δ 154.0, 133.8, 122.2, 113.2, 97.8, 68.8, 54.5, 45.8, 42.0, 40.4, 37.0, 26.8, 26.6. CI-MS: (M+1)=299 m/z.

Preparation I

4-{1-(3,4-Dimethoxyphenoxy)-4-[8-(methylamino)-3-azabicyclo[3.2.1]oct-3-yl]butyl}benzonitrile (i) 4-[1-(3,4-Dimethoxyphenoxy)-3-butenyl]benzonitrile A cooled (0° C.) mixture of 4-(1-hydroxy-3-butenyl) benzonitrile (14.6 g, 84.3 mmol) and 3,4-dimethoxyphenol (19.5 g, 125.4 mmol) in toluene (500 mL) was treated with tributylphosphine (32.14 mL of 97% purity, 25.6 g, 126.4 mmol), followed by 1,1'-(azodicarbonyl)dipiperidine (31.8 g, 126.4 mmol). After addition was complete, the reaction mixture thickened and the temperature rose to 15° C. Additional toluene was added (500 mL), and the mixture stirred at rt overnight. The precipitate of tributylphosphine oxide was then removed by filtration and the filtrate concentrated in vacuo to give 65.8 g of crude product. This was purified by chromatography on silica gel, eluting with toluene:methanol (98:2), to yield 17.9 g of the sub-title compound.

(ii) 4-[1-(3,4-Dimethoxyphenoxy)-4-hydroxybutyl] benzonitrile

Borane-methyl sulfide complex (2 M in ether, 11 mL, 22 mmol) was added dropwise to a cooled (−5° C.) solution of 4-[1-(3,4-dimethoxyphenoxy)-3-butenyl]benzonitrile (see step (i) above; 17.6 g, 56.8 mmol) in dry THF (15 mL) over a period of 15 minutes (during which time the reaction temperature rose to 0° C.). The resulting mixture was stirred at between 0 and 10° C. for 1.5 h, before being allowed to warm to rt. Stirring was continued for a further 3.5 h at this temperature before water (22 mL) and sodium perborate tetrahydrate (11 g, 66 mmol) were added. The biphasic mixture was stirred for 2 h at rt before the water layer was separated and extracted with ether. The combined organic layers were washed with brine, dried and concentrated in vacuo. The resulting residue was purified by chromatography on silica gel, eluting with IPA: ethyl acetate:heptane (5:25:70) to yield 14.5 g (77%) of the sub-title compound.

(iii) 4-(4-Cyanophenyl)-4-(3,4-dimethoxyphenoxy)butyl Methanesulfonate

A solution of methanesulfonyl chloride (3.4 mL, 5.0 g, 44 mmol) in DCM (15 mL) was added slowly to a cooled (−5° C.) mixture of 4-[1-(3,4-dimethoxyphenoxy)-4-hydroxybutyl]benzonitrile (see step (ii) above; 11 g, 34 mmol) and triethylamine (7 mL, 5.2 g, 50.6 mmol) in DCM (50 ML), during which addition the temperature did not rise above 2° C. Stirring was continued at between 0 and 5° C. for a further 2 h before water was added. The resulting organic layer was separated, and washed with water, separated again and then dried to give the subtitle compound in 100% yield.

(iv) tert-Butyl 3-[4-(4-cyanophenyl)-4-(3,4-dimethoxyphenoxy)butyl]-3-azabicyclo[3.2.1]oct-8-yl (methyl)carbamate A mixture of tert-butyl 3-azabicyclo[3.2.1]oct-8-yl (methyl)carbamate (Preparation D; 2.60 g, 10.9 mmol), 4-(4-cyanophenyl)-4-(3,4-dimethoxyphenoxy)butyl methanesulfonate (see step (iii) above; 4.40 g, 10.9 mmol), and potassium carbonate (1.50 g, 10.9 mmol) in DMF (50 mL) was heated at 90° C. under nitrogen for 4 h. The mixture was partitioned with water (50 mL) and diethyl ether (50 mL). The aqueous layer was extracted with diethyl ether (2×50 mL). The combined organic extracts were washed with brine (2×30 mL), dried ($Na_2SO_4$), filtered and then concentrated in vacuo. The residue was chromatographed on silica gel, eluting with dichloromethane:methanol (98:2), to afford 3.60 g (60%) of the sub-title compound as an amorphous solid.

$^1$H NMR (300 MHz, $CDCl_3$): δ 7.62 (d, J=8.2 Hz, 2H), 7.46 (d, J=8.2 Hz, 2H), 6.62 (d, J=8.2 Hz, 2H); 6.50 (s, 1H), 6.18 (d, J=4.0 Hz, 2H), 5.10 (m, 1H), 3.80 (s, 3H), 3.76 (s, 3H), 3.20–3.16 (m, 1H), 2.90 (s, 3H), 2.62–2.56 (m, 2H), 2.50–2.12 (m, 6H), 2.0–1.60 (m, 7H), 1.43 (s, 9H). 13C NMR (75 MHz, $CDCl_3$): δ 157.8, 152.0, 149.8, 148.2, 143.6, 132.4, 130.0, 118.4, 112.0, 111.7, 105.6, 102.2, 79.6, 79.4, 61.8, 57.6, 56.4, 55.8, 53.8, 53.4, 37.6, 35.8, 35.4, 28.2, 26.4, 22.4. CI-MS: (M+1)=550 m/z.

(v) 4-{1-(3,4-Dimethoxyphenoxy)-4-[8-(methylamino)-3-azabicyclo-[3.2.1]oct-3-yl]butyl}benzonitrile A suspension of tert-butyl 3-[4-(4-cyanophenyl)-4-(3,4-dimethoxyphenoxy)butyl]-3-azabicyclo[3.2.1]oct-8-yl (methyl)carbamate (see step (iv) above; 2.67 g, 4.86 mmol) in ethyl acetate saturated with HCl (60 mL) was stirred overnight at 25° C. under nitrogen. The mixture was partitioned with water (100 mL) and ethyl acetate (50 mL). The aqueous layer was washed with ethyl acetate (50 mL) before being separated, basified with saturated sodium bicarbonate (50 mL) and then extracted with dichloromethane (3×50 mL). The organic extracts were dried ($Na_2SO_4$), filtered, concentrated in vacuo and then chromatographed on silica gel, eluting with dichloromethane:methanol:concentrated ammonium hydroxide (92:7:1),to afford 1.32 g (61%) of the title compound as a yellow oil.

$^1$H NMR (300 MHz, $CDCl_3$): δ 7.62 (d, J 8.2 Hz, 2H), 7.46 (d, J=8.2 Hz, 2H), 6.62 (d, J=8.2 Hz, 2H), 6.50 (s, 1H), 6.18 (d, J=4.0 Hz, 2H), 5.21–5.10 (m, 1H), 3.80 (s, 3H), 3.76 (s, 3H), 3.50–3.48 (m, 1H), 2.70–2.62 (m, 1H), 2.40 (s, 3H), 2.48–2.30 (m, 4H), 2.10–1.40 (m, 10H). $^{13}$C NMR (75 MHz, $CDCl_3$): δ 152.0, 149.8, 148.2, 143.6, 132.4, 126.5, 118.4, 112.0, 111.7, 105.6, 102.2, 79.6, 79.4, 62.5, 57.6, 56.4, 55.8, 53.8, 53.4, 37.6, 35.8, 35.4, 28.2, 26.4. CI-MS: (M+1)=450 m/z.

Preparation J

4-[4-[3-Azabicyclo[3.2.1]oct-8-yl(methyl)amino]-1-(3,4dimethoxyphenoxy)butyl]benzonitrile (i) 4-[4-[(3-Benzyl-3-azabicyclo[3.2.1]oct-8-yl)(methyl) amino]-1-(3,4-dimethoxyphenoxy)butyl]benzonitrile A mixture of 3-benzyl-N-methyl-3-azabicyclo[3.2.1] octan-8-amine (Preparation B; 1.3 g, 5.95 mmol), 4-(4-cyanophenyl)-4-(3,4-dimethoxyphenoxy)butyl methanesulfonate (Preparation I(iii); 2.41 g, 5.95 mmol), and potassium carbonate (822 mg, 5.95 mmol) in DMF (25 mL) was heated at 90° C. under nitrogen overnight. The mixture was partitioned with water (50 mL) and diethyl ether (40 mL). The aqueous layer was extracted with diethyl ether (2×40 mL). The combined organic extracts were washed with brine (2×30 mL), dried ($Na_2SO_4$), filtered and then concentrated in vacuo. The residue was chromatographed on silica gel, eluting with dichloromethane:methanol (98:2), to afford 860 mg (27%) of the sub-title compound.

$^1$H NMR (300 MHz, $CDCl_3$): δ 7.62 (d, J=8.2 Hz, 2H), 7.46 (d, J=8.2 Hz, 2H), 7.38–7.20 (m, 5H), 6.62 (d, J=8.2 Hz, 2H), 6.50 (s, 1H), 6.18 (d, J=4.0 Hz, 2H), 5.22–5.10 (m, 1H), 3.80 (s, 3H), 3.76 (s, 3H), 3.50 (s, 2H), 2.68–2.52 (m, 2H), 2.50–2.28 (m, 4H), 2.15 (s, 3H), 2.0–1.75 (m, 4H), 1.68–1.50 (m, 5H). $^{13}$C NMR (75 MHz, $CDCl_3$): δ 152.0, 149.8, 148.2, 143.6, 140.0, 132.4, 128.0, 127.8, 126.0, 118.4, 112.0, 111.7, 105.6, 102.2, 79.6, 68.4, 61.8, 59.2, 57.6, 56.4, 55.8, 53.8, 53.4, 39.8, 35.8, 35.4, 28.2, 22.4. CI-MS: (M+1)=540 m/z.

(ii) 4-[4-[3-Azabicyclo[3.2.1]oct-8-yl(methyl)amino]-1-(3, 4dimethoxyphenoxy)butyl]benzonitrile A solution of HCl in diethyl ether (4.1 mL of 1.0 M, 4.1 mmol) was added dropwise to a solution of 4-[4-[(3-benzyl-3-azabicyclo[3.2.1]-oct-8-yl)(methyl)amino]-1-(3,4-dimethoxyphenoxy)butyl]benzonitrile (see step (i) above; 2.20 g, 4.08 mmol) in diethyl ether (50 mL) at 0° C. Concentration in vacuo gave the HCl salt. The HCl salt and 10% palladium on carbon (220 mg) were suspended in methanol (20 mL) and stirred under an atmosphere of hydrogen overnight at 40° C. The catalyst was removed by filtration through a short pad of Celite®, washing with methanol (50 mL). The filtrate was concentrated in vacuo and chromatographed on silica gel, eluting with dichloromethane:methanol concentrated ammonium hydroxide (88:10:2), to afford 502 mg (28%) of the title compound as an off-white foam.

Mp: 47–53° C.; $^1$H NMR (300 MHz, $CD_3OD$): δ 7.62 (d, J=8.2 Hz, 2H), 7.46 (d, J=8.2 Hz, 2H), 6.62 (d, J=8.2 Hz, 2H), 6.50 (s, 1H), 6.18 (d, J=4.0 Hz, 2H), 5.22–5.10 (m, 1H), 3.80 (s, 3H), 3.76 (s, 3H), 3.33–3.20 (m, 2H), 2.50–2.30 (m, 6H), 2.15 (s, 3H), 2.20–2.0 (m, 3H), 1.92–1.50 (m, 5H). $^{13}$C NMR (75 MHz, $CD_3OD$): δ 152.0, 149.8, 148.2, 143.6, 132.4, 128.0, 118.4, 112.0, 111.7, 105.6, 102.2, 79.6, 68.4, 57.6, 56.4, 55.8, 50.5, 44.6, 39.8, 35.8, 35.4, 26.2, 22.4. CI-MS: (M+1)=450 m/z.

Preparation K

4-{2-[8-(Methylamino)-3-azabicyclo[3.2.1]oct-3-yl] ethoxy}benzonitrile (i) 4-(2-Bromoethoxy)benzonitrile A mixture of 4-cyanophenol (35.7 g, 0.3 mol), $K_2CO_3$ (41.4 g, 0.3 mol) and 1,2-dibromoethane (561 g, 3.0 mol) in MeCN (450 mL) was stirred under reflux overnight. The mixture was filtered and evaporated to give 30.2 g (45%) of the sub-title compound, which was used without further purification.

(ii) tert-Butyl 3-[2-(4-Cyanophenoxy)ethyl]-3-azabicyclo [3.2.1]oct-8-yl-(methyl)carbamate A mixture of 4-(2-bromoethoxy)benzonitrile (see step (i) above; 0.94 g, 4.2 mmol), tert-butyl 3-azabicyclo[3.2.1]oct-8-yl(methyl)carbamate (Preparation D; 0.91 g, 3.8 mmol) and $K_2CO_3$ (0.79 g, 5.7 mmol) in 15 mL of dry DMF was stirred at 90° C. overnight before additional $K_2CO_3$ (1 g) was added. The mixture was diluted with 300 mL of DCM, and the mixture was washed with water. The organic layer was separated, dried with $Na_2SO_4$ and then evaporated. The crude product was purified by flash chromatography on silica gel, eluting with DCM:MeOH (10:1) containing 0.1% TEA, to yield 1.1 g (76%) of the sub-title compound.

(iii) 4-{2-[8-(Methylamino)-3-azabicyclo[3.2.1]oct-3-yl]ethoxy}-benzonitrile

Ethyl acetate (30 mL) saturated with gaseous HCl was added to a solution of tert-butyl 3-[2-(4-cyanophenoxy)ethyl]-3-azabicyclo[3.2.1]oct-8-yl-(methyl)carbamate (see step (ii) above; 1.1 g, 2.8 mmol) in ethyl acetate at 0° C. The resulting mixture was stirred for 4 h at rt. The solvent was removed in vacuo before MeCN (29 mL), water (1.5 mL) and $K_2CO_3$ (2.4 g) were added. The resulting mixture was stirred overnight before being filtered, washed with $CHCl_3$ and then concentrated in vacuo to give 0.79 g (99%) of the tide compound.

Preparation L 4-({3-[8-(Methylamino)-3-azabicyclo[3.2.1]oct-3-yl]propyl}sulfonyl)benzonitrile (i) 4-[(3-Bromopropyl)sulfanyl]benzonitrile A mixture of 4-cyanothiophenol (20.8 g, 154 mmol), 1,3-dibromopropane (155 g, 0.77 mol) and $K_2CO_3$ (21.3 g, 154 mmol) in MeCN (300 mL) was refluxed overnight. Filtration and evaporation of the solvent gave a brown oil that crystallised when treated with EtOH. The crystals were isolated by filtration to give the sub-title compound (24.5 g, 62%).

(ii) 4-[(3-Bromopropyl)sulfonyl]benzonitrile

3-Chloroperoxybenzoic acid (44.9 g of 70%, 182 mmol) was added slowly to a cooled (0° C.) solution of 4-[(3-bromopropyl)sulfanyl]-benzonitrile (see step (i) above; 23.4 g, 91 mmol) in DCM (250 mL). The mixture was then stirred at rt overnight, and the resulting precipitate filtered off. The filtrate was concentrated in vacuo to give a residue that was shown (by NMR analysis) to contain 25% sulfoxide in addition to the desired product. The residue was redissolved in DCM (250 mL), additional 3-chloroperoxybenzoic acid (5.6 g of 70%, 23 mmol) added, and the mixture stirred for 30 min. Dimethylsulfoxide (20 mmol) was added to destroy excess mCPBA before the DCM solution was washed with aqueous $NaHCO_3$, separated, dried and concentrated in vacuo. This gave the sub-title compound in 76% yield.

(iii) tert-Butyl 3-{3-[(4-cyanophenyl)sulfonyl]propyl}-3-azabicyclo[3.2.1]oct-8-yl(methyl)carbamate The sub-title compound was obtained in 70% yield (1.1 g) according to the procedure described in Preparation K(ii) above, using 4-[(3-bromo-propyl)sulfonyl]benzonitrile (see step (ii) above) in place of 4-(2-bromoethoxy)benzonitrile.

(iv) 4-({3-[8-(Methylamino)-3-azabicyclo[3.2.1]oct-3-yl]propyl}sulfonyl)benzonitrile The tide compound was obtained in 100% yield according to the procedure described in Preparation K (iii) above, using tert-butyl 3-{3-[(4-cyanophenyl)sulfonyl]propyl}-3-azabicyclo[3.2.1]oct-8-yl(methyl)carbamate (see step (iii) above) in place of tert-butyl 3-[2-(4-cyanophenoxy)ethyl]-3-azabicyclo[3.2.1]oct-8-yl(methyl)carbamate.

Preparation M

4-{2-[8-(Methylamino)-3-azabicyclo[3.2.1]oct-3-yl]ethoxy}isophthalonitrile (i) 4-(2-Bromoethoxy)isophthalonitrile The sub-tide compound was prepared in 64% yield according to the procedure described in Preparation K(i) above, using 4-hydroxyisophthalonitrile in place of 4-cyanophenol.

(ii) tert-Butyl 3-[2-(2,4-Dicyanophenoxy)ethyl]-3-azabicyclo[3.2.1]oct-8-yl(methyl)carbamate The sub-tide compound was prepared in 85% yield according to the procedure described in Preparation K(ii) above, using 4-(2-bromoethoxy)isophthalonitrile (see step (i) above) in place of 4-(2-bromoethoxy)benzonitrile.

(iii) 4-{2-[8-(Methylamino)-3-azabicyclo[3.2.1]oct-3-yl]ethoxy}isophthalonitrile The title compound was prepared in 20% yield according to the method described in Preparation K(iii) above, using tert-butyl 3-[2-(2,4-dicyanophenoxy)ethyl]-3-azabicyclo[3.2.1]oct-8-yl(methyl)carbamate in place of tert-butyl 3-[2-(4-cyanophenoxy)ethyl]-3-azabicyclo[3.2.1]oct-8-yl(methyl)carbamate.

Preparation N

4-{1-(4-Hydroxyphenoxy)-4-[8-(methylamino)-3-azabicyclo[3.2.1]oct-3-yl]butyl}benzonitrile (i) 4-{1-[4-(Tetrahydro-2H-pyran-2-yloxy)phenoxy]-3-butenyl}benzonitrile A cooled (0° C.) mixture of 4-(1-hydroxy-3-butenyl)benzonitrile (4.93 g, 28.5 mmol) and 4-(tetrahydro-2H-pyran-2-yloxy)phenol (8.3 g, 42.7 mmol) in dry THF (200 mL) was treated with tributylphosphine (8.85 mL, 42.7 mmol), followed by 1,1'-(azodicarbonyl)dipiperidine (10.77 g, 42.7 mmol). After addition was complete, the reaction mixture was stirred at 0° C. for 10 min, before being stirred at rt overnight. The precipitate of tributylphosphine oxide was removed by filtration and the filtrate was concentrated in vacuo to give 24.6 g of crude product. This was purified by chromatography on silica gel, eluting with IPA:EtOAc:heptane (5:5:90), to give 4.6 g (47%) of the subtitle compound.

(ii) 4-{4-Hydroxy-1-[4-(tetrahydro-2H-pyran-2-yloxy)phenoxy]butyl}benzonitrile

Borane-dimethylsulfide complex (3.5 mL of 2 M in ether, 7 mmol) was added dropwise to a cooled (5° C.) solution of 4-{1-[4-(tetrahydro-2H-pyran-2-yloxy)phenoxy]-3-butenyl}benzonitrile (see step (i) above; 4.6 g, 13 mmol) in dry THF over a period of 15 min. The resulting mixture was stirred at between 0 and 5° C. for 1.5 h. Stirring was then continued for a further 4 h at rt. Water (14 mL) and $NaBO_3$ (5 g) were added and the mixture stirred overnight. Ether was added and the resulting organic layer was separated, washed with water and brine, dried and then evaporated. The resulting residue was purified by chromatography on silica gel, eluting with IPA:EtOAc:heptane (5:20:70), to give 2.44 g (58%) of the sub-title compound.

(iii) 4-(4-Cyanophenyl)-4-[4-(tetrahydro-2H-pyran-2-yloxy)phenoxy]butyl Methanesulfonate A solution of 4-{4-hydroxy-1-[4-(tetrahydro-2H-pyran-2-yloxy)phenoxy]butyl}benzonitrile (see step (ii) above; 2.37 g, 6.45 mmol) and TEA (1.35 mL, 9.68 mmol) in DCM (10 mL) was cooled to −5° C. Methanesulfonyl chloride (0.65 mL, 8.38 mmol) in DCM (5 mL) was added slowly. After addition was complete, the temperature was maintained below 5° C. for 1 h before DCM and water were added. The organic layer was washed with water, dried ($Na_2SO_4$) and then evaporated to yield 2.87 g (100%) of the sub-title compound. This was used in the next step without further purification.

(iv) tert-Butyl 3-{4-(4-Cyanophenyl)-4-[4-(tetrahydro-2H-pyran-2-yloxy)phenoxy]butyl}-3-azabicyclo[3.2.1]oct-8-yl(methyl)carbamate The sub-title compound was prepared in 93.4% yield according to the procedure described in Preparation K(ii) above, using 4-(4-cyanophenyl)-4-[4-(tetrahydro-2H-pyran-2-yloxy)phenoxy]butyl methanesulfonate (see step (iii) above) and MeCN in place of 4-(2-bromoethoxy) benzonitrile and DMF, respectively.

(v) 4-{1-(4-Hydroxyphenoxy)-4-[8-(methylamino)-3-azabicyclo[3.2.1]oct-3-yl]butyl}benzonitrile The title compound was prepared in 83.4% yield according to the method described in Preparation K(iii) above, using tert-butyl 3-{4-(4-cyanophenyl)-4-[4-(tetrahydro-2H-pyran-2-yloxy)phenoxy]butyl}-3-azabicyclo-[3.2.1]oct-8-yl (methyl)carbamate (see step (iv) above) in place of tert-butyl 3-[2-(4-cyanophenoxy)ethyl]-3-azabicyclo[3.2.1]oct-8-yl (methyl)carbamate.

Preparation O

Methyl (1S)-2-(4-Cyanophenoxy)-1-{[8-(methylamino)-3-azabicyclo[3.2.1]oct-3-yl]methyl}ethylcarbamate (i) 4-[(2R)-Oxiranylmethoxy]benzonitrile The title compound was prepared according to the procedure described in Preparation E(i) above, using S-epichlorohydrin in place of epichlorohydrin.

(ii) 4-{[(2R)-3-Amino-2-hydroxypropyl]oxy}benzonitrile

4-[(2R)-Oxiranylmethoxy]benzonitrile (see step (i) above; 14.65 g, 83.6 mmol) was mixed with $NH_4OH$ (conc., 64 mL) and 87 mL of isopropanol. The mixture was stirred at rt for 18 h. The reaction mixture was then filtered and evaporated to give 14.6 g (91%) of the sub-title compound as a white solid.

(iii) Benzyl (2R)-3-(4-Cyanophenoxy)-2-hydroxypropylcarbamate

A mixture of 4{[(2R)-3-amino-2-hydroxypropyl]oxy}benzonitrile (see step (ii) above; 3.4 g, 17.7 mmol), TEA (2.69 g, 26.6 mmol) and $CHCl_3$ (20 mL) was cooled to 0° C. before N-(benzyloxycarbonyloxy)succinimide (4.86 g, 19.5 mol) in $CHCl_3$ (15 mL) was added slowly. The mixture was allowed to reach rt, and was stirred at that temperature overnight. The solvent was evaporated to give a residue that was dissolved in DCM. This solution was washed with water and brine and then dried ($Na_2SO_4$). Evaporation of the solvent gave 5.79 g (100%) of the sub-title compound.

(iv) (1R)-2-{[(Benzyloxy)carbonyl]amino}-1-[(4-cyanophenoxy)methyl]ethyl Methanesulfonate 4-(Dimethylamino)pyridine (0.22 g, 1.77 mmol) was added to a solution of benzyl (2R)-3-(4-cyanophenoxy)-2-hydroxypropylcarbamate (see step (iii) above; 5.79 g, 17.7 mmol) in pyridine (15 mL). The mixture was cooled to 0° C., and methanesulfonyl chloride (2.23 g, 19.5 mmol) was added slowly at 0° C. The mixture was allowed to reach rt, at which temperature it was then stirred for 4 h. The solvent was evaporated. DCM (100 mL) was added, washed with water, 1 N $H_2SO_4$ and brine, dried ($Na_2SO_4$) and evaporated giving 6.0 g (84%) of a yellow oil.

(v) Benzyl (2S)-2-[(4-Cyanophenoxy)methyl]-1-aziridinecarboxylate

A solution of NaOH in water (11 mL of 50 wt. %) was added under vigorous stirring to a solution of (1R)-2-{[(benzyloxy)carbonyl]amino}-1-[(4-cyanophenoxy)methyl]ethyl methanesulfonate (see step (iv) above; 5.7 g, 14.1 mmol) and tetrabutylammonium hydrogensulfate (0.6 g, 1.7 mmol) in DCM (34 mL). The mixture was stirred for 1 h before water (200 mL) and ether (200 mL) were added. The organic phase was washed with water and then dried. The solvents were evaporated and the resulting residue was purified by chromatography (DCM eluant) to yield 3.0 g (69%) of the sub-title compound.

vi) Benzyl (1S)-2-{8-[(tert-Butoxycarbonyl)(methyl) amino]-3-azabicyclo[3.2.1]oct-3-yl}-1-[(4-cyanophenoxy) methyl]ethylcarbamate Benzyl (2S)-2-[(4-cyanophenoxy)methyl]-1-aziridinecarboxylate (see step v) above; 1.3 g, 4.2 mmol) and tert-butyl 3-azabicyclo[3.2.1]oct-8-yl-methyl) carbamate (Preparation D; 1.1 g, 4.6 mmol) were mixed in IPA (15 mL) and stirred at 60° C. overnight. The solvent was then evaporated to give a residue that was purified by chromatography on silica gel, eluting with DCM:MeOH (100:3), to give 1.9 g (82%) of the sub-title compound.

(vii) tert-Butyl 3-[(2S)-2-Amino-3-(4-cyanophenoxy) propyl]-3-azabicyclo[3.2.1]oct-8-yl(methyl)carbamate Benzyl (1S)-2-{8-[(tert-butoxycarbonyl)(methyl)amino]-3-azabicyclo[3.2.1]oct-3-yl}-1-[(4-cyanophenoxy)methyl] ethylcarbamate (see step (vi) above; 1.8 g, 3.3 mmol) was dissolved in ethanol (50 mL of 95%). The solution was hydrogenated over 5% Pd/C for 1 h, after which the mixture was filtered through Celite®. The filtrate was concentrated in vacuo to give 1.3 g (95%) of the sub-title compound.

(viii) Methyl (1S)-2-{8-[(tert-butoxycarbonyl)(methyl) amino]-3-azabicyclo[3.2.1]oct-3-yl}-1-[(4-cyanophenoxy) methyl]ethylcarbamate Methyl chloroformate (0.24 mL, 3.2 mmol) was added, at 0° C., to a mixture of tert-butyl 3-[(2S)-2-amino-3-(4-cyanophenoxy)propyl]-3-azabicyclo[3.2.1]oct-8-yl(methyl) carbamate (see step (vii) above; 1.2 g, 2.9 mmol) and TEA (1.2 mL, 9 mmol) in DCM (30 mL). The mixture was allowed to reach rt over the course of 3 h, after which time a saturated solution of $Na_2CO_3$ was added. The organic phase was separated, dried and evaporated to give a crude product that was purified by chromatography on silica gel. This gave 0.6 g (45%) of the sub-title compound.

(ix) Methyl (1S)-2-(4-Cyanophenoxy)-1-{[8-(methylamino)-3-azabicyclo[3.2.1]oct-3-yl]methyl}ethylcarbamate The title compound was prepared in 87% yield according to the procedure described in Preparation K(iii) above, using methyl (1S)-2-{8-[(tert-butoxycarbonyl)(methyl)amino]-3-azabicyclo[3.2.1]oct-3-yl}-1-[(4-cyanophenoxy)methyl] ethylcarbamate (see step (viii) above) in place of tert-butyl 3-[2-(4-cyanophenoxy)ethyl]-3-azabicyclo[3.2.1]oct-8-yl (methyl)carbamate.

Preparation P tert-Butyl (1S)-2-(4-Cyanophenoxy)-1-{[8-(methylamino)-3-azabicyclo[3.2.1]oct-3-yl]methyl}ethylcarbamate (i) tert-Butyl (2R)-3-(4-Cyanophenoxy)-2-hydroxypropylcarbamate 4-{[(2R)-3-amino-2-hydroxypropyl]oxy}benzonitrile (Preparation O(ii); 6.8 g, 3.5 mmol) was dissolved in a mixture of THF/water (8:1). The solution was cooled with an ice bath, and di-tert-butyl dicarbonate (7.7 g, 3.5 mmol) was added in portions. The mixture was stirred at rt overnight before the solvents were evaporated and DCM added. The resulting solution was washed with water, dried ($Na_2SO_4$) and evaporated to give 9.2 g of the sub-title compound.

(ii) (1R)-2-[(tert-Butoxycarbonyl)amino]-1-[(4-cyanophenoxy)methyl]ethyl Methanesulfonate The sub-title compound was prepared in 100% yield according to the procedure described in Preparation O(iv) above, using tert-butyl (2R)-3-(4-cyanophenoxy)-2-hydroxypropylcarbamate (see step (i) above) in place of benzyl (2R)-3-(4-cyanophenoxy)-2-hydroxypropylcarbamate.

(iii) tert-Butyl (2S)-2-[(4-Cyanophenoxy)methyl]-1-aziridinecarboxylate

The sub-title compound was prepared according to the procedure described in Preparation O(v) above, using (1R)-2-[(tert-butoxycarbonyl)amino]-1-[(4-cyanophenoxy)methyl]ethyl methanesulfonate (see step (ii) above) in place of (1R)-2-{[(benzyloxy)carbonyl]amino}-1-[(4-cyanophenoxy)methyl]ethyl methanesulfonate.

(iv) tert-Butyl Methyl[3-(2,2,2-trifluoroacetyl)-3-azabicyclo[3.2.1]oct-8-yl]carbamate Trifluoroacetic anhydride (10.5 g, 50 mmol) was added dropwise to a cooled (0° C.) mixture of tert-butyl 3-azabicyclo[3.2.1]oct-8-yl(methyl)carbamate (Preparation D; 11.1 g, 46 mmol), TEA (5.6 g, 55 mmol) and toluene (120 mL). The mixture was stirred for 3 h, and then evaporated. The resulting residue was dissolved in DCM and the resulting solution was washed with 1 M HCl (cold). The organic layer was separated, dried and evaporated to yield 14.8 g (96%) of the sub-title compound.

(v) 2,2,2-Trifluoro-1-[8-(methylamino)-3-azabicyclo[3.2.1]oct-3-yl]-1-ethanone

Ethyl acetate (100 mL) saturated with HCl (g) was added, at 0° C., to a solution of tert-butyl methyl[3-(2,2,2-trifluoroacetyl)-3-azabicyclo[3.2.1]oct-8-yl]carbamate (see step (iv) above; 5 g, 15 mmol) in ethyl acetate (50 mL). The mixture was allowed to reach rt over the course of 3 h, after which time the solvent was evaporated. This gave 4 g (100%) of the sub-tide compound hydrochloride salt.

(vi) 1-{8-[Benzyl(methyl)amino]-3-azabicyclo[3.2.1]oct-3-yl}-2,2,2-trifluoro-1-ethanone A mixture of 2,2,2-trifluoro-1-[8-(methylamino)-3-azabicyclo[3.2.1]oct-3-yl]-1-ethanone (see step (v) above; 4.5 g, 16 mmol), benzylchloride (3.0 g, 16 mmol) and TEA (6.6 mL) in MeCN (50 mL) was stirred at 60° C. overnight. The mixture was evaporated and then DCM and water were added. The organic phase was washed with $NaHCO_3$ solution, dried ($Na_2SO_4$) and then evaporated. The resulting crude product was purified by chromatography on silica gel (DCM eluant) to give 2.2 g (42%) of the sub-title compound.

(vii) N-Benzyl-N-methyl-3-azabicyclo[3.2.1]octan-8-amine

A mixture of 1-{8-[benzyl(methyl)amino]-3-azabicyclo[3.2.1]oct-3-yl}-2,2,2-trifluoro-1-ethanone (see step (vi) above; 2.1 g, 6.4 mmol) and $K_2CO_3$ (3 g, 21.7 mmol) in MeOH/water (110 mL of 10:1) was stirred at rt overnight and then evaporated. DCM and water were added and the layers separated. The water layer was extracted with DCM (3×). The combined organic layers were dried and evaporated to give 1.2 g (81%) of the sub-title compound.

(viii) tert-Butyl (1S)-2-{8-[Benzyl(methyl)amino]-3-azabicyclo[3.2.1]oct-3-yl}-1-[(4-cyanophenoxy)methyl]ethylcarbamate A mixture of tert-butyl (2S)-2-[(4-cyanophenoxy)methyl]-1-aziridinecarboxylate (see step (iii) above; 1.26 g, 4.6 mmol) and N-benzyl-N-methyl-3-azabicyclo[3.2.1]octan-8-amine (see step (vii) above; 1.05 g, 4.6 mmol) in IPA (15 mL) was stirred at 60° C. overnight. The solvent was evaporated and the residue purified by chromatography on silica gel, eluting with DCM:MeOH (20:1). This gave 1.8 g (78%) of the subtitle compound (ix) tert-Butyl (1S)-2-(4-Cyanophenoxy)-1-{[8-(methylamino)-3-azabicyclo[3.2.1]oct-3-yl]methyl}ethylcarbamate A mixture of tert-butyl (1S)-2-{8-[benzyl(methyl)amino]-3-azabicyclo[3.2.1]oct-3-yl}-1-[(4-cyanophenoxy)methyl]ethylcarbamate (0.8 g, 1.6 mmol), 1 M HCl (0.8 mL) and MeOH (30 mL) was hydrogenated over 5% Pd/C. The reaction was stopped when the amount of $H_2$ calculated for complete reaction had been consumed. The mixture was filtered through silica and the filtrate evaporated. The resulting crude product was purified on silica gel, eluting with DCM:ammoniacal methanol (9:1), to yield 0.4 g (61%) of the title compound.

Preparation Q 2-(Acetyloxy)-1,1-dimethylethyl 1H-Imidazole-1-carboxylate

A mixture of 2-hydroxy-2-methylpropyl acetate (3.35 g, 25.3 mmol) and 1,1'-carbonyldiimidazole (4.11 g, 25.3 mmol) in DCM was stirred for 8 h at rt. The mixture was then transferred to a closed vessel and heated to 100° C. overnight. The mixture was concentrated in vacuo before ether and water were added. The organic phase was separated, dried and concentrated in vacuo. The resulting residue was purified by chromatography on silica gel, eluting with THF:heptane (1:1), to give the title compound in 20% yield.

Preparation R

1-Cyano-1-methylethyl 1H-Imidazole-1-carboxlate

A mixture of 1,1'-carbonyldiimidazole (5 g, 31 mmol) and 2-hydroxy-2-methylpropanenitrile (2.6 g, 31 mmol) in DCM was stirred at rt overnight. Water was added and the organic layer was separated, dried ($Na_2SO_4$) and concentrated in vacuo. The resulting residue was purified by chromatography on silica gel, eluting with ethyl acetate, to give 2.7 g (50%) of the title compound.

Preparation S 2-(4-Morpholinyl)ethyl 1H-Imidazole-1-carboxylate

A mixture of 1,1'-carbonyldiimidazole (6.5 g, 40 mmol) and 2-(4-morpholinyl)-1-ethanol (5.0 g, 38.1 mmol) in DCM (200 mL) was stirred for 22 h at rt. Ether (400 mL) was added and the mixture was washed with water. The water layer was then extracted with DCM. The combined organic layers were dried over $Na_2SO_4$ and evaporated to give 6.0 g (70%) of the tide compound.

Preparation T 2-(4-Pyridinyl)ethyl 1H-Imidazole-1-carboxylate

The title compound was prepared in 100% yield according to the procedure described in Preparation S above, using 2-(4-pyridinyl)-1-ethanol in place of 2-(4-morpholinyl)-1-ethanol.

Preparation U

N-[2-(2-Methoxyethoxy)ethyl]-1H-imidazole-1-carboxamide

The title compound was prepared in 40% yield according to the procedure described in Preparation S above, using 2-(2-methoxyethoxy)ethylamine in place of 2-(4-morpholinyl)-1-ethanol.

Preparation V 2-(4-Acetyl-1-piperazinyl)ethyl 1H-Imidazole-1-carboxylate (i) 1-[4-(2-Hydroxyethyl)-1-piperazinyl]-1-ethanone A solution of 2-(1-piperazinyl)-1-ethanol (6.5 g, 0.05 mol) in DCM (5 mL) was treated with acetic acid anhydride (5.1 g, 0.05 mol), added dropwise. During addition, the reaction temperature rose from 22 to 60° C. The reaction mixture was evaporated several times with toluene to yield 5.6 g (65%) of the sub-title compound.

(ii) 2-(4-Acetyl-1-piperazinyl)ethyl 1H-Imidazole-1-carboxylate

A solution of 1,1'-carbonyldiimidazole (5 g, 31 mmol) in DCM (200 mL) was treated with a solution of 1-[4-(2-hydroxyethyl)-1-piperazinyl]-1-ethanone (see step (i) above; 5 g, 29 mmol) in DCM (50 mL). The reaction mixture was stirred at rt overnight before water was added. The layers were separated, and the organic layer was washed with water, dried and concentrated in vacuo to yield 7.4 g (96%) of the title compound.

Preparation W

1-[4-(3-Bromopropyl)-1-piperazinyl]-1-ethanone

A mixture of 1-(1-piperazinyl)-1-ethanone (6.7 g, 0.052 mol), dibromopropane (330 mL, excess) and $K_2CO_3$ (10.2 g, 0.079 mol) was stirred at rt for 4 h. The mixture was washed with 4×100 mL of water, and the organic phase (diluted with DCM) was acidified with aqueous hydrobromic acid (7 mL of 62% HBr dissolved in 150 mL of water). The organic layer was separated and washed with water (2×50 mL). The combined water layers were extracted with ether, neutralised (to pH 7) with 13 mL of 10 M NaOH, and then extracted with DCM. The combined organic layers were dried and concentrated in vacuo to give 4.1 g (32%) of the title compound.

Preparation X 3-(Ethylsulfonyl)propyl 4-Methylbenzenesulfonate
(i) 3-(Ethylsulfonyl)-1-propanol A solution of 3-(ethylthio)-1-propanol (13 g, 0.11 mol) in acetic acid (40 mL) was treated with $H_2O_2$ (30% in water, 12.2 g, 0.11 mol), added dropwise. The mixture was stirred for 2 h at rt, before being concentrated in vacuo. NMR analysis showed that the resulting residue consisted of 40% of the desired product and 60% of the corresponding O-acetate. The acetate was hydrolysed by dissolving the reaction mixture in 200 mL of methanol and adding 3 g of NaOH (dissolved in a small amount of water). This mixture was stirred overnight at rt, then concentrated in vacuo. The resulting crude product was dissolved in DCM, and insoluble material was filtered off. The DCM was removed by evaporation to give 13.4 g (88%) of the sub-title compound.

(ii) 3-(Ethylsulfonyl)propyl 4-Methylbenzenesulfonate

A mixture of 3-(ethylsulfonyl)-1-propanol (see step (i) above; 13.4 g, 88 mmol) and p-toluenesulfonyl chloride (16.8 g, 88 mmol) in DCM (150 mL) was treated with TEA (13.4 g, 132 mmol), added dropwise. The resulting mixture was stirred at rt for 3 h before being washed with aqueous ammonium chloride solution. The organic layer was then separated, dried and concentrated in vacuo. The product was crystallised from ether containing a small amount of DCM to yield 17.9 g (66%) of the title compound.

The following intermediates were either commercially available or were prepared according to published methods:

3,4-dimethoxyphenethyl methanesulfonate;
hexyl isocyante;
ethyl isocyante;
butanoyl chloride;
1-butanesulfonyl chloride;
1-chloropinacoline;
4-isocyanato-3,5-dimethylisoxazole;
p-toluenesulfonyl isocyanate;
4-methoxyphenyl isocyanate;
2-isocyanatotetrahydro-2H-pyran;
isopropyl isocyanate;
3,4-difluorophenyl isocyanate;
butyl isocyanate;
1-(isocyanatomethyl)cyclopropane;
2-(acetylamino)-4-methyl-1,3-thiazole-5-sulfonyl chloride;
4-nitrobenzenesulfonyl chloride;
N-acetylsulfanilyl chloride;
isopropylsulfonyl chloride;
3,4-dimethoxybenzenesulfonyl chloride;
5-chloro-1,3-dimethylpyrazole4-sulfonyl chloride;
1,1-dioxo-2,5-dihydro-1-thiophene-3-sulfonyl chloride;
ethanesulfonyl chloride;
ethyl chloroformate;
2-butyn-1-chloroformate;
2-methoxyethyl chloroformate;
hydantoin-5-acetic acid;
2-{[2-(acetylamino)acetyl]amino}acetic acid;
methoxyacetic acid;
DL-glyceric acid;
pyrrole-2-carboxylic acid;
2-methylpropionic acid;
benzofurazan-5-carboxylic acid;
2-hydroxy-3-butynoic acid;
3-(tert-butyl)-1-methyl-1H-pyrazole-5-carboxylic acid;
(chloromethyl)cyclopropane;
2-bromo-1-(2,3-dihydro-1,4-benzodioxin-6-yl)-1-ethanone;
N-isopropyl chloroacetamide;
1-bromo-2-(2-methoxyethoxy)ethane;
4-fluorobenzyl bromide;
2-bromo-4'-methoxyacetophenone;
4-(trifluoromethylthio)phenyl isocyanate;
3-(methylsulfonyl)propyl-1-choroformate; and
3-methylbutyric acid.

Synthesis of Compounds of Formula I

Example 1 tert-Butyl 8-{[3-(4-Cyanoanilino)propyl](methyl) amino}-3-azabicyclo[3.2.1]octane-3-carboxylate A mixture of 4-({3-[3-azabicyclo[3.2.1]oct-8-yl(methyl) amino]propyl}amino)benzonitrile (Preparation H; 170 mg, 0.569 mmol) and di-tert-butyldicarbonate (124 mg, 0.569 mmol) in dichloromethane (3.0 mL) was stirred for 2 h at 25° C. under nitrogen. The mixture was concentrated in vacuo and the residue chromatographed on silica gel, eluting with ethyl acetate:dichloromethane (1:2), to yield 90 mg (40%) of the title compound as a colorless oil.

$^1$H NMR (300 MHz, CDCl$_3$): δ 7.40 (d, J=8.2 Hz, 2H), 6.50 (d, J=8.2 Hz, 2H), 5.45 (s, 1H), 3.68–3.60 (m, 1H), 3.52–3.40 (m, 1H), 3.32–3.10 (m, 4H), 2.60 (s, 2H), 2.30 (s, 3H), 2.22–2.15 (m, 3H), 1.92–1.60 (m, 6H), 1.45 (s, 9H). $^{13}$C NMR (75 MHz, CDCl$_3$): δ 156.4, 151.6, 133.6, 120.6, 112.0, 108.1, 79.4, 67.8, 54.2, 45.0, 44.0, 42.7, 39.8, 35.6, 28.4, 26.0, 25.4. CI-MS: (M+1)=399 m/z.

Example 2 tert-Butyl 8-[[3-(4-Cyanophenoxy)-2-hydroxypropyl](methyl)amino]-3-azabicyclo[3.2.1]octane-3-carboxylate A mixture of 4-{3-[3-azabicyclo[3.2.1]oct-8-yl(methyl)amino]-2-hydroxypropoxy}benzonitrile (Preparation E; 229 mg, 0.726 mmol) and di-tert-butyldicarbonate (158 mg, 0.726 mmol) in dichloromethane (3.0 mL) was stirred for 2 h at 25° C. under nitrogen. The mixture was concentrated in vacuo and the residue chromatographed on silica gel, eluting with ethyl acetate:dichloromethane (1:2), to yield 70 mg (25%) of the tide compound as a colorless oil.

$^1$H NMR (300 MHz, CDCl$_3$): δ 7.58 (d, J=8.2 Hz, 2H), 6.97 (d, J=8.2 Hz, 2H), 4.30–4.16 (m, 1H), 4.12–4.0 (m, 2H), 3.70–3.10 (m, 5H), 2.82–2.70 (m, 1H), 2.52–2.10 (m, 4H), 2.30 (s, 3H), 1.80–1.52 (m, 4H), 1.45 (s, 9H). $^{13}$C NMR (75 MHz, CDCl$_3$): δ 162.4, 156.5, 134.0, 119.5, 115.6, 104.4, 79.5, 70.6, 68.0, 66.0, 57.7, 45.0, 43.8, 40.4, 36.8, 36.2, 28.5, 27.8. CI-MS: (M+1)=416 m/z.

Example 3

N-{3-[2-(4-Cyanophenoxy)ethyl]-3-azabicyclo[3.2.1]oct-8-yl}-N'-ethyl-N-methylurea A solution of ethyl isocyanate (0.8 mL, 9.66 mmol) in DCM (3 mL) was added dropwise, at 0° C., to a mixture of 4-{2-[8-(methylamino)-3-azabicyclo[3.2.1]oct-3-yl]ethoxy}benzonitrile (Preparation K; 2.5 g, 8.76 mmol) and MeCN (50 mL). The mixture was stirred at rt for 3 h, K$_2$CO$_3$ (2 g, 14.4 mmol) was added and the mixture was stirred for a further 2 h. Filtration and evaporation gave 2.96 g of crude product. This was purified twice by chromatography on silica gel, the first time eluting with a gradient of EtOAc:MeOH:ammoniacal methanol (10:1:0 to 10:0:1), and the second time eluting with DCM:MeOH:TEA (190:10:1). This gave 2.3 g (71.4%) of the title compound.

$^{13}$C NMR (CD$_3$OD): δ 15.84, 26.98, 36.35, 36.54, 38.70, 55.02, 57.88, 61.99, 67.68, 104.67, 116.66, 120.11, 135.16, 163.68, 163.94. MS(ES): (M+1)=357.0 m/z.

Example 4

N-{3-[3-(4-Cyanoanilino)propyl]-3-azabicyclo[3.2.1]oct-8-yl}-N-methyl-1-butanesulfonamide A solution of 1-butanesulfonyl chloride (39.1 mg, 0.25 mmol) in MeCN (2 mL) was added to a solution of 4-({3-[8-(methylamino)-3-azabicyclo[3.2.1]oct-3-yl]propyl}amino)benzonitrile (Preparation G; 74.6 mg, 0.25 mmol) in CHCl$_3$ (0.5 mL). K$_2$CO$_3$ was added and the mixture was stirred at rt for 24 h. The mixture was filtered through a silica plug (500 mg), which plug was then eluted with MeCN:CHCl$_3$ (80:20; 3×2.5 mL), followed by CHCl$_3$:MeOH (95:5), to give the title compound in 35% yield.

MS(ES): (M+1)=419.2 m/z.

Example 5

Ethyl 3-[3-(4-Cyanoanilino)propyl]-3-azabicyclo[3.2.1]oct-8-yl(methyl)carbamate

A mixture of 4-({3-[8-(methylamino)-3-azabicyclo[3.2.1]oct-3-yl]propyl}amino)benzonitrile (Preparation G; 74.6 mg, 0.25 mmol) and ethyl chloroformate (29.8 mg, 0.27 mmol) in DMF (2.5 mL) was stirred at rt for 24 h. Mass spectroscopic analysis showed that the amine starting material had not been totally consumed, and so additional ethyl chloroformate (50 μL) was added. The mixture was stirred overnight, after which time it was concentrated in vacuo. The resulting residue was dissolved in a mixture of DCM (0.5 mL) and MeCN (2 mL). K$_2$CO$_3$ (100 mg, 0.7 mmol) was added and the mixture stirred for 4 h. Filtration of the mixture and evaporation of the filtrate gave a residue that was dissolved in CHCl$_3$ (1 mL). The solution was filtered through an ion-exchange solid-phase extraction plug (CBA, 2 g). The source flask was washed with additional CHCl$_3$ (0.75 mL), which was then added to the extraction plug, and eluted as fraction 1. The plug was then eluted with CHCl$_3$:MeOH:TEA (8:1:1; 4×2 mL) to give further fractions that were found not to contain any product. Fraction 1 was then added to a silica plug, which was eluted with CHCl$_3$:MeCN (4:1; 3×2.5 mL). Evaporation of the fractions collected gave 79.6 mg (85.9%) of the title compound.

MS(ES): (M+1)=371.5 m/z.

Example 6

N-{3-[3-(4-Cyanoanilino)propyl]-3-azabicyclo[3.2.1]oct-8-yl}-N,3-dimethylbutanamide 1,3-Dicyclohexylcarbodiimide on N-methylpolystyrene (0.67 g of 2.39 mmol/g, 1.74 mmol) was added to a solution of 4-({3-[8-(methylamino)-3-azabicyclo[3.2.1]oct-3-yl]propyl}amino)benzonitrile (Peparation G; 74.6 mg, 0.25 mmol) in DMF (3.0 mL). A solution of 3-methylbutyric acid (105.0 mg, 1.02 mmol) in DCM (1.0 mL) was added, and the mixture was stirred overnight at rt, followed by a further 72 h at 50° C. Polystyrene isocyanate (150 mg) and DCM (1.5 mL) were added, and this mixture was stirred for 1.5 h. K$_2$CO$_3$ (75 mg) was added and the mixture stirred for an additional 5 h. The solvents were evaporated and DCM (3 mL) was added to the resulting residue. This mixture was added to an ion-exchange solid-phase extraction plug (CBA). The plug was washed with DCM:MeCN (4:1; 10 mL). The product was then eluted with DCM:MeOH:TEA (90:5:5; 7.5 mL) to give 75 mg (70.9%) of the title compound.

MS(ES): 383.3 m/z.

Example 7

The following compounds were prepared, from appropriate intermediates (such as those described hereinbefore), according to or by analogy with methods described herein and/or by standard solid or solution phase combinatorial chemistry techniques (mass spectra of the compounds, where recorded, are in brackets: unless otherwise stated, the values refer to (M+1) ions measured by electrospray):

4-{3-[(3-butyryl-3-azabicyclo[3.2.1]oct-8-yl)(methyl)amino]-2-hydroxypropoxy}benzonitrile (m/z=386.2);

4-{3-[[3-(butylsulfonyl)-3-azabicyclo[3.2.1]oct-8-yl](methyl)amino]-2-hydroxypropoxy}benzonitrile (m/z=436.2);

4-{3-[[3-(3,3-dimethyl-2-oxobutyl)-3-azabicyclo[3.2.1]oct-8-yl](methyl)amino]-2-hydroxypropoxy}benzonitrile (m/z=414.3);

4-{3-[[3-(3,4-dimethoxyphenethyl)-3-azabicyclo[3.2.1]oct-8-yl](methyl)amino]-2-hydroxypropoxy}benzonitrile (m/z=480.3);

8-[[3-(4-cyanoanilino)propyl](methyl)amino]-N-hexyl-3-azabicyclo[3.2.1]octane-3-carboxamide (m/z=426.3);

8-[[3-(4-cyanoanilino)propyl](methyl)amino]-N-ethyl-3-azabicyclo[3.2.1]octane-3-carboxamide (m/z=370.3);

4-({3-[(3-butyryl-3-azabicyclo[3.2.1]oct-8-yl)(methyl)
amino]propyl}amino)benzonitrile (m/z=369.3);

4-({3-[[3-(butylsulfonyl)-3-azabicyclo[3.2.1]oct-8-yl]
(methyl)amino]propyl}amino)benzonitrile (m/z=419.2);

4-({3-[[3-(3,3-dimethyl-2-oxobutyl)-3-azabicyclo[3.2.1]
oct-8-yl](methyl)amino]propyl}amino)benzonitrile
(m/z=397.3);

4-({3-[[3-(3,4-dimethoxyphenethyl)-3-azabicyclo[3.2.1]
oct-8-yl](methyl)amino]propyl}amino)benzonitrile
(m/z=463.3);

8-[[4-(4-cyanophenyl)-4-(3,4-dimethoxyphenoxy)butyl]
(methyl)amino]-N-hexyl-3-azabicyclo[3.2.1]octane-3-
carboxamide (m/z=577.4);

8-[[4-(4-cyanophenyl)-4-(3,4-dimethoxyphenoxy)butyl]
(methyl)amino]-N-ethyl-3-azabicyclo[3.2.1]octane-3-
carboxamide (m/z=521.3);

4-[4-[(3-butyryl-3-azabicyclo[3.2.1]oct-8-yl)(methyl)
amino]-1-(3,4-dimethoxyphenoxy)butyl]benzonitrile
(m/z=520.3);

4-[4-[[3-(butylsulfonyl)-3-azabicyclo[3.2.1]oct-8-yl]
(methyl)amino]-1-(3,4-dimethoxyphenoxy)butyl]
benzonitrile (m/z=570.3);

4-{1-(3,4-dimethoxyphenoxy)-4-[[3-(3,3-dimethyl-2-
oxobutyl)-3-azabicyclo[3.2.1]oct-8-yl](methyl)amino]
butyl}benzonitrile (m/z=548.3);

4-[4-[[3-(3,4-dimethoxyphenethyl)-3-azabicyclo[3.2.1]
oct-8-yl](methyl)amino]-1-(3,4-dimethoxyphenoxy)
butyl]benzonitrile (m/z=614.4);

N-{3-[3-(4-cyanophenoxy)-2-hydroxypropyl]-3-
azabicyclo[3.2.1]oct-8-yl}-N-hexyl-N-methylurea
(m/z=443.3);

N-{3-[3-(4-cyanophenoxy)-2-hydroxypropyl]-3-
azabicyclo[3.2.1]oct-8-yl}-N-ethyl-N-methylurea
(m/z=387.2);

N-{3-[3-(4-cyanophenoxy)-2-hydroxypropyl]-3-
azabicyclo[3.2.1]oct-8-yl}-N-methylbutanamide (m/z=386.2);

4-(3-{8-[(3,3-dimethyl-2-oxobutyl)(methyl)amino]-3-
azabicyclo[3.2.1]oct-3-yl}-2-hydroxypropoxy)
benzonitrile (m/z=414.3);

N-{3-[3-(4-cyanoanilino)propyl]-3-azabicyclo[3.2.1]oct-
8-yl}-N'-hexyl-N-methylurea (m/z=426.3);

N-{3-[3-(4-cyanoanilino)propyl]-3-azabicyclo[3.2.1]oct-
8-yl}-N'-ethyl-N-methylurea (m/z=370.3);

N-{3-[3-(4-cyanoanilino)propyl]-3-azabicyclo[3.2.1]oct-
8-yl}-N-methyl-butanamide (m/z=369.3);

4-[(3-{8-[(3,3-dimethyl-2-oxobutyl)(methyl)amino]-3-
azabicyclo[3.2.1]oct-3-yl}propyl)amino]benzonitrile
(m/z=397.3);

4-[(3-{8-[(3,4-dimethoxyphenethyl)(methyl)amino]-3-
azabicyclo[3.2.1]oct-3-yl}propyl)amino]benzonitrile
(m/z=463.3);

N-{3-[4-(4-cyanophenyl)-4-(3,4-dimethoxyphenoxy)
butyl]-3-azabicyclo[3.2.1]oct-8-yl}-N'-hexyl-N-
methylurea (m/z=577.4);

N-{3-[4-(4-cyanophenyl)-4-(3,4-dimethoxyphenoxy)
butyl]-3-azabicyclo[3.2.1]oct-8-yl}-N-ethyl-N-
methylurea (m/z=521.3);

N-{3-[4-(4-cyanophenyl)-4-(3,4-dimethoxyphenoxy)
butyl]-3-azabicyclo[3.2.1]oct-8-yl}-N-
methylbutanamide (m/z=520.3);

N-{3-[4-(4-cyanophenyl)-4-(3,4-dimethoxyphenoxy)
butyl]-3-azabicyclo[3.2.1]oct-8-yl}-N-methyl-1-
butanesulfonamide (m/z=570.3);

4-(1-(3,4-dimethoxyphenoxy)-4-{8-[(3,3-dimethyl-2-
oxobutyl)(methyl)amino]-3-azabicyclo[3.2.1]oct-3-
yl}butyl)benzonitrile (m/z=548.3);

4-[4-{8-[(3,4-dimethoxyphenethyl)(methyl)amino]-3-
azabicyclo[3.2.1]oct-3-yl}-1-(3,4-dimethoxyphenoxy)
butyl]benzonitrile (m/z=614.4);

N-{3-[3-(4-cyanophenoxy)-2-hydroxypropyl]-3-
azabicyclo[3.2.1]oct-8-yl}-N-methyl-N'-tetrahydro-
2H-pyran-2-ylurea (m/z=443);

N-{3-[3-(4-cyanophenoxy)-2-hydroxypropyl]-3-
azabicyclo[3.2.1]oct-8-yl}-N'-(cyclopropylmethyl)-N-
methylurea (m/z=413);

3-[3-(4-cyanoanilino)propyl]-8-[methyl({[(4-
methylphenyl)sulfonyl]-amino}carbonyl)amino]-3-
azabicyclo[3.2.1]octane (ES (M-1): m/z=494);

N-{3-[3-(4-cyanoanilino)propyl]-3-azabicyclo[3.2.1]oct-
8-yl}-N'-(cyclo-propylmethyl)-N-methylurea (m/z=397);

N-{3-[3-(4-cyanoanilino)propyl]-3-azabicyclo[3.2.1]oct-
8-yl}-N'-isopropyl-N-methylurea (m/z=384);

N'-butyl-N-{3-[3-(4-cyanoanilino)propyl]-3-azabicyclo
[3.2.1]oct-8-yl}-N-methylurea (ES (M-1): m/z=396);

4-(3-{8-[(3,4-dimethoxyphenethyl)(methyl)amino]-3-
azabicyclo[3.2.1]oct-3-yl}-2-hydroxypropoxy)
benzonitrile (m/z=480.3);

3-[3-(4-cyanophenoxy)-2-hydroxypropyl]-8-[methyl({
[(4-methylphenyl)sulfonyl]amino}carbonyl)amino]-3-
azabicyclo[3.2.1]octane (ES (M-1): m/z=511);

N-{3-[3-(4-cyanophenoxy)-2-hydroxypropyl]-3-
azabicyclo[3.2.1]oct-8-yl}-N'-(3,4-difluorophenyl)-N-
methylurea (m/z=471);

N-{3-[3-(4-cyanoanilino)propyl]-3-azabicyclo[3.2.1]oct-
8-yl}-N'-(4-methoxyphenyl)-N-methylurea (m/z=448);

N-{3-[3-(4-cyanoanilino)propyl]-3-azabicyclo[3.2.1]oct-
8-yl}-N'-(3,4-difluorophenyl)-N-methylurea (m/z=454);

N-{3-[2-(4-cyanophenoxy)ethyl]-3-azabicyclo[3.2.1]oct-
8-yl}-N'-(3,5-dimethyl-4-isoxazolyl)-N-methylurea
(m/z=424);

N-{3-[2-(4-cyanophenoxy)ethyl]-3-azabicyclo[3.2.1]oct-
8-yl}-N'-(4-methoxyphenyl)-N-methylurea (m/z=435);

N-{3-[2-(4-cyanophenoxy)ethyl]-3-azabicyclo[3.2.1]oct-
8-yl}-N-methyl-N'-tetrahydro-2H-pyran-2-ylurea
(m/z=413);

N-{3-[2-(4-cyanophenoxy)ethyl]-3-azabicyclo[3.2.1]oct-
8-yl}-N'-(cyclopropylmethyl)-N-methylurea (m/z=383);

N-{3-[2-(4-cyanophenoxy)ethyl]-3-azabicyclo[3.2.1]oct-
8-yl}-N'-isopropyl-N-methylurea (m/z=371);

N-{3-[2-(4-cyanophenoxy)ethyl]-3-azabicyclo[3.2.1]oct-
8-yl}-N'-(3,4-difluorophenyl)-N-methylurea (m/z=441);

N-(3-{3-[(4-cyanophenyl)sulfonyl]propyl}-3-azabicyclo
[3.2.1]oct-8-yl)-N'-(3,5-dimethyl-4-isoxazolyl)-N-
methylurea (m/z=486);

3-{3-[(4-cyanophenyl)sulfonyl]propyl}-8-[methyl({[(4-
methylphenyl)sulfonyl]amino}carbonyl)amino]-3-
azabicyclo[3.2.1]octane (ES (M-1): m/z=543);

N-(3-{3-[(4-cyanophenyl)sulfonyl]propyl}-3-azabicyclo
[3.2.1]oct-8-yl)-N'-(4-methoxyphenyl)-N-methylurea
(m/z=497);

N-(3-{3-[(4-cyanophenyl)sulfonyl]propyl}-3-azabicyclo
[3.2.1]oct-8-yl)-N'-(cyclopropylmethyl)-N-methylurea
(m/z=445);

N-(3-{3-[(4-cyanophenyl)sulfonyl]propyl}-3-azabicyclo[3.2.1]oct-8-yl)-N'-(3,4-difluorophenyl)-N-methylurea (m/z=503);

N-(3-[3-(4-cyanophenoxy)-2-hydroxypropyl]-3-azabicyclo[3.2.1]oct-8-yl}-N-methyl-1-butanesulfonamide (m/z=436.2);

N-{3-[3-(4-cyanophenoxy)-2-hydroxypropyl]-3-azabicyclo[3.2.1]oct-8-yl}-3,4-dimethoxy-N-methylbenzenesulfonamide (m/z=516.2);

5-chloro-N-{3-[3-(4-cyanophenoxy)-2-hydroxypropyl]-3-azabicyclo[3.2.1]oct-8-yl}-N,1,3-trimethyl-1H-pyrazole4-sulfonamide (m/z=508.2);

N-(5-{[{3-[3-(4-cyanoanilino)propyl]-3-azabicyclo[3.2.1]oct-8-yl}(methyl)-amino]sulfonyl}-4-methyl-1,3-thiazol-2-yl)acetamnide (m/z=517.2);

N-{3-[3-(4-cyanoanilino)propyl]-3-azabicyclo[3.2.1]oct-8-yl}-N-methyl-4-nitrobenzenesulfonamide (m/z=484.2);

N-(4-{[{3-[3-(4-cyanoanilino)propyl]-3-azabicyclo[3.2.1]oct-8-yl}(methyl)amino]sulfonyl}phenyl)acetamide (m/z=496.2);

N-{3-[3-(4-cyanoanilino)propyl]-3-azabicyclo[3.2.1]oct-8-yl}-3,4-dimethoxy-N-methylbenzenesulfonamide (m/z=499.2);

5-chloro-N-{3-[3-(4-cyanoanilino)propyl]-3-azabicyclo[3.2.1]oct-8-yl}-N,1,3-trimethyl-1H-pyrazole-4-sulfonamide (m/z=491.2);

N-{3-[3-(4-cyanoanilino)propyl]-3-azabicyclo[3.2.1]oct-8-yl}-N-methyl-1-ethanesulfonamide (m/z=391.2);

N-(3-{3-[(4-cyanophenyl)sulfonyl]propyl}-3-azabicyclo[3.2.1]oct-8-yl)-N-methyl-4-nitrobenzenesulfonamide (m/z=533.1);

N-(3-{3-[(4-cyanophenyl)sulfonyl]propyl}-3-azabicyclo[3.2.1]oct-8-yl)-3,4-dimethoxy-N-methylbenzenesulfonamide (m/z=548.2);

N-(5-{[{3-[2-(4-cyanophenoxy)ethyl]-3-azabicyclo[3.2.1]oct-8-yl}-(methyl)amino]sulfonyl}4-methyl-1,3-thiazol-2-yl)acetamide (m/z=504.2);

N-{3-[2-(4-cyanophenoxy)ethyl]-3-azabicyclo[3.2.1]oct-8-yl}-N-methyl-4-nitrobenzenesulfonamide (m/z=471.2);

N-(4-([{3-[2-(4-cyanophenoxy)ethyl]-3-azabicyclo[3.2.1]oct-8-yl}-(methyl)amino]sulfonyl}phenyl)acetamnide (m/z=483.2);

N-{3-[2-(4-cyanophenoxy)ethyl]-3-azabicyclo[3.2.1]oct-8-yl)-N-methyl-2-propanesulfonamide;

N-{3-[2-(4-cyanophenoxy)ethyl]-3-azabicyclo[3.2.1]oct-8-yl}-3,4-dimethoxy-N-methylbenzenesulfonamide (m/z=486.2);

5-chloro-N-{3-[2-(4-cyanophenoxy)ethyl]-3-azabicyclo[3.2.1]oct-8-yl}-N,1,3-trimethyl-1H-pyrazole-4-sulfonamide (m/z=478.2);

N-{3-[2-(4-cyanophenoxy)ethyl]-3-azabicyclo[3.2.1]oct-8-yl}-N,1-dimethyl-1H-imidazole-4-sulfonamide (m/z=430.2);

2-butynyl 3-[3-(4-cyanophenoxy)-2-hydroxypropyl]-3-azabicyclo[3.2.1]-oct-8-yl(methyl)carbamate (m/z=412.5);

2-methoxyethyl 3-[3-(4-cyanophenoxy)-2-hydroxypropyl]-3-azabicyclo[3.2.1]oct-8-yl(methyl)carbamate (m/z=418.5);

3-(methylsulfonyl)propyl 3-[3-(4-cyanophenoxy)-2-hydroxypropyl]-3-azabicyclo[3.2.1]oct-8-yl(methyl)carbamate (m/z=480.5);

2-(4-acetyl-1-piperazinyl)ethyl 3-[3-(4-cyanophenoxy)-2-hydroxypropyl]-3-azabicyclo[3.2.1]oct-8-yl(methyl)carbamate;

2-hydroxy-1,1-dimethylethyl 3-[3-(4-cyanoanilino)propyl]-3-azabicyclo[3.2.1]oct-8-yl(methyl)carbamate;

1-cyano-1-methylethyl 3-[3-(4-cyanoanilino)propyl]-3-azabicyclo[3.2.1]oct-8-yl(methyl)carbamate (m/z=410.5);

2-butynyl 3-[3-(4-cyanoanilino)propyl]-3-azabicyclo[3.2.1]oct-8-yl-(methyl)carbamate (m/z=395.5);

2-methoxyethyl 3-[3-(4-cyanoanilino)propyl]-3-azabicyclo[3.2.1]oct-8-yl(methyl)carbamate (m/z=401.6);

3-(methylsulfonyl)propyl 3-[3-(4-cyanoanilino)propyl]-3-azabicyclo[3.2.1]oct-8-yl(methyl)carbamate (m/z=463.5);

2-(4-pyridinyl)ethyl 3-[3-(4-cyanoanilino)propyl]-3-azabicyclo[3.2.1]oct-8-yl(methyl)carbamate (m/z=448.6);

N-{3-[3-(4-cyanoanilino)propyl]-3-azabicyclo[3.2.1]oct-8-yl}-N'-[2-(2-methoxyethoxy)ethyl]-N-methylurea (m/z=444.6);

ethyl 3-{3-[(4-cyanophenyl)sulfonyl]propyl}-3-azabicyclo[3.2.1]oct-8-yl(methyl)carbamate (m/z=420.5);

2-hydroxy-1,1-dimethylethyl 3-{3-[(4-cyanophenyl)sulfonyl]propyl}-3-azabicyclo[3.2.1]oct-8-yl(methyl)carbamate;

2-(4-morpholinyl)ethyl 3-{3-[(4-cyanophenyl)sulfonyl]propyl}-3-azabicyclo[3.2.1]oct-8-yl(methyl)carbamate (m/z=505.5);

N-(3-{3-[(4-cyanophenyl)sulfonyl]propyl}-3-azabicyclo[3.2.1]oct-8-yl)-N'-[2-(2-methoxyethoxy)ethyl]-N-methylurea (m/z=493.5);

ethyl 3-[2-(4-cyanophenoxy)ethyl]-3-azabicyclo[3.2.1]oct-8-yl(methyl)carbamate (m/z=358.5);

2-hydroxy-1,1-dimethylethyl 3-[2-(4-cyanophenoxy)ethyl]-3-azabicyclo[3.2.1]oct-8-yl(methyl)carbamate;

1-cyano-1-methylethyl 3-[2-(4-cyanophenoxy)ethyl]-3-azabicyclo[3.2.1]-oct-8-yl(methyl)carbamate (m/z=397.5);

2-butynyl 3-[2-(4-cyanophenoxy)ethyl]-3-azabicyclo[3.2.1]oct-8-yl-(methyl)carbamate (m/z=382.5);

2-methoxyethyl 3-[2-(4-cyanophenoxy)ethyl]-3-azabicyclo[3.2.1]oct-8-yl-(methyl)carbamate (m/z=388.5);

3-(methylsulfonyl)propyl 3-[2-(4-cyanophenoxy)ethyl]-3-azabicyclo[3.2.1]oct-8-yl-(methyl)carbamate (m/z=450.5);

2-(4-pyridinyl)ethyl 3-[2-(4-cyanophenoxy)ethyl]-3-azabicyclo[3.2.1]oct-8-yl(methyl)carbamate (m/z=435.5);

N-{3-[3-(4-cyanophenoxy)-2-hydroxypropyl]-3-azabicyclo[3.2.1]oct-8-yl}-2-methoxy-N-methylacetamide (m/z=388.2);

N-{3-[3-(4-cyanophenoxy)-2-hydroxypropyl]-3-azabicyclo[3.2.1]oct-8-yl}-N,2-dimethylpropanamide (m/z=386.3);

N-{3-[3-(4-cyanophenoxy)-2-hydroxypropyl]-3-azabicyclo[3.2.1]oct-8-yl}-N,3-dimethylbutanamide (m/z=400.3);

N-{3-[3-(4-cyanophenoxy)-2-hydroxypropyl]-3-azabicyclo[3.2.1]oct-8-yl}-N-methyl-2,1,3-benzoxadiazole-5-carboxamide (m/z=461.5);

3-(tert-butyl)-N-{3-[3-(4-cyanophenoxy)-2-hydroxypropyl]-3-azabicyclo[3.2.1]oct-8-yl}-N,1-dimethyl-1H-pyrazole-5-carboxamide (m/z=480.3);

N-{3-[3-(4-cyanoanilino)propyl]-3-azabicyclo[3.2.1]oct-8-yl}-2-(2,5-dioxo-4-imidazolidinyl)-N-methylacetamide (m/z=439.3);

N-{3-[3-(4-cyanoanilino)propyl]-3-azabicyclo[3.2.1]oct-8-yl}-N-methyl-1H-pyrrole-2-carboxamide (m/z=392.3);

N-{3-[3-(4-cyanoanilino)propyl]-3-azabicyclo[3.2.1]oct-8-yl}-N,2-dimethylpropanamide (m/z=369.3);

N-{3-[3-(4-cyanoanilino)propyl]-3-azabicyclo[3.2.1]oct-8-yl}-N-methyl-2,1,3-benzoxadiazole-5-carboxamide (m/z=445.2);

3-(tert-butyl)-N-{3-[3-(4-cyanoanilino)propyl]-3-azabicyclo[3.2.1]oct-8-yl}-N,1-dimethyl-1H-pyrazole-5-carboxamide (m/z=463.3);

N-(3-{3-[(4-cyanophenyl)sulfonyl]propyl}-3-azabicyclo[3.2.1]oct-8-yl)-2-(2,5-dioxo-4-imidazolidinyl)-N-methylacetamide (m/z=488.2);

2-(acetylamino)-N-{2-[(3-{3-[(4-cyanophenyl)sulfonyl]propyl}-3-azabicyclo[3.2.1]oct-8-yl)(methyl)amino]-2-oxoethyl}acetamide (m/z=25 504.2);

N-(3-{3-[(4-cyanophenyl)sulfonyl]propyl}-3-azabicyclo[3.2.1]oct-8-yl)-N-methyl-2,1,3-benzoxadiazole-5-carboxamide (m/z=494.1);

N-{3-[2-(4-cyanophenoxy)ethyl]-3-azabicyclo[3.2.1]oct-8-yl}-2-(2,5-dioxo-4-imidazolidinyl)-N-methylacetamide (m/z=426.2);

N-{3-[2-(4-cyanophenoxy)ethyl]-3-azabicyclo[3.2.1]oct-8-yl}-N,2-dimethylpropanamide (m/z=356.2);

N-{3-[2-(4-cyanophenoxy)ethyl]-3-azabicyclo[3.2.1]oct-8-yl}-N,3-dimethylbutanamide (m/z=370.3);

N-{3-[2-(4-cyanophenoxy)ethyl]-3-azabicyclo[3.2.1]oct-8-yl}-N-methyl-2,1,3-benzoxadiazole-5-carboxamide (m/z=432.2);

3-(tert-butyl)-N-{3-[2-(4-cyanophenoxy)ethyl]-3-azabicyclo[3.2.1]oct-8-yl}-N,1-dimethyl-1H-pyrazole-5-carboxamide (m/z=450.3);

4-(3-{8-[(cyclopropylmethyl)(methyl)amino]-3-azabicyclo[3.2.1]oct-3-yl}-2-hydroxypropoxy)benzonitrile (m/z=370.5);

4-(3-{8-[[2-(2,3-dihydro-1,4-benzodioxin-6-yl)-2-oxoethyl](methyl)amino]-3-azabicyclo[3.2.1]oct-3-yl}-2-hydroxypropoxy)benzonitrile (m/z=492.5);

4-(3-{8-[[3-(4-acetyl-1-piperazinyl)propyl](methyl)amino]-3-azabicyclo[3.2.1]oct-3-yl}-2-hydroxypropoxy)benzonitrile (m/z=484.5);

2-[{3-[3-(4-cyanophenoxy)-2-hydroxypropyl]-3-azabicyclo[3.2.1]oct-8-yl}(methyl)amino]-N-isopropylacetamide (m/z 415.5);

4-(3-{8-[[3-(ethylsulfonyl)propyl](methyl)amino]-3-azabicyclo[3.2.1]oct-3-yl}-2-hydroxypropoxy)benzonitrile (m/z=450.5);

4-(3-{8-[(4-fluorobenzyl)(methyl)amino]-3-azabicyclo[3.2.1]oct-3-yl}-2-bydroxypropoxy)benzonitrile (m/z=424.5);

4-(2-hydroxy-3-{8-[[2-(4-methoxyphenyl)-2-oxoethyl](methyl)amino]-3-azabicyclo[3.2.1]oct-3-yl}propoxy)benzonitrile (m/z=464.5);

4-[(3-{8-[(cyclopropylmethyl)(methyl)amino]-3-azabicyclo[3.2.1]oct-3-yl}propyl)amino]benzonitrile (m/z=353.5);

4-[(3-{8-[[2-(2,3-dihydro-1,4-benzodioxin-6-yl)-2-oxoethyl](methyl)amino]-3-azabicyclo[3.2.1]oct-3-yl}propyl)amino]benzonitrile (m/z=475.5);

4-[(3-{8-[[3-(4-acetyl-1-piperazinyl)propyl](methyl)amino]-3-azabicyclo[3.2.1]oct-3-yl}propyl)amino]benzonitrile (m/z=467.6);

2-[{3-[3-(4-cyanoanilino)propyl]-3-azabicyclo[3.2.1]oct-8-yl}(methyl)amino]-N-isopropylacetamide (m/z=398.5);

4-[(3-{8-[[3-(ethylsulfonyl)propyl](methyl)amino]-3-azabicyclo[3.2.1]oct-3-yl}propyl)amino]benzonitrile (m/z=433.5);

4-[(3-{8-[(4-fluorobenzyl)(methyl)amino]-3-azabicyclo[3.2.1]oct-3-yl}-propyl)amino]benzonitrile (m/z=407.5);

4-[(3-{8-[[2-(4-methoxyphenyl)-2-oxoethyl](methyl)amino]-3-azabicyclo[3.2.1]oct-3-yl}propyl)amino]benzonitrile (m/z=447.5);

4-[(3-{8-[[(3,3-dimethyl-2-oxobutyl)(methyl)amino]-3-azabicyclo[3.2.1]oct-3-yl}propyl)sulfonyl]benzonitrile (m/z=446.5);

4-[(3-{8-[(cyclopropylmethyl)(methyl)amino]-3-azabicyclo[3.2.1]oct-3-yl}-propyl)sulfonyl]benzonitrile (m/z=402.5);

4-[(3-{8-[[2-(2,3-dihydro-1,4-benzodioxin-6-yl)-2-oxoethyl](methyl)amino]-3-azabicyclo[3.2.1]oct-3-yl}propyl)sulfonyl]benzonitrile (m/z=524.4);

2-[(3-{3-[(4-cyanophenyl)sulfonyl]propyl}-3-azabicyclo[3.2.1]oct-8-yl)-(methyl)amino]-N-isopropylacetamide (m/z=447.5);

4-[(3-{8-[[3-(ethylsulfonyl)propyl](methyl)amino]-3-azabicyclo[3.2.1]oct-3-yl}propyl)sulfonyl]benzonitrile (m/z=482.4);

4-[(3-{8-[[2-(2-methoxyethoxy)ethyl](methyl)amino]-3-azabicyclo[3.2.1]-oct-3-yl}propyl)sulfonyl]benzonitrile (m/z=450.5);

4-[(3-{8-[(4-fluorobenzyl)(methyl)amino]-3-azabicyclo[3.2.1]oct-3-yl}-propyl)sulfonyl]benzonitrile (m/z=456.5);

4-[(3-{8-[[2-(4-methoxyphenyl)-2-oxoethyl](methyl)amino]-3-azabicyclo[3.2.1]oct-3-yl}propyl)sulfonyl]benzonitrile (m/z=496.4);

4-(2-{8-[(3,3-dimethyl-2-oxobutyl)(methyl)amino]-3-azabicyclo[3.2.1]oct-3-yl}ethoxy)benzonitrile (m/z=384.5);

4-(2-{8-[(cyclopropylmethyl)(methyl)amino]-3-azabicyclo[3.2.1]oct-3-yl}-ethoxy)benzonitrile (m/z=340.5);

4-(2-{8-[[2-(2,3-dihydro-1,4-benzodioxin-6-yl)-2-oxoethyl](methyl)-amino]-3-azabicyclo[3.2.1]oct-3-yl}ethoxy)benzonitrile (m/z=462.5);

2-[{3-[2-(4-cyanophenoxy)ethyl]-3-azabicyclo[3.2.1]oct-8-yl}(methyl)-amino]-N-isopropylacetamide (m/z=385.5);

4-(2-{8-[[2-(2-methoxyethoxy)ethyl](methyl)amino]-3-azabicyclo[3.2.1]-oct-3-yl}ethoxy)benzonitrile (m/z=388.5);

4-(2-{8-[(4-fluorobenzyl)(methyl)amino]-3-azabicyclo[3.2.1]oct-3-yl}-ethoxy)benzonitrile (m/z=394.5);

methyl (1S)-2-(4-cyanophenoxy)-1-({8-[methyl({[(4-methylphenyl)sulfonyl]amino}carbonyl)amino]-3-azabicyclo[3.2.1]oct 3-yl}methyl)ethylcarbamate (m/z=570.4);

methyl (1S)-2-(4-cyanophenoxy)-1-({8-[methyl({4-[(trifluoromethyl)sulfanyl]anilino}carbonyl)amino]-3-azabicyclo[3.2.1]oct-3-yl}methyl)ethylcarbamate (m/z=592.3);

methyl (1S)-2-(4-cyanophenoxy)-1-[(8-{methyl[(tetrahydro-2H-pyran-2-ylamino)carbonyl]amino}-3-azabicyclo[3.2.1]oct-3-yl)methyl]-ethylcarbamate (m/z=500.5);

methyl (1S)-2-(4-cyanophenoxy)-1-({8-[{[(cyclopropylmethyl)amino]-carbonyl}(methyl)amino]-3-azabicyclo[3.2.1]oct-3-yl}methyl)ethylcarbamate (m/z=470.5);

methyl (1S)-2-(4-cyanophenoxy)-1-({8-[[(isopropylamino)carbonyl]-(methyl)amino]-3-azabicyclo[3.2.1]oct-3-yl}methyl)ethylcarbamate (m/z=458.5);

methyl (1S)-2-(4-cyanophenoxy)-1-({8-[[(3,4-difluoroanilino)carbonyl]-(methyl)amino]-3-azabicyclo[3.2.1]oct-3-yl}methyl)ethylcarbamate (m/z=528.5);

methyl (1S)-2-{8-[[(butylamino)carbonyl](methyl)amino]-3-azabicyclo[3.2.1]oct-3-yl}-1-[(4-cyanophenoxy)methyl]ethylcarbamate (m/z=472.5);

N-{3-[(2S)-2-amino-3-(4-cyanophenoxy)propyl]-3-azabicyclo[3.2.1]oct-8-s yl}-N'-(4-methoxyphenyl)-N-methylurea (m/z=464.5);

N-{3-[(2S)-2-amino-3-(4-cyanophenoxy)propyl]-3-azabicyclo[3.2.1]oct-8-yl}-N'-(cyclopropylmethyl)-N-methylurea (m/z=412.5);

N-{3-[(2S)-2-amino-3-(4-cyanophenoxy)propyl]-3-azabicyclo[3.2.1]oct-8-yl}-N'-(3,4-difluorophenyl)-N-methylurea (m/z=470.5);

N-{3-[(2S)-2-amino-3-(4-cyanophenoxy)propyl]-3-azabicyclo[3.2.1]oct-8-yl}-N'-butyl-N-methylurea (m/z=414.6);

N-{3-[4-(4-cyanophenyl)-4-(4-hydroxyphenoxy)butyl]-3-azabicyclo[3.2.1]-oct-8-yl}-N'-(3,5-dimethyl-4-isoxazolyl)-N-methylurea (m/z=544.5);

N-3-[4-(4-cyanophenyl)-4-(4-hydroxyphenoxy)butyl]-3-azabicyclo[3.2.1]-oct-8-yl}-N'-(4-methoxyphenyl)-N-methylurea (m/z=555.5);

N-3-[4-(4-cyanophenyl)-4-(4-hydroxyphenoxy)butyl]-3-azabicyclo[3.2.1]-oct-8-yl}-N-methyl-N'-{4-[(trifluoromethyl)sulfanyl]phenyl}urea (m/z=625.3);

N'-butyl-N-{3-[4-(4-cyanophenyl)-4-(4-hydroxyphenoxy)butyl]-3-azabicyclo[3.2.1]oct-8-yl}-N-methylurea (m/z=505.6); and tert-butyl 3-[(2S)-2-amino-3-(4-cyanophenoxy)propyl]-3-azabicyclo[3.2.1]-oct-8-yl(methyl)carbamate (m/z=415.5).

Example 8

Compounds of the above Examples were tested in Test A above and were found to exhibit pIC50 values of greater than 5.5.

| Abbreviations | | |
|---|---|---|
| Ac | = | acetyl |
| API | = | atmospheric pressure ionisation (in relation to MS) |
| aq. | = | aqueous |
| br | = | broad (in relation to NMR) |

| -continued | | |
|---|---|---|
| Abbreviations | | |
| Bt | = | benzotriazole |
| t-BuOH | = | tert-butanol |
| CI | = | chemical ionisation (in relation to MS) |
| mCPBA | = | meta-chloroperoxybenzoic acid |
| d | = | doublet (in relation to NMR) |
| DBU | = | diazabicyclo[5.4.0]undec-7-ene |
| DCM | = | dichloromethane |
| dd | = | doublet of doublets (in relation to NMR) |
| DMAP | = | 4-dimethylaminopyridine |
| DMF | = | N,N-dimethylformamide |
| DMSO | = | dimethylsulfoxide |
| EDC | = | 1-[3-(dimethylamino)propyl]-3-ethylcarbodiimide |
| Et | = | ethyl |
| EtOAc | = | ethyl acetate |
| eq. | = | equivalents |
| ES | = | electrospray (in relation to MS) |
| FAB | = | fast atom bombardment (in relation to MS) |
| h | = | hour(s) |
| HCl | = | hydrochloric acid |
| HEPES | = | 4-(2-hydroxyethyl)-1-piperazineethanesulfonic acid |
| HPLC | = | high performance liquid chromatography |
| IPA | = | iso-propyl alcohol (propan-2-ol) |
| m | = | multiplet (in relation to NMR) |
| Me | = | methyl |
| MeCN | = | acetonitrile |
| MeOH | = | methanol |
| min. | = | minute(s) |
| m.p. | = | melting point |
| MS | = | mass spectroscopy |
| NADPH | = | nicotinamide adenine dinucleotide phosphate, reduced form |
| OAc | = | acetate |
| Pd/C | = | palladium on carbon |
| q | = | quartet (in relation to NMR) |
| rt | = | room temperature |
| s | = | singlet (in relation to NMR) |
| t | = | triplet (in relation to NMR) |
| TEA | = | triethylamine |
| THF | = | tetrahydrofuran |
| tlc | = | thin layer chromatography |

Prefixes n-, s-, i-, t- and tert- have their usual meanings: normal, secondary, iso, and tertiary.

What is claimed is:

1. A compound of formula I,

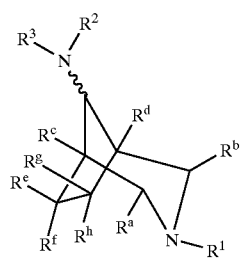

I wherein the wavy bond represents optional endo- or exo-stereochemistry;

one of $R^1$ and $R^2$ represents $R^{1a}$ and the other represents a fragment of the formula Ia,

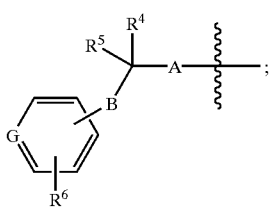

Ia $R^{1a}$ represents $C_{1-12}$ alkyl (optionally substituted and/or terminated by one or more groups selected from halo, cyano, nitro, aryl, $Het^1$, —C(O)$R^{7a}$, —O$R^{7b}$, —N($R^8$)$R^{7c}$, —C(O)X$R^9$, —C(O)N($R^{10}$)$R^{7d}$ and —S(O)$_2R^{11}$), $Het^2$, —C(O)$R^{7a}$, —C(O)X$R^9$, —C(O)N($R^{10}$)$R^{7d}$ or —S(O)$_2R^{11}$;

$R^{7a}$ to $R^{7d}$ independently represent, at each occurrence when used herein, H, $C_{1-6}$ alkyl (optionally substituted and/or terminated by one or more substituents selected from —OH, $C_{1-6}$ alkoxy, halo, cyano, nitro, aryl, $Het^3$ and —NHC(O)$R^{12}$), aryl or $Het^4$, or $R^{7d}$, together with $R^{10}$, represents $C_{3-6}$ alkylene (which alkylene group is optionally interrupted by an O atom and/or is optionally substituted by one or more $C_{1-3}$ alkyl groups);

$R^{12}$ represents H, $C_{1-4}$ alkyl (optionally substituted and/or terminated by one or more substituents selected from halo, cyano, aryl and —NHC(O)$R^{13}$) or aryl;

$R^{13}$ represents H, $C_{1-4}$ alkyl or aryl;

$R^8$ represents H, $C_{1-6}$ alkyl (optionally substituted and/or terminated by one or more substituents selected from —OH, halo, cyano, nitro and aryl), aryl, —C(O)$R^{14a}$ or —C(O)O$R^{14b}$;

$R^{14a}$ and $R^{14b}$ represent $C_{1-6}$ alkyl (optionally substituted and/or terminated by one or more substituents selected from —OH, halo, cyano, nitro and aryl) or aryl, or $R^{14a}$ represents H;

X represents O or S;

$R^9$ represents, at each occurrence when used herein, $C_{1-12}$ alkyl (optionally substituted and/or terminated by one or more substituents selected from —OH, halo, cyano, nitro, aryl, $C_{1-6}$ alkoxy, —SO$_2R^{15}$ and $Het^5$);

$R^{15}$ represents $C_{1-6}$ alkyl or aryl;

$R^{10}$ represents, at each occurrence when used herein, H, $C_{1-12}$ alkyl, $C_{1-6}$ alkoxy (which latter two groups are optionally substituted and/or terminated by one or more substituents selected from —OH, halo, cyano, nitro, $C_{1-4}$ alkyl and $C_{1-4}$ alkoxy), —D-aryl, —D-aryloxy, —D-$Het^6$, —D—N(H)C(O)$R^{16a}$, —D—S(O)$_2R^{17a}$, —D—C(O)$R^{16b}$, —D—C(O)O$R^{17b}$, —D—C(O)N($R^{16c}$)$R^{16d}$, or $R^{10}$, together with $R^{7d}$, represents $C_{3-6}$ alkylene (which alkylene group is optionally interrupted by an O atom and/or is optionally substituted by one or more $C_{1-3}$ alkyl groups);

$R^{16a}$ to $R^{16d}$ independently represent H, $C_{1-6}$ alkyl (optionally substituted and/or terminated by one or more substituents selected from —OH, halo, cyano, nitro and aryl), aryl, or $R^{16c}$ and $R^{16d}$ together represent $C_{3-6}$ alkylene;

$R^{17a}$ and $R^{17b}$ independently represent $C_{1-6}$ alkyl (optionally substituted and/or terminated by one or more substituents selected from —OH, halo, cyano, nitro and aryl) or aryl;

D represents a direct bond or $C_{1-6}$ alkylene;

$R^{11}$ represents, at each occurrence when used herein, $C_{1-6}$ alkyl (optionally substituted and/or terminated by one or more substituents selected from is —OH, halo, cyano, nitro and aryl), aryl or $Het^7$;

$R^4$ represents H, halo, $C_{1-6}$ alkyl, —O$R^{18}$, —E—N($R^{19}$)$R^{20}$ or, together with $R^5$, represents =O;

$R^5$ represents H, $C_{1-6}$ alkyl or, together with $R^4$, represents =O;

$R^{18}$ represents H, $C_{1-6}$ alkyl, —E-aryl, —E—$Het^8$, —C(O)$R^{21a}$, —C(O)O$R^{21b}$ or —C(O)N($R^{22a}$)$R^{22b}$;

$R^{19}$ represents H, $C_{1-6}$ alkyl, —E-aryl, —E—$Het^8$, —C(O)$R^{21a}$, —C(O)O$R^{21b}$, —S(O)$_2R^{21c}$, —[C(O)]$_p$N($R^{22a}$)$R^{22b}$ or —C(NH)NH$_2$;

$R^{20}$ represents H, $C_{1-6}$ alkyl, —E-aryl or —C(O)$R^{21d}$;

$R^{21a}$ to $R^{21d}$ independently represent, at each occurrence when used herein, $C_{1-6}$ alkyl (optionally substituted and/or terminated by one or more substituents selected from halo, aryl and $Het^9$), aryl, $Het^{10}$, or $R^{21a}$ and $R^{21d}$ independently represent H;

$R^{22a}$ and $R^{22b}$ independently represent, at each occurrence when used herein, H or $C_{1-6}$ alkyl (optionally substituted and/or terminated by one or more substituents selected from halo, aryl and $Het^{11}$), aryl, $Het^{12}$, or together represent $C_{3-6}$ alkylene, optionally interrupted by an O atom;

E represents, at each occurrence when used herein, a direct bond or $C_{1-4}$ alkylene;

p represents 1 or 2;

$Het^1$ to $Het^{12}$ independently represent, at each occurrence when used herein, five- to twelve-membered heterocyclic groups containing one or more heteroatoms selected from oxygen, nitrogen and/or sulfur, which groups are optionally substituted by one or more substituents selected from —OH, oxo, halo, cyano, nitro, $C_{1-6}$ alkyl, $C_{1-6}$ alkoxy, aryl, aryloxy, —N($R^{23a}$)$R^{23b}$, —C(O)$R^{23c}$, —C(O)O$R^{23d}$, —C(O)N($R^{23e}$)$R^{23f}$, —N($R^{23g}$)C(O)$R^{23h}$ and —N($R^{23i}$)S(O)$_2R^{23j}$;

$R^{23a}$ to $R^{23j}$ independently represent $C_{1-6}$ alkyl, aryl or $R^{23a}$ to $R^{23i}$ independently represent H;

A represents a direct bond, —J—, —J—N($R^{24}$)— or —J—O— (in which latter two groups, N($R^{24}$)— or O— is attached to the carbon atom bearing $R^4$ and $R^5$);

B represents —Z—, —Z—N($R^{25}$)—, —N($R^{25}$)—Z—, —Z—S(O)$_n$—, —Z—O— (in which latter two groups, Z is attached to the carbon atom bearing $R^4$ and $R^5$), —N($R^{25}$)C(O)O—Z—, (in which latter group, —N($R^{25}$) is attached to the carbon atom bearing $R^9$ and $R^{10}$) or —C(O)N($R^{25}$)— (in which latter group, —C(O) is attached to the carbon atom bearing $R^4$ and $R^5$);

J represents $C_{1-6}$ alkylene optionally substituted by one or more substituents selected from —OH, halo and amino;

Z represents a direct bond or $C_{1-4}$ alkylene;

$R^{24}$ and $R^{25}$ independently represent H or $C_{1-6}$ alkyl;

G represents CH or N;

$R^6$ represents one or more optional substituents selected from —OH, cyano, halo, nitro, $C_{1-6}$ alkyl (optionally terminated by —N(H)C(O)O$R^{26a}$), $C_{1-6}$ alkoxy, —N($R^{27a}$)$R^{27b}$, —C(O)$R^{27c}$, —C(O)O$R^{27d}$, —C(O)N($R^{27e}$)$R^{27f}$, —N($R^{27g}$)C(O)$R^{27h}$, —N($R^{27i}$)C(O)N($R^{27j}$)$R^{27k}$, —N($R^{27m}$)S(O)$_2R^{26b}$, —S(O)$_nR^{26c}$, and/or —OS(O)$_2R^{26d}$;

$R^{26a}$ to $R^{26d}$ independently represent $C_{1-6}$ alkyl;

$R^{27a}$ to $R^{27m}$ independently represent H or $C_{1-6}$ alkyl;

n represents, at each occurrence, 0, 1 or 2; and

R$^a$ to R$^h$ and R$^3$ independently represent H or C$_{1-4}$ alkyl;
wherein each aryl and aryloxy group, unless otherwise specified, is optionally substituted;
or a pharmaceutically acceptable derivative thereof;
provided that
(a) when A represents —J—N(R$^{24}$)— or —J—O—, then:
 (i) J does not represent C$_1$ alkylene; and
 (ii) B does not represent —N(R$^{25}$)—, —N(R$^{25}$)—Z— (in which latter group N(R$^{25}$) is attached to the carbon atom bearing R$^4$ and R$^5$), —S(O)$_n$—, —O— or —N(R$^{25}$)C(O)O—Z— when R$^4$ and R$^5$ do not together represent =O;
(b) when R$^4$ represents —OR$^{18}$ or —N(R$^{19}$)(R$^{20}$), then:
 (i) A does not represent —J—N(R$^{24}$)— or —J—O—; and
 (ii) B does not represent —N(R$^{25}$)—, —N(R$^{25}$)—Z— (in which latter group N(R$^{25}$) is attached to the carbon atom bearing R$^4$ and R$^5$), —S(O)$_n$—, —O— or —N(R$^{25}$)C(O)O—Z—;
(c) when A represents a direct bond, then R$^4$ and R$^5$ do not together represent =O; and
(d) the compound is not: (±) (8β)-4-amino-5-chloro-2-methoxy-N-(3-benzyl-3-azabicyclo[3.2.1]oct-8-yl)benzamide; (S)-N-(3-benzyl-3-azabicyclo[3.2.1]oct-8-yl)-4-amino-5-chloro-2-(1-methyl-2-butynyl)oxybenzamide; or (S)-N-(3-benzyl-3-azabicyclo[3.2.1]oct-8-yl)-4-amino-5-chloro-2-(1-methyl-2-butynyl)oxybenzamide hydrochloride.

2. A compound as claimed in claim 1, wherein the optional substituents on aryl and aryloxy groups are one or more groups selected from —OH, halo, Het$^1$, cyano, nitro, C$_{1-6}$ alkyl, C$_{1-6}$ alkoxy, —N(R$^{27a}$)R$^{27b}$, —C(O)R$^{27c}$, —C(O)OR$^{27d}$, —C(O)N(R$^{27e}$)R$^{27f}$, —N(R$^{27g}$)C(O)R$^{27h}$, —N(R$^{27m}$)S(O)$_2$R$^{26b}$, —S(O)$_n$R$^{26c}$, and/or —OS(O)$_2$R$^{26d}$, wherein Het$^1$, R$^{26b}$ to R$^{26d}$, R$^{27a}$ to R$^{27m}$ and n are as defined in claim 1, provided that when substituted by one or more Het$^1$ group(s), any aryl group(s) that said Het$^1$ group(s) may be substituted with may not itself (themselves) be substituted by any Het$^1$ group(s).

3. A compound as claimed in claim 1, wherein R$^a$ to R$^h$ all represent H.

4. A compound as claimed in claim 1, wherein R$^{1a}$ represents C$_{1-8}$ alkyl (optionally substituted and/or terminated by one or more groups selected from halo, optionally substituted aryl, Het$^1$, —C(O)R$^{7a}$, —OR$^{7b}$, —N(R$^8$)R$^{7c}$, —C(O)XR$^9$, —C(O)N(R$^{10}$)R$^{7d}$ and —S(O)$_2$R$^{11}$), Het$^2$, —C(O)R$^{7a}$, —C(O)XR$^9$, —C(O)N(R$^{10}$)R$^{7d}$ or —S(O)$_2$R$^{11}$.

5. A compound as claimed in claim 4, wherein R$^{7a}$ to R$^{7d}$ independently represent, at each occurrence, H, C$_{1-5}$ alkyl (optionally substituted and/or terminated by one or more substituents selected from —OH, C$_{1-4}$ alkoxy, halo, cyano, optionally substituted aryl, Het$^3$ and —NHC(O)R$^{12}$), optionally substituted aryl or Het$^4$, or R$^{7d}$, together with R$^{10}$, represents C$_{3-6}$ alkylene.

6. A compound as claimed in claim 5, wherein R$^{12}$ represents C$_{1-3}$ alkyl (optionally substituted and/or terminated by one or more substituents selected from halo, aryl and —NHC(O)R$^{13}$) or optionally substituted aryl.

7. A compound as claimed in claim 6, wherein R$^{13}$ represents C$_{1-3}$ alkyl or aryl.

8. A compound as claimed in claim 1, wherein R$^8$ represents H, C$_{1-4}$ alkyl (optionally substituted and/or terminated by optionally substituted aryl), optionally substituted aryl, —C(O)R$^{14a}$ or —C(O)OR$^{14b}$.

9. A compound as claimed in claim 8, wherein R$^{14a}$ and R$^{14b}$ represent C$_{1-4}$ alkyl (optionally substituted and/or terminated by aryl) or aryl.

10. A compound as claimed in 1, wherein R$^9$ represents, at each occurrence, C$_{1-8}$ alkyl (optionally substituted and/or terminated by one or more substituents selected from —OH, halo, cyano, optionally substituted aryl, C$_{1-4}$ alkoxy, —SO$_2$R$^{15}$ and Het$^5$).

11. A compound as claimed in claim 10, wherein R$^{15}$ represents C$_{1-4}$ alkyl or aryl.

12. A compound as claimed in 1, wherein R$^{10}$ represents, at each occurrence, H, C$_{1-8}$ alkyl, C$_{1-4}$ alkoxy (which latter two groups are optionally substituted and/or terminated by one or more substituents selected from —OH, halo and C$_{1-4}$ alkoxy), —D-(optionally substituted aryl), —D-aryloxy, —D—Het$^6$, —D—S(O)$_2$R$^{17a}$, or R$^{10}$, together with R$^{7d}$, represents C$_{3-6}$ alkylene.

13. A compound as claimed in claim 12, wherein R$^{17a}$ represents C$_{1-4}$ alkyl or optionally substituted aryl.

14. A compound as claimed in claim 1, wherein D represents a direct bond or C$_{1-3}$ alkylene.

15. A compound as claimed in claim 1, wherein R$^{11}$ represents, at each occurrence, C$_{1-5}$ alkyl (optionally substituted and/or terminated by one or more halo atoms), optionally substituted aryl or Het$^7$.

16. A compound as claimed in claim 1, wherein R$^4$ represents H, halo, C$_{1-2}$ alkyl, —OR$^{18}$ or —E—N(R$^{19}$)R$^{20}$.

17. A compound as claimed in claim 1, wherein R$^5$ represents H, or C$_{1-2}$ alkyl.

18. A compound as claimed in claim 1, wherein R$^{18}$ represents H, C$_{1-4}$ alkyl, —E-(optionally substituted aryl) or —E—Het$^8$.

19. A compound as claimed in claim 1, wherein R$^{19}$ represents H, C$_{1-4}$ alkyl, —E-aryl, —E—Het$^8$, —C(O)R$^{21a}$ or —C(O)OR$^{21}$b.

20. A compound as claimed in claim 1, wherein R$^{20}$ represents H, C$_{1-4}$ alkyl or —E-aryl.

21. A compound as claimed in claim 1, wherein R$^{21a}$ and R$^{21b}$ independently represent C$_{1-4}$ alkyl (optionally substituted and/or terminated by one or more substituents selected from halo and aryl) or aryl.

22. A compound as claimed in claim 1, wherein E represents, at each occurrence, a direct bond or C$_{1-2}$ alkylene.

23. A compound as claimed in claim 1, wherein Het$^1$ to Het$^8$ (as appropriate) independently represent, at each occurrence, fully saturated, wholly aromatic, partly aromatic and/or bicyclic five- to twelve-membered heterocyclic groups containing between one and four heteroatoms selected from oxygen, nitrogen and/or sulfur, which groups are optionally substituted by one or more substituents selected from oxo, halo, cyano, C$_{1-5}$ alkyl, C$_{1-4}$ alkoxy, —N(R$^{23a}$)R$^{23b}$, —C(O)R$^{23c}$, —C(O)OR$^{23d}$, —C(O)N(R$^{23e}$)R$^{23f}$, and —N(R$^{23g}$)C(O)R$^{23h}$.

24. A compound as claimed in claim 23, wherein R$^{23a}$ to R$^{23h}$ independently represent H or C$_{1-3}$ alkyl.

25. A compound as claimed in claim 1, wherein A represents a direct bond or —J—.

26. A compound as claimed in claim 1, wherein B represents —Z—, —Z—N(R$^{25}$)—, —Z—S(O)$_n$— or —Z—O— (in which latter three groups, Z is attached to the carbon atom bearing R$^4$ and R$^5$).

27. A compound as claimed in claim 1, wherein J represents C$_{1-5}$ alkylene optionally substituted by one or more substituents selected from —OH, halo and amino.

28. A compound as claimed in claim 1, wherein Z represents a direct bond or C$_{1-3}$ alkylene.

29. A compound as claimed in claim 1, wherein n represents 0 or 2.

30. A compound as claimed in claim 1, wherein R$^{25}$ represents H or C$_{1-4}$ alkyl.

31. A compound as claimed in claim 1, wherein G represents CH.

32. A compound as claimed in claim 1, wherein $R^6$ represents one or more optional substituents selected from —OH, cyano, halo, nitro, $C_{1-3}$ alkyl (optionally terminated by —N(H)C(O)O$R^{26a}$) and $C_{1-4}$ alkoxy.

33. A compound as claimed in claim 32, wherein $R^6$ represents one or two cyano groups.

34. A compound as claimed in claim 1, wherein $R^{26a}$ represents $C_{1-4}$ alkyl.

35. A compound as claimed in claim 1, wherein $R^3$ represents H or $C_{1-2}$ alkyl.

36. A pharmaceutical formulation including a compound as defined in claim 1 in admixture with a pharmaceutically-acceptable adjuvant, diluent or carrier.

37. A method of prophylaxis or treatment of an arrhythmia which method comprises administration of a therapeutically effective amount of a compound as defined in claim 10 a person suffering from, or susceptible to, such a condition.

38. A process for the preparation of a compound of formula I as defined in claim 1 which comprises:

(a) reaction of a compound of formula IIA or IIB,

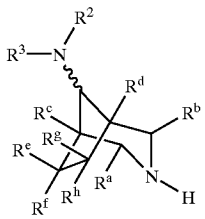

IIA

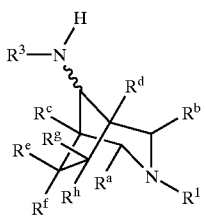

IIB wherein $R^1$, $R^2$, $R^3$ and $R^a$ to $R^h$ are as defined in claim 1, with a compound of formula III, $R^{28}$—$L^1$     III wherein $R^{28}$ represents (as appropriate) either $R^1$ or $R^2$, $L^1$ represents a leaving group and $R^1$ and $R^2$ are as defined in claim 1;

(b) for compounds of formula I in which $R^1$ or $R^2$ (as appropriate) represents —C(O)X$R^9$ or —C(O)N($R^{10}$)$R^{7d}$, reaction of a compound of formula IVA or IVB,

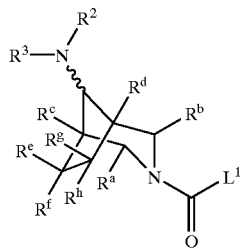

IVA

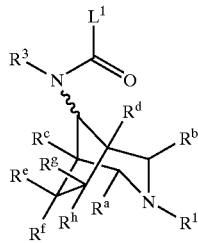

IVB wherein $R^3$ and $R^a$ to $R^h$ are as defined in claim 1, $L^1$ is as defined above, and $R^1$ and $R^2$ represent a fragment of formula Ia, as defined in claim 1, with a compound of formula V, $R^{30}$—H     V wherein $R^{30}$ represents —X$R^9$ or —N($R^{10}$)$R^{7d}$ and $R^{7d}$, $R^9$, $R^{10}$ and X are as defined in claim 1;

(c) for compounds of formula I in which $R^1$ or $R^2$ (as appropriate) represents —C(O)N(H)$R^{10}$, reaction of a compound of formula IIA or IIB (as appropriate), as defined above (except that $R^1$ or $R^2$ (as appropriate) does not represent $R^{1a}$), with a compound of formula VI, $R^{10}$—N=C=O     VI wherein $R^{10}$ is as defined in claim 1;

(d) for compounds of formula I in which $R^1$ or $R^2$ (as appropriate) represents a fragment of formula Ia in which A represents $CH_2$ and $R^4$ represents —OH or —N(H)$R^{19}$, reaction of a compound of formula IIA or IIB, as defined above (except that $R^1$ or $R^2$ (as appropriate) does not represent a fragment of formula Ia), with a compound of formula VII,

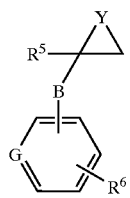

VII wherein Y represents O or N($R^{19}$) and $R^5$, $R^6$, $R^{19}$, B and G are as defined in claim 1;

(e) for compounds of formula I in which, in the fragment of formula Ia, B represents —Z—O—, reaction of a compound of formula VIIIA or VIIIB,

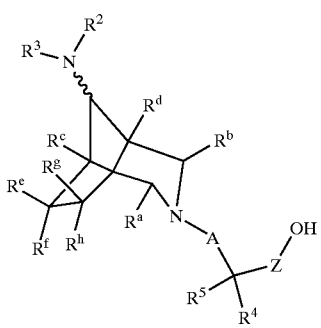

VIIIA

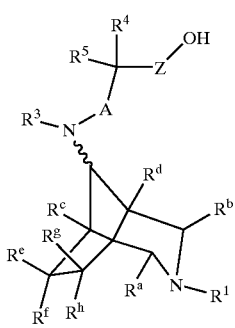

VIIIB wherein $R^3$, $R^4$, $R^5$, $R^a$ to $R^h$, A and Z are as defined in claim 1, and $R^1$ and $R^2$ (as appropriate) are as defined in claim 1 (except that, in each case, they do not represent a fragment of formula Ia), with a compound of formula IX,

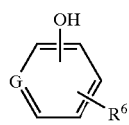

IX wherein $R^6$ and G are as defined in claim 1;

(f) for compounds of formula I in which G represents N and B represents —Z—O—, reaction of a compound of formula VIIIA or VIIIB, as defined above, with a compound of formula X,

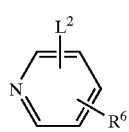

X wherein $L^2$ represents a leaving group and $R^6$ is as defined in claim 1;

(g) for compounds of formula I in which $R^4$ represents —$OR^{18}$, in which $R^{18}$ represents $C_{1-6}$ alkyl, —E-aryl or —E—$Het^8$, reaction of a corresponding compound of formula I in which $R^4$ represents OH with a compound of formula XI, $R^{18a}OH$          XI wherein $R^{18a}$ represents $C_{1-6}$ alkyl, —E-aryl or —E—$Het^8$, and E and $Het^8$ are as defined in claim 1;

(h) for compounds of formula I in which $R^4$ represents —$OR^{18}$, in which $R^{18}$ represents $C_{1-6}$ alkyl, —E-aryl or —E—$Het^8$, reaction of a compound of formula XIIA or XIIB,

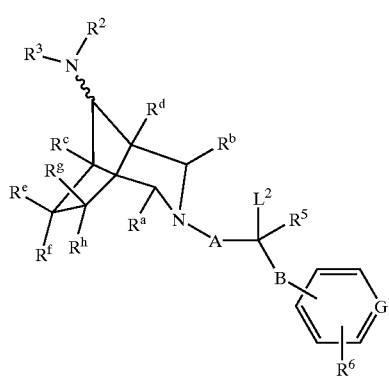

XIIA

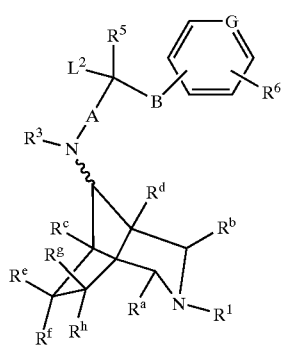

XIIB wherein $R^1$ or $R^2$ (as appropriate) represents $R^{1a}$, and $R^{1a}$, $R^3$, $R^5$, $R^6$, $R^a$ to $R^h$, A, B, G are as defined in claim 1 and $L^2$ is as defined above, with a compound of formula XI, as defined above;

(i) for compounds of formula I in which $R^4$ represents —E—$NH_2$, reduction of a compound of formula XIIIA or XIIIB,

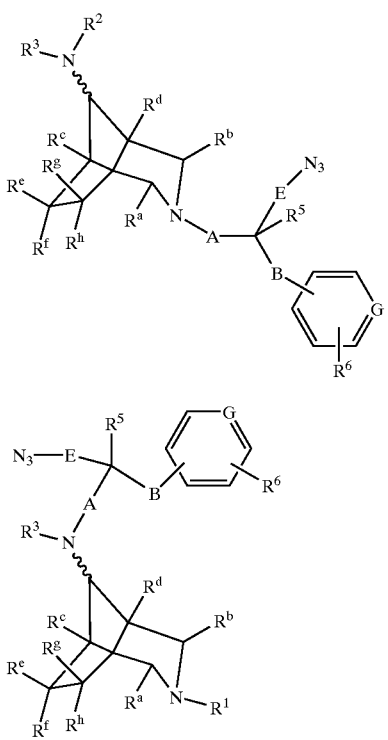

XIIIA

XIIIB wherein R¹ or R² (as appropriate) represents R$^{1a}$, and R$^{1a}$, R³, R⁵, R⁶, R$^a$ to R$^h$, A, B, E and G are as defined in claim 1;

(j) for compounds of formula I in which R⁴ represents —E—N(R¹⁹)R²⁰, wherein R¹⁹ represents C$_{1-6}$ alkyl, —E-aryl —E—Het⁸, —C(O)R$^{21a}$, —C(O)OR$^{21b}$, —S(O)$_2$R$^{21c}$ or —C(O)N(R$^{22a}$)R$^{22b}$, reaction of a corresponding compound of formula I in which R⁴ represents —E—N(H)R²⁰ with a compound of formula XIV, R$^{19a}$—L¹  XIV wherein R$^{19a}$ represents C$_{1-6}$ alkyl, —E-aryl —E—Het⁸, —C(O)R$^{21a}$, —C(O)OR$^{21b}$, —S(O)$_2$R$^{21c}$ or —C(O)N(R$^{22a}$)R$^{22b}$, and R$^{21a}$, R$^{21b}$, R$^{21c}$, R$^{22a}$, R$^{22b}$, Het⁸ and E are as defined in claim 1 and L¹ is as defined above;

(k) for compounds of formula I in which R⁴ represents —E—N(R²⁰)C(O)N(H)R$^{22a}$, reaction of a corresponding compound of formula I in which R⁴ represents —E—N(H)R²⁰ with a compound of formula XV, R$^{22a}$—N=C=O  XV wherein R$^{22a}$ is as defined in claim 1;

(l) for compounds of formula I in which R⁴ represents —E—N(H)[C(O)]$_2$NH$_2$, reaction of a corresponding compound of formula I in which R⁴ represents —E—NH$_2$ with oxalic acid diamide;

(m) for compounds of formula I in which R⁴ represents —E—N(H)C(NH)NH$_2$, reaction of a corresponding compound of formula I in which R⁴ represents —E—NH$_2$ with a compound of formula XVI,

R²⁹O—C(=NH)NH$_2$  XVI or an N-protected derivative thereof, wherein R²⁹ represents C$_{1-10}$ alkyl or aryl, which groups are optionally substituted by one or more halo or nitro groups;

(n) for compounds of formula I in which R⁴ represents —OR¹⁸, in which R¹⁸ represents —C(O)R$^{21a}$, —C(O)OR$^{21b}$ or —C(O)N(R$^{22a}$)R$^{22b}$, reaction of a corresponding compound of formula I in which R⁴ represents —OH with a compound of formula XVII, R$^{18b}$—L³  XVII wherein R$^{18b}$ represents —C(O)R$^{21a}$, —C(O)OR$^{21b}$ or —C(O)N(R$^{22a}$)R$^{22b}$, L³ represents a leaving group and R$^{21a}$, R$^{21b}$, R$^{22a}$ and R$^{22b}$ are as defined in claim 1;

(o) for compounds of formula I in which R⁴ represents H or —OH and R⁵ represents H, reduction of a corresponding compound of formula I in which R⁴ and R⁵ together represent =O;

(p) for compounds of formula I in which R⁴ represents halo, substitution of a corresponding compound of formula I in which R⁴ represents —OH, using a halogenating agent;

(q) for compounds of formula I in which R⁴ and R⁵ represent H, A represents —J— and B represents —N(R²⁵)—Z— (wherein —N(R²⁵) is attached to the carbon atom bearing R⁴ and R⁵), reaction of a compound of formula XVIIIA or XVIIIB,

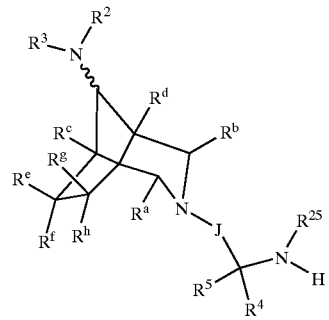

XVIIIA

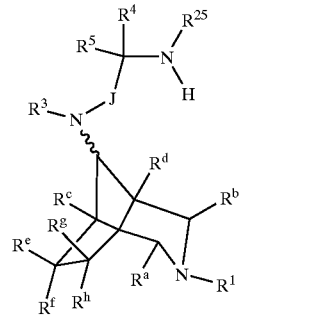

XVIIIB wherein R¹ or R² (as appropriate) represents R$^{1a}$, and R$^{1a}$, R³, R⁴, R⁵, R²⁵, R$^a$ to R$^h$ and J are as defined in claim 1, with a compound of formula XIX,

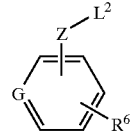

XIX wherein R⁶, G and Z are as defined in claim 1 and L² is as defined above;

(r) for compounds of formula I in which A represents C$_2$ alkylene and R⁴ and R⁵ together represent =O, reaction of a compound of formula IIA or IIB, as defined above (except that $R^1$ or $R^2$ (as appropriate) does not represent a fragment of formula Ia), with a compound of formula XX,

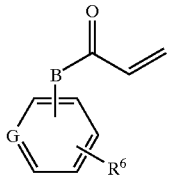

XX wherein B, G and $R^6$ are as defined in claim 1;

(s) for compounds of formula I in which $R^3$ represents H and $R^2$ represents unsubstituted $C_{1-4}$ alkyl, reaction of a compound of formula XXI,

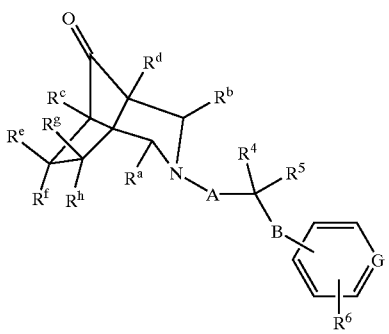

XXI wherein $R^4$, $R^5$, $R^6$, $R^a$ to $R^h$, A, B and G are as defined in claim 1, with a compound of formula XXII, $R^{31}$—$NH_2$     XXII wherein $R^{31}$ represents unsubstituted $C_{1-4}$ alkyl, in the presence of a reducing agent;

(t) for compounds of formula I in which $R^1$ represents —C(O)OR$^9$ and $R^a$ and/or $R^b$ represent $C_{1-4}$ alkyl, reaction of a corresponding compound of formula I in which $R^1$ represents —C(O)OR$^9$ and $R^a$ and $R^b$ represent H with one or more equivalents of a compound of formula XXIII, $R^{32}$—$L^4$     XXIII wherein $R^{32}$ represents $C_{1-4}$ alkyl and $L^4$ is a leaving group, in the presence of a strong base;

(u) for compounds of formula I which are 3-azabicyclo[3.2.1]octane-nitrogen N-oxide derivatives, oxidation of the corresponding 3-azabicyclo-[3.2.1]octane nitrogen of a corresponding compound of formula I, in the presence of an oxidising agent;

(v) for compounds of formula I which are $C_{1-4}$ alkyl quaternary ammonium salt derivatives, in which the alkyl group is attached to a 3-azabicyclo[3.2.1]octane nitrogen, reaction, at the 3-azabicyclo[3.2.1]octane nitrogen, of a corresponding compound of formula I with a compound of formula XXIII, as defined above;

(w) conversion of one $R^6$ substituent to another; or (x) deprotection of a protected derivative of a compound of formula I as defined in claim 1.

39. A compound of formula IIA or IIB, as defined in claim 38, or a protected derivative thereof, provided that the compound is not:

(±) (8α,β)-3-ethyl-3-azabicyclo[3.2.1]octan-8-amine;

8-amino-3-methyl-3-azabicyclo[3.2.1]octane;

8-amino-3-isopropyl-3-azabicyclo[3.2.1]octane;

8-amino-3-benzyl-3-azabicyclo[3.2.1]octane;

3-{2-[4-(6-aminopyridin-2-yl)phenyl]ethyl}-3-azabicyclo[3.2.1]oct-8-ylamine; or 3-azabicyclo[3.2.1]oct-8-ylamine t-butylcarbamate.

40. A compound of formula IVA or IVB, as defined in claim 38, or a protected derivative thereof.

41. A compound of formula VIIIA or VIIIB, as defined in claim 38, or a protected derivative thereof.

42. A compound of formula XIIA or XIIB, as defined in claim 38, or a protected derivative thereof.

43. A compound of formula XIIIA or XIIIB, as defined in claim 38, or a protected derivative thereof.

44. A compound of formula XVIIIA or XVIIIB, as defined in claim 38, or a protected derivative thereof.

45. A compound of formula XXI, as defined in claim 38 (provided that when $R^a$ to $R^h$ all represent H, G represents CH and $R^6$ is absent, then the group —A—C($R^4$)($R^5$)—B— does not represent unsubstituted ethyl), or a protected derivative thereof.

46. A compound of formula XXIV,

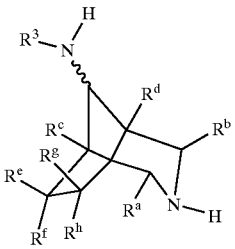

XXIV wherein $R^3$ and $R^a$ to $R^h$ are as defined in claim 1 (provided that $R^a$ to $R^h$ do not all represent H), or a protected derivative thereof.

47. A method as claimed in claim 37 wherein the arrhythmia is an atrial or a ventricular arrhythmia.

* * * * *